(12) United States Patent
Hartdegen et al.

(10) Patent No.: US 11,179,149 B2
(45) Date of Patent: Nov. 23, 2021

(54) COUNTER-TORQUE IMPLANT

(71) Applicant: CROSSROADS EXTREMITY SYSTEMS, LLC, Memphis, TN (US)

(72) Inventors: Vernon R. Hartdegen, Collierville, TN (US); Michael Chad Hollis, Collierville, TN (US); Scott Hill, Atoka, TN (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 356 days.

(21) Appl. No.: 16/031,764

(22) Filed: Jul. 10, 2018

(65) Prior Publication Data

US 2018/0353172 A1    Dec. 13, 2018

Related U.S. Application Data

(63) Continuation-in-part of application No. PCT/US2018/017229, filed on Feb. 7, 2018.
(Continued)

(51) Int. Cl.
| | |
|---|---|
| *A61B 17/064* | (2006.01) |
| *A61B 17/80* | (2006.01) |
| *A61B 17/17* | (2006.01) |
| *A61B 17/68* | (2006.01) |
| *A61B 17/068* | (2006.01) |

(Continued)

(52) U.S. Cl.
CPC ...... *A61B 17/0642* (2013.01); *A61B 17/0682* (2013.01); *A61B 17/1604* (2013.01); *A61B 17/1615* (2013.01); *A61B 17/17* (2013.01); *A61B 17/68* (2013.01); *A61B 17/809* (2013.01); *A61B 17/8061* (2013.01); *A61B 17/8872* (2013.01); *A61F 2/30724* (2013.01); *A61F 2/4202* (2013.01); *A61F 2/4455* (2013.01); *A61B 2017/0641* (2013.01); *A61B 2017/0645* (2013.01); *A61B 2017/681* (2013.01); *A61B 2090/031* (2016.02); *A61B 2090/033* (2016.02); *A61B 2090/062* (2016.02); *A61F 2002/2835* (2013.01); *A61F 2002/3082* (2013.01); *A61F 2002/3093* (2013.01); *A61F 2002/30622* (2013.01); *A61F 2002/30754* (2013.01); *A61F 2002/30795* (2013.01); *A61F 2002/30808* (2013.01); *A61F 2002/30828* (2013.01)

(58) Field of Classification Search
CPC ... A61B 17/0642; A61B 17/809; A61B 17/17; A61B 17/0645; A61B 2017/00367; A61B 2017/0641; A61B 17/0643
See application file for complete search history.

(56) References Cited

U.S. PATENT DOCUMENTS

| | | | |
|---|---|---|---|
| 2,010,913 | A | 8/1935 | Bruce |
| 2,133,859 | A | 10/1938 | Hawley |

(Continued)

FOREIGN PATENT DOCUMENTS

| | | |
|---|---|---|
| CA | 2063484 | 9/1993 |
| CN | 2404495 | 11/2000 |

(Continued)

*Primary Examiner* — David W Bates
(74) *Attorney, Agent, or Firm* — David Meibos; Maywood IP Law

(57) ABSTRACT

Implants with integral or modular anti-rotation features and related instruments are disclosed. The anti-rotation features do not preclude the implants from applying compression.

32 Claims, 36 Drawing Sheets

Related U.S. Application Data

(60) Provisional application No. 62/455,754, filed on Feb. 7, 2017, provisional application No. 62/456,098, filed on Feb. 7, 2017.

(51) Int. Cl.

| | | |
|---|---|---|
| *A61B 17/16* | (2006.01) | |
| *A61B 17/88* | (2006.01) | |
| *A61F 2/44* | (2006.01) | |
| *A61F 2/30* | (2006.01) | |
| *A61F 2/42* | (2006.01) | |
| *A61B 90/00* | (2016.01) | |
| *A61F 2/28* | (2006.01) | |

(56) References Cited

U.S. PATENT DOCUMENTS

| | | | |
|---|---|---|---|
| 2,544,492 | A | 3/1951 | Downing |
| 2,811,073 | A | 10/1957 | Hans |
| 3,741,205 | A | 6/1973 | Markolf |
| 4,263,903 | A | 4/1981 | Griggs |
| 4,278,091 | A | 7/1981 | Borzone |
| 4,415,111 | A | 11/1983 | McHarrie |
| 4,438,769 | A | 3/1984 | Pratt |
| 4,454,875 | A | 6/1984 | Pratt |
| 4,484,570 | A | 11/1984 | Sutter |
| 4,655,222 | A | 4/1987 | Florez |
| 4,723,540 | A * | 2/1988 | Gilmer, Jr. ......... A61B 17/0642 411/456 |
| 4,805,617 | A | 2/1989 | Bedi |
| 4,848,328 | A | 7/1989 | Laboureau |
| 4,852,558 | A | 8/1989 | Outerbridge |
| 5,013,315 | A | 5/1991 | Barrows |
| 5,044,540 | A | 9/1991 | Dulebohn |
| 5,209,756 | A | 5/1993 | Seedhom |
| 5,246,443 | A | 9/1993 | Mai |
| 5,258,012 | A | 11/1993 | Luscombe |
| 5,352,229 | A * | 10/1994 | Goble ................ A61B 17/0642 606/220 |
| 5,395,372 | A | 3/1995 | Holt |
| 5,425,489 | A | 6/1995 | Shichman |
| 5,449,359 | A | 9/1995 | Groiso |
| 5,454,814 | A | 10/1995 | Comte |
| 5,456,400 | A | 10/1995 | Shichman |
| 5,490,409 | A | 2/1996 | Weber |
| 5,498,749 | A | 3/1996 | Heise |
| 5,520,700 | A | 5/1996 | Beyar |
| 5,578,034 | A | 11/1996 | Estes |
| 5,607,425 | A | 3/1997 | Rogozinski |
| 5,628,740 | A | 5/1997 | Mullane |
| 5,634,926 | A | 6/1997 | Jobe |
| 5,660,188 | A | 8/1997 | Groiso |
| 5,662,655 | A * | 9/1997 | Laboureau ......... A61B 17/0642 606/75 |
| 5,716,357 | A | 2/1998 | Rogozinski |
| 5,749,564 | A | 5/1998 | Malek |
| 5,779,707 | A | 7/1998 | Bertholet |
| 5,785,713 | A | 7/1998 | Jobe |
| 5,788,698 | A | 8/1998 | Savornin |
| 5,807,403 | A | 9/1998 | Beyar |
| 5,853,414 | A | 12/1998 | Groiso |
| 5,904,682 | A | 5/1999 | Rogozinski |
| 5,931,839 | A | 8/1999 | Medoff |
| 5,947,968 | A | 9/1999 | Rogozinski |
| 5,947,999 | A | 9/1999 | Groiso |
| 5,972,000 | A | 10/1999 | Beyar |
| 5,993,476 | A | 11/1999 | Groiso |
| 6,010,504 | A | 1/2000 | Rogozinski |
| 6,017,343 | A | 1/2000 | Rogozinski |
| 6,019,759 | A | 2/2000 | Rogozinski |
| 6,059,787 | A | 5/2000 | Allen |
| 6,089,435 | A | 7/2000 | Malek |
| 6,105,936 | A | 8/2000 | Malek |
| 6,120,503 | A * | 9/2000 | Michelson ............. A61F 2/446 606/86 A |
| 6,179,840 | B1 | 1/2001 | Bowman |
| 6,187,009 | B1 | 2/2001 | Herzog |
| 6,281,262 | B1 | 8/2001 | Shikinami |
| 6,322,562 | B1 | 11/2001 | Wolter |
| 6,334,446 | B1 | 1/2002 | Beyar |
| 6,336,927 | B2 | 1/2002 | Rogozinski |
| 6,348,054 | B1 | 2/2002 | Allen |
| 6,364,884 | B1 | 4/2002 | Bowman |
| 6,379,354 | B1 | 4/2002 | Rogozinski |
| 6,387,041 | B1 | 5/2002 | Harari |
| 6,402,765 | B1 | 6/2002 | Monassevitch |
| 6,402,766 | B2 | 6/2002 | Bowman |
| 6,406,480 | B1 | 6/2002 | Beyar |
| 6,423,073 | B2 | 7/2002 | Bowman |
| 6,436,110 | B2 | 8/2002 | Bowman |
| 6,447,517 | B1 | 9/2002 | Bowman |
| 6,497,707 | B1 | 12/2002 | Bowman |
| 6,544,273 | B1 | 4/2003 | Harari |
| 6,575,984 | B2 | 6/2003 | Beyar |
| 6,575,998 | B2 | 6/2003 | Beyar |
| 6,582,435 | B2 | 6/2003 | Wellisz |
| 6,592,610 | B2 | 7/2003 | Beyar |
| 6,635,058 | B2 | 10/2003 | Beyar |
| 6,652,531 | B2 | 11/2003 | Wellisz |
| 6,663,642 | B2 | 12/2003 | Beyar |
| 6,679,885 | B2 | 1/2004 | Wellisz |
| 6,709,437 | B2 | 3/2004 | Wellisz |
| 6,730,110 | B1 | 5/2004 | Harari |
| 6,746,455 | B2 | 6/2004 | Beyar |
| 6,783,531 | B2 | 8/2004 | Allen |
| 6,896,684 | B2 | 5/2005 | Monassevitch |
| 6,966,911 | B2 | 11/2005 | Groiso |
| 6,974,461 | B1 | 12/2005 | Wolter |
| 7,044,951 | B2 | 5/2006 | Medoff |
| 7,090,676 | B2 | 8/2006 | Huebner |
| 7,147,640 | B2 | 12/2006 | Huebner |
| 7,153,309 | B2 | 12/2006 | Huebner |
| 7,179,260 | B2 | 2/2007 | Gerlach |
| 7,189,237 | B2 | 3/2007 | Huebner |
| 7,214,232 | B2 | 5/2007 | Bowman |
| 7,226,408 | B2 | 6/2007 | Harai |
| 7,229,452 | B2 | 6/2007 | Kayan |
| 7,235,079 | B2 | 6/2007 | Jensen |
| 7,250,054 | B2 | 7/2007 | Allen |
| 7,255,701 | B2 | 8/2007 | Allen |
| 7,311,712 | B2 | 12/2007 | Dalton |
| 7,326,212 | B2 | 2/2008 | Huebner |
| 7,438,209 | B1 | 10/2008 | Hess |
| 7,473,255 | B2 | 1/2009 | McGarity |
| 7,473,257 | B2 | 1/2009 | Knöpfle et al. |
| 7,500,979 | B2 | 3/2009 | Hueil |
| 7,506,791 | B2 | 3/2009 | Omaits |
| 7,537,596 | B2 | 5/2009 | Jensen |
| 7,537,603 | B2 | 5/2009 | Huebner |
| 7,537,604 | B2 | 5/2009 | Huebner |
| 7,556,647 | B2 | 7/2009 | Drews |
| 7,562,105 | B2 | 7/2009 | Liu |
| 7,578,825 | B2 | 8/2009 | Huebner |
| 7,604,151 | B2 | 10/2009 | Hess |
| 7,618,441 | B2 | 11/2009 | Groiso |
| 7,651,498 | B2 | 1/2010 | Shifrin |
| 7,665,647 | B2 | 2/2010 | Shelton, IV |
| 7,669,746 | B2 | 3/2010 | Shelton, IV |
| 7,669,747 | B2 | 3/2010 | Weisenburgh, II |
| 7,673,781 | B2 | 3/2010 | Swayze |
| 7,673,782 | B2 | 3/2010 | Hess |
| 7,704,251 | B2 | 4/2010 | Huebner |
| 7,704,279 | B2 | 4/2010 | Moskowitz |
| 7,717,945 | B2 | 5/2010 | Jensen |
| 7,735,703 | B2 | 6/2010 | Morgan |
| 7,740,634 | B2 | 6/2010 | Orbay |
| 7,766,209 | B2 | 8/2010 | Baxter, III |
| 7,766,948 | B1 | 8/2010 | Leung |
| 7,771,433 | B2 | 8/2010 | Orbay |
| 7,794,475 | B2 | 9/2010 | Hess |
| 7,832,612 | B2 | 11/2010 | Baxter, III |
| 7,846,188 | B2 | 12/2010 | Moskowitz |
| 7,857,186 | B2 | 12/2010 | Baxter, III |
| 7,857,836 | B2 | 12/2010 | Huebner |

(56) References Cited

U.S. PATENT DOCUMENTS

| | | |
|---|---|---|
| 7,867,265 B2 | 1/2011 | Beutter |
| 7,905,381 B2 | 3/2011 | Baxter, III |
| 7,905,910 B2 | 3/2011 | Gerlach |
| 7,909,858 B2 | 3/2011 | Gerlach |
| 7,914,532 B2 | 3/2011 | Shaver |
| 7,918,879 B2 | 4/2011 | Yeung |
| 7,927,332 B2 | 4/2011 | Huebner |
| 7,934,630 B2 | 5/2011 | Shelton, IV |
| 7,935,126 B2 | 5/2011 | Orbay |
| 7,942,903 B2 | 5/2011 | Moskowitz |
| 7,951,180 B2 | 5/2011 | Moskowitz |
| 7,954,686 B2 | 6/2011 | Baxter, III |
| 7,955,388 B2 | 6/2011 | Jensen |
| 7,963,982 B2 | 6/2011 | Kirschman |
| 7,966,799 B2 | 6/2011 | Morgan |
| 7,972,363 B2 | 7/2011 | Moskowitz |
| 8,016,867 B2 | 9/2011 | Bowman |
| 8,043,346 B2 | 10/2011 | Markworth |
| 8,100,953 B2 | 1/2012 | White |
| 8,105,367 B2 | 1/2012 | Austin |
| 8,114,139 B2 | 2/2012 | Sournac |
| 8,137,351 B2 | 3/2012 | Prandi |
| 8,141,762 B2 | 3/2012 | Bedi |
| 8,172,886 B2 | 5/2012 | Castaneda |
| 8,177,819 B2 | 5/2012 | Huebner |
| 8,182,518 B2 | 5/2012 | Butler |
| 8,186,560 B2 | 5/2012 | Hess |
| 8,205,781 B2 | 6/2012 | Baxter, III |
| 8,220,690 B2 | 7/2012 | Hess |
| 8,231,627 B2 | 7/2012 | Huebner |
| 8,231,662 B2 | 7/2012 | Huebner |
| 8,241,326 B2 | 8/2012 | Harari |
| 8,241,338 B2 | 8/2012 | Castaneda |
| 8,252,032 B2 | 8/2012 | White |
| 8,257,370 B2 | 9/2012 | Moskowitz |
| 8,262,711 B2 | 9/2012 | Hess |
| 8,287,543 B2 * | 10/2012 | Medoff ................ A61B 17/809 606/74 |
| 8,317,070 B2 | 11/2012 | Hueil |
| 8,337,537 B2 | 12/2012 | Pelo |
| 8,348,129 B2 | 1/2013 | Bedi |
| 8,348,131 B2 | 1/2013 | Omaits |
| 8,353,913 B2 | 1/2013 | Moskowitz |
| 8,360,297 B2 | 1/2013 | Shelton, IV |
| 8,365,976 B2 | 2/2013 | Hess |
| 8,382,807 B2 | 2/2013 | Austin |
| 8,393,517 B2 | 3/2013 | Milo |
| 8,398,717 B2 | 3/2013 | Kleinman |
| 8,413,872 B2 | 4/2013 | Patel |
| 8,425,574 B2 | 4/2013 | Huebner |
| 8,425,575 B2 | 4/2013 | Huebner |
| 8,425,576 B2 | 4/2013 | Anderson |
| 8,430,292 B2 | 4/2013 | Patel |
| 8,449,561 B2 | 5/2013 | Bowman |
| 8,453,908 B2 | 6/2013 | Bedi |
| 8,464,923 B2 | 6/2013 | Shelton, IV |
| 8,475,504 B2 | 7/2013 | Gillard |
| 8,485,412 B2 | 7/2013 | Shelton, IV |
| 8,486,116 B2 | 7/2013 | Heilman |
| 8,496,693 B2 | 7/2013 | Robinson |
| 8,499,993 B2 | 8/2013 | Shelton, IV |
| 8,518,090 B2 | 8/2013 | Huebner |
| 8,523,919 B2 | 9/2013 | Huebner |
| 8,540,129 B2 | 9/2013 | Baxter, III |
| 8,540,133 B2 | 9/2013 | Bedi |
| 8,545,540 B2 | 10/2013 | Castaneda |
| 8,561,870 B2 | 10/2013 | Baxter, III |
| 8,567,656 B2 | 10/2013 | Shelton, IV |
| 8,574,270 B2 | 11/2013 | Hess |
| 8,584,853 B2 * | 11/2013 | Knight ...................... A61L 2/26 206/439 |
| 8,585,743 B2 | 11/2013 | Ampuero |
| 8,590,762 B2 | 11/2013 | Hess |
| 8,596,514 B2 | 12/2013 | Miller |
| 8,603,161 B2 | 12/2013 | Drews |
| 8,636,187 B2 | 1/2014 | Hueil |
| 8,652,142 B2 | 2/2014 | Geissler |
| 8,652,180 B2 | 2/2014 | Federspiel |
| 8,657,820 B2 | 2/2014 | Kubiak |
| 8,668,130 B2 | 3/2014 | Hess |
| 8,672,208 B2 | 3/2014 | Hess |
| 8,672,828 B2 | 3/2014 | Harari |
| 8,679,123 B2 | 3/2014 | Kinmon |
| 8,720,766 B2 | 5/2014 | Hess |
| 8,727,197 B2 | 5/2014 | Hess |
| 8,728,128 B2 | 5/2014 | Hawkes |
| 8,728,129 B2 | 5/2014 | Fritzinger |
| 8,734,516 B2 | 5/2014 | Moskowitz |
| 8,740,915 B2 | 6/2014 | Niederberger |
| 8,747,444 B2 | 6/2014 | Moskowitz |
| 8,763,875 B2 | 7/2014 | Morgan |
| 8,777,969 B2 | 7/2014 | Kayan |
| 8,779,927 B2 | 7/2014 | Bell |
| 8,784,450 B2 | 7/2014 | Moskowitz |
| 8,800,838 B2 | 8/2014 | Shelton, IV |
| 8,808,325 B2 | 8/2014 | Hess |
| 8,814,915 B2 | 8/2014 | Hess |
| 8,834,537 B2 | 9/2014 | Castaneda |
| 8,858,562 B2 | 10/2014 | Orbay |
| 8,870,882 B2 | 10/2014 | Kleiner |
| 8,882,812 B2 | 11/2014 | Hess |
| 8,888,824 B2 | 11/2014 | Austin |
| 8,888,826 B2 | 11/2014 | Kinmon |
| 8,894,651 B2 | 11/2014 | Aflatoon |
| 8,899,465 B2 | 12/2014 | Shelton, IV |
| 8,906,046 B2 | 12/2014 | Anderson |
| 8,925,788 B2 | 1/2015 | Hess |
| 8,940,028 B2 | 1/2015 | Austin |
| 8,973,804 B2 | 3/2015 | Hess |
| 8,974,504 B2 | 3/2015 | Hess |
| 8,986,305 B2 | 3/2015 | Aflatoon |
| 8,991,676 B2 | 3/2015 | Hess |
| 8,992,581 B2 | 3/2015 | Austin |
| 9,005,206 B2 | 4/2015 | Ampuero |
| 9,005,293 B2 | 4/2015 | Moskowitz |
| 9,017,331 B2 | 4/2015 | Fox |
| 9,017,380 B2 | 4/2015 | Mayer |
| 9,034,037 B2 | 5/2015 | Fiere |
| 9,072,554 B2 | 7/2015 | Reynolds |
| 9,078,757 B2 | 7/2015 | Kleinman |
| 9,095,338 B2 * | 8/2015 | Taylor ................ A61B 17/0682 |
| 9,095,388 B2 | 8/2015 | Hess |
| 9,101,349 B2 | 8/2015 | Knight |
| 9,107,661 B2 | 8/2015 | Euteneuer |
| 9,125,650 B2 | 9/2015 | Euteneuer |
| 9,138,233 B2 | 9/2015 | Anderson |
| 9,179,911 B2 | 11/2015 | Morgan |
| 9,180,022 B2 | 11/2015 | Georges |
| 9,204,932 B2 | 12/2015 | Knight |
| 9,220,515 B2 | 12/2015 | Castaneda et al. |
| 9,237,891 B2 | 1/2016 | Shelton, IV |
| 9,247,978 B2 | 2/2016 | Euteneuer |
| 9,265,649 B2 | 2/2016 | Pflueger |
| D752,219 S | 3/2016 | Peterson |
| 9,271,726 B2 | 3/2016 | Euteneuer |
| 9,283,006 B2 | 3/2016 | Fonte |
| 9,289,206 B2 | 3/2016 | Hess |
| 9,289,210 B2 | 3/2016 | Baxter, III |
| 9,301,854 B2 | 4/2016 | Moskowitz |
| 9,307,988 B2 | 4/2016 | Shelton, IV |
| 9,308,033 B2 | 4/2016 | Huebner |
| 9,326,768 B2 | 5/2016 | Shelton, IV |
| 9,326,771 B2 | 5/2016 | Baxter, III |
| 9,339,268 B2 | 5/2016 | Fox |
| 9,370,355 B2 | 6/2016 | Anderson |
| 9,370,356 B2 | 6/2016 | Euteneuer |
| 9,370,376 B2 | 6/2016 | Castaneda |
| 9,387,116 B2 | 7/2016 | Pflueger |
| 9,402,623 B2 | 8/2016 | Kayan |
| 9,402,624 B1 | 8/2016 | Scott |
| 9,408,603 B2 | 8/2016 | Patel |
| 9,408,604 B2 | 8/2016 | Shelton, IV |
| 9,414,841 B2 | 8/2016 | Euteneuer |
| 9,414,871 B2 | 8/2016 | Huebner et al. |

(56) References Cited

U.S. PATENT DOCUMENTS

| | | |
|---|---|---|
| 9,421,013 B2 | 8/2016 | Patel |
| 9,445,808 B2 | 9/2016 | Woodard, Jr. |
| 9,451,957 B2 | 9/2016 | Fox |
| 9,463,015 B2 | 10/2016 | Hausen |
| 9,486,212 B2 | 11/2016 | Miller |
| 9,532,821 B2 | 1/2017 | Moskowitz |
| 9,539,023 B2 | 1/2017 | Marotte |
| 9,549,735 B2 | 1/2017 | Shelton, IV |
| 9,561,032 B2 | 2/2017 | Shelton, IV |
| 9,566,063 B2 | 2/2017 | Euteneuer |
| 9,603,641 B2 | 3/2017 | Hulliger |
| 9,615,856 B2 | 4/2017 | Arnett |
| 9,763,715 B2 | 9/2017 | Mather |
| 9,918,762 B2 | 3/2018 | Federspiel |
| 9,924,984 B2 | 3/2018 | Hartdegen |
| 9,955,964 B2 * | 5/2018 | Mayer .................... A61B 17/68 |
| 10,166,022 B2 * | 1/2019 | Early ................ A61B 17/0642 |
| 10,186,402 B2 | 1/2019 | Kamata |
| 10,357,986 B2 | 7/2019 | Zhou |
| D870,284 S * | 12/2019 | Hollis .......................... D24/155 |
| 10,492,841 B2 * | 12/2019 | Hartdegen ......... A61B 17/0682 |
| D892,331 S * | 8/2020 | Hollis .......................... D24/155 |
| 2001/0028148 A1 | 10/2001 | White |
| 2002/0095155 A1 | 7/2002 | Michelson |
| 2002/0095181 A1 | 7/2002 | Beyar |
| 2002/0111641 A1 | 8/2002 | Peterson |
| 2003/0083663 A1 | 5/2003 | Goldhahn |
| 2003/0158553 A1 | 8/2003 | Michelson |
| 2003/0225409 A1 | 12/2003 | Freid |
| 2004/0073222 A1 | 4/2004 | Koseki |
| 2004/0127896 A1 | 7/2004 | Lombardo |
| 2004/0172040 A1 | 9/2004 | Heggeness |
| 2004/0220570 A1 | 11/2004 | Frigg |
| 2005/0021032 A1 | 1/2005 | Koo |
| 2005/0021035 A1 | 1/2005 | Groiso |
| 2005/0043757 A1 | 2/2005 | Arad |
| 2005/0049600 A1 | 3/2005 | Groiso |
| 2005/0085818 A1 | 4/2005 | Huebner |
| 2005/0096660 A1 | 5/2005 | Allen |
| 2005/0101961 A1 | 5/2005 | Huebner |
| 2005/0107796 A1 | 5/2005 | Gerlach |
| 2005/0119667 A1 | 6/2005 | Leport |
| 2005/0165400 A1 | 7/2005 | Fernandez |
| 2005/0171544 A1 | 8/2005 | Falkner |
| 2005/0234458 A1 | 10/2005 | Huebner |
| 2005/0240187 A1 | 10/2005 | Huebner |
| 2006/0058796 A1 | 3/2006 | Hartdegen |
| 2006/0058802 A1 * | 3/2006 | Kofoed ................ A61B 17/562 606/75 |
| 2006/0106391 A1 | 5/2006 | Huebner |
| 2006/0122604 A1 | 6/2006 | Gorhan |
| 2006/0122605 A1 | 6/2006 | Suh |
| 2006/0129151 A1 | 6/2006 | Allen |
| 2006/0200147 A1 | 9/2006 | Ensign |
| 2006/0241612 A1 | 10/2006 | Medoff |
| 2006/0241618 A1 | 10/2006 | Gasser |
| 2006/0264936 A1 | 11/2006 | Partin |
| 2007/0055249 A1 | 3/2007 | Jensen |
| 2007/0173840 A1 | 7/2007 | Huebner |
| 2007/0191850 A1 * | 8/2007 | Kim ................... A61B 17/1764 606/75 |
| 2007/0208358 A1 | 9/2007 | Kayan |
| 2007/0233116 A1 | 10/2007 | Olerud |
| 2008/0147125 A1 | 6/2008 | Colleran |
| 2008/0195099 A1 | 8/2008 | Minas |
| 2008/0200955 A1 | 8/2008 | Tepic |
| 2008/0255620 A1 | 10/2008 | Strauss |
| 2008/0275510 A1 | 11/2008 | Schonhardt |
| 2008/0288000 A1 | 11/2008 | Cawley |
| 2008/0319443 A1 * | 12/2008 | Focht ................ A61B 17/0642 606/75 |
| 2009/0054930 A1 | 2/2009 | Aflatoon |
| 2009/0138082 A1 | 5/2009 | Reah |
| 2009/0177203 A1 | 7/2009 | Reiley |
| 2009/0182383 A1 | 7/2009 | Prybyla |
| 2009/0187247 A1 | 7/2009 | Metcalf, Jr. |
| 2009/0254090 A1 * | 10/2009 | Lizee ................ A61B 17/0642 606/75 |
| 2009/0254126 A1 | 10/2009 | Orbay |
| 2009/0281543 A1 | 11/2009 | Orbay |
| 2010/0036430 A1 | 2/2010 | Hartdegen |
| 2010/0076448 A1 | 3/2010 | Abdou |
| 2010/0082065 A1 | 4/2010 | Butler |
| 2010/0100138 A1 | 4/2010 | Reynolds |
| 2010/0106196 A1 | 4/2010 | Erickson |
| 2010/0125275 A1 * | 5/2010 | Kinmon ............ A61B 17/0642 606/75 |
| 2010/0133316 A1 | 6/2010 | Lizee |
| 2010/0211116 A1 | 8/2010 | Suh |
| 2010/0256765 A1 | 10/2010 | Butler |
| 2010/0292715 A1 | 11/2010 | Nering |
| 2010/0312280 A1 | 12/2010 | Overes |
| 2011/0022049 A1 | 1/2011 | Huebner |
| 2011/0022099 A1 | 1/2011 | Ashman |
| 2011/0029016 A1 | 2/2011 | Yeung |
| 2011/0029023 A1 | 2/2011 | Tornier |
| 2011/0029025 A1 | 2/2011 | Medoff |
| 2011/0054542 A1 | 3/2011 | Kevin |
| 2011/0092981 A1 | 4/2011 | Ng |
| 2011/0098754 A1 | 4/2011 | Hulliger |
| 2011/0118796 A1 | 5/2011 | Reiley |
| 2011/0118840 A1 | 5/2011 | Huntsman |
| 2011/0202092 A1 | 8/2011 | Frigg |
| 2011/0270326 A1 | 11/2011 | Black |
| 2011/0282393 A1 | 11/2011 | Gerlach |
| 2011/0295324 A1 | 12/2011 | Donley |
| 2011/0313421 A1 | 12/2011 | Sidebotham |
| 2011/0319942 A1 | 12/2011 | Bottlang |
| 2012/0022600 A1 | 1/2012 | Overes |
| 2012/0024937 A1 | 2/2012 | Allen |
| 2012/0053638 A1 | 3/2012 | Rusch |
| 2012/0059425 A1 | 3/2012 | Biedermann |
| 2012/0065690 A1 | 3/2012 | Perrow |
| 2012/0078371 A1 | 3/2012 | Gamache |
| 2012/0095513 A1 | 4/2012 | Humphreys |
| 2012/0130374 A1 | 5/2012 | Bouduban |
| 2012/0136396 A1 | 5/2012 | Baker |
| 2012/0143193 A1 | 6/2012 | Hulliger |
| 2012/0150240 A1 | 6/2012 | Medoff |
| 2012/0179207 A1 | 7/2012 | Mekhail |
| 2012/0191141 A1 | 7/2012 | Costabile |
| 2012/0323284 A1 | 12/2012 | Baker |
| 2013/0006247 A1 | 1/2013 | Weiner |
| 2013/0023938 A1 | 1/2013 | Huebner |
| 2013/0023940 A1 | 1/2013 | Hansell |
| 2013/0026206 A1 | 1/2013 | Fox |
| 2013/0030437 A1 | 1/2013 | Fox |
| 2013/0046346 A1 | 2/2013 | Thorwarth |
| 2013/0109910 A1 | 5/2013 | Alexander |
| 2013/0138154 A1 | 5/2013 | Reiley |
| 2013/0150900 A1 | 6/2013 | Haddad |
| 2013/0218285 A1 | 8/2013 | Kleinman |
| 2013/0226252 A1 * | 8/2013 | Mayer ................ A61B 17/0642 606/331 |
| 2013/0231667 A1 * | 9/2013 | Taylor ................ A61B 17/0642 606/75 |
| 2013/0238035 A1 | 9/2013 | Medoff |
| 2013/0267956 A1 | 10/2013 | Terrill |
| 2013/0303071 A1 | 11/2013 | Seki |
| 2013/0325074 A1 | 12/2013 | Ziolo |
| 2013/0345752 A1 | 12/2013 | Hendren |
| 2014/0014553 A1 | 1/2014 | Knight |
| 2014/0018809 A1 | 1/2014 | Allen |
| 2014/0018862 A1 | 1/2014 | Koay |
| 2014/0020333 A1 | 1/2014 | Knight |
| 2014/0024002 A1 | 1/2014 | Knight |
| 2014/0034702 A1 * | 2/2014 | Miller ................ A61B 17/0682 227/175.1 |
| 2014/0058461 A1 | 2/2014 | Black |
| 2014/0100652 A1 | 4/2014 | Drews |
| 2014/0142628 A1 | 5/2014 | Traynelis |
| 2014/0163621 A1 | 6/2014 | Huebner |
| 2014/0163682 A1 | 6/2014 | Iott |
| 2014/0163683 A1 | 6/2014 | Seifert |

(56) References Cited

U.S. PATENT DOCUMENTS

| | | | |
|---|---|---|---|
| 2014/0172026 A1 | 6/2014 | Biedermann | |
| 2014/0200670 A1 | 7/2014 | Chin | |
| 2014/0207195 A1 | 7/2014 | Appenzeller | |
| 2014/0222086 A1 | 8/2014 | Kuster | |
| 2014/0257420 A1 | 9/2014 | Fox | |
| 2014/0276830 A1 | 9/2014 | Cheney | |
| 2014/0296925 A1 | 10/2014 | Lawson | |
| 2014/0309639 A1* | 10/2014 | Averous | A61B 17/0643 606/75 |
| 2014/0316470 A1 | 10/2014 | Hartdegen | |
| 2014/0358187 A1 | 12/2014 | Taber | |
| 2015/0012003 A1 | 1/2015 | Ryan | |
| 2015/0045804 A1 | 2/2015 | Orbay | |
| 2015/0066095 A1 | 3/2015 | Austin | |
| 2015/0080914 A1 | 3/2015 | Roundy | |
| 2015/0080969 A1 | 3/2015 | Holly | |
| 2015/0133940 A1 | 5/2015 | Palmer | |
| 2015/0142063 A1 | 5/2015 | Austin | |
| 2015/0148850 A1 | 5/2015 | Orbay | |
| 2015/0164564 A1 | 6/2015 | Reiley | |
| 2015/0173749 A1 | 6/2015 | Shelton, IV | |
| 2015/0173750 A1 | 6/2015 | Shelton, IV | |
| 2015/0173751 A1 | 6/2015 | Shelton, IV | |
| 2015/0173756 A1 | 6/2015 | Baxter, III | |
| 2015/0196333 A1 | 7/2015 | Austin | |
| 2015/0216570 A1 | 8/2015 | Hess | |
| 2015/0216573 A1 | 8/2015 | Chin | |
| 2015/0238191 A1 | 8/2015 | Schellin | |
| 2015/0238238 A1* | 8/2015 | Cheney | A61B 17/1728 606/281 |
| 2015/0282819 A1* | 10/2015 | Austin | A61B 17/0642 606/96 |
| 2015/0313592 A1 | 11/2015 | Coillard-Lavirotte | |
| 2015/0320462 A1 | 11/2015 | Biedermann | |
| 2015/0351762 A1 | 12/2015 | Vendely | |
| 2015/0351763 A1 | 12/2015 | Shelton, IV | |
| 2015/0351764 A1 | 12/2015 | Shelton, IV | |
| 2016/0015384 A1 | 1/2016 | Roedl | |
| 2016/0066907 A1 | 3/2016 | Cheney | |
| 2016/0074037 A1 | 3/2016 | Cheney | |
| 2016/0089191 A1 | 3/2016 | Pak | |
| 2016/0100835 A1 | 4/2016 | Linder | |
| 2016/0157906 A1* | 6/2016 | Hollis | A61B 17/68 606/328 |
| 2016/0192930 A1* | 7/2016 | Finley | A61B 17/17 606/75 |
| 2016/0199060 A1 | 7/2016 | Morgan | |
| 2016/0235460 A1 | 8/2016 | Wahl | |
| 2016/0242771 A1 | 8/2016 | Weinstein | |
| 2016/0242927 A1 | 8/2016 | Seifert | |
| 2016/0338697 A1* | 11/2016 | Biedermann | A61B 17/0682 |
| 2016/0354117 A1 | 12/2016 | Nakaji | |
| 2017/0000533 A1* | 1/2017 | Fallin | A61B 17/8095 |
| 2017/0007305 A1* | 1/2017 | Hollis | A61B 17/809 |
| 2017/0065276 A1* | 3/2017 | Weiner | A61B 17/0642 |
| 2017/0065312 A1 | 3/2017 | Lauf | |
| 2017/0112553 A1 | 4/2017 | Hansell | |
| 2017/0119443 A1 | 5/2017 | Cawley | |
| 2017/0156776 A1 | 6/2017 | Weiman | |
| 2017/0164990 A1 | 6/2017 | Weiner | |
| 2017/0181779 A1 | 6/2017 | Leither | |
| 2017/0196604 A1 | 7/2017 | Hartdegen | |
| 2017/0196606 A1 | 7/2017 | Cianfrani | |
| 2017/0202552 A1* | 7/2017 | Coleman | A61B 17/16 |
| 2017/0202585 A1 | 7/2017 | Leak | |
| 2017/0209193 A1* | 7/2017 | Hartdegen | A61B 17/1775 |
| 2017/0231625 A1 | 8/2017 | Handie | |
| 2017/0238974 A1 | 8/2017 | Konieczynski | |
| 2017/0245901 A1 | 8/2017 | Grigorian | |
| 2017/0281157 A1* | 10/2017 | Hartdegen | A61B 17/8052 |
| 2017/0354509 A1 | 12/2017 | Finley | |
| 2018/0000592 A1* | 1/2018 | Mayer | A61F 2/30767 |
| 2018/0206892 A1 | 7/2018 | Hartdegen | |
| 2018/0296257 A1 | 10/2018 | Penzimer | |
| 2018/0317906 A1 | 11/2018 | Hollis | |
| 2019/0000451 A1* | 1/2019 | Majors | A61B 17/0682 |
| 2019/0150921 A1 | 5/2019 | Fonte | |
| 2020/0000464 A1* | 1/2020 | Gaston | A61B 17/17 |
| 2020/0000465 A1* | 1/2020 | Maclure | A61B 17/0642 |
| 2020/0008807 A1 | 1/2020 | Hollis | |

FOREIGN PATENT DOCUMENTS

| | | |
|---|---|---|
| DE | 3119550 | 12/1982 |
| DE | 29721858 | 3/1998 |
| DE | 19821680 | 8/1999 |
| DE | 20001879 | 5/2000 |
| DE | 102004015223 | 10/2005 |
| EP | 0092383 | 11/1987 |
| EP | 0253629 | 9/1994 |
| EP | 0768062 | 4/1997 |
| EP | 0826340 | 3/1998 |
| EP | 0857462 | 8/1998 |
| EP | 0682920 | 5/2000 |
| EP | 0867149 | 9/2000 |
| EP | 1870042 | 7/2009 |
| EP | 2231044 | 3/2012 |
| EP | 3082632 | 10/2016 |
| EP | 3166505 | 5/2017 |
| EP | 3166522 | 5/2017 |
| EP | 3179939 | 6/2017 |
| FR | 2628312 B1 | 1/1994 |
| FR | 2694696 | 11/1994 |
| FR | 2725126 | 4/1997 |
| FR | 2758252 | 4/1999 |
| FR | 2874316 | 10/2006 |
| FR | 2927527 | 8/2009 |
| FR | 2874166 | 3/2012 |
| FR | 2935256 | 3/2012 |
| FR | 2980966 | 11/2013 |
| GB | 2118474 | 10/1985 |
| GB | 2471648 | 1/2012 |
| WO | WO1992017122 | 10/1992 |
| WO | WO2001056489 | 8/2001 |
| WO | WO2003068081 | 8/2003 |
| WO | WO2003071962 | 9/2003 |
| WO | WO2008007196 | 1/2008 |
| WO | WO2008129061 | 10/2008 |
| WO | WO2009091770 | 7/2009 |
| WO | WO2010004602 | 1/2010 |
| WO | WO2011014547 | 2/2011 |
| WO | WO2011110916 | 9/2011 |
| WO | WO2012071129 | 5/2012 |
| WO | WO2013010282 | 1/2013 |
| WO | WO2013055824 | 4/2013 |
| WO | WO2013130978 | 9/2013 |
| WO | WO2013186205 | 12/2013 |
| WO | WO2015004391 | 1/2015 |
| WO | WO2015095126 | 6/2015 |
| WO | WO2015107311 | 7/2015 |
| WO | WO2016007624 | 1/2016 |
| WO | WO2016007626 | 1/2016 |
| WO | WO2016025162 | 2/2016 |
| WO | WO2016110760 | 7/2016 |
| WO | WO2017011589 | 1/2017 |
| WO | WO2017139315 | 8/2017 |
| WO | WO2017139328 | 8/2017 |
| WO | WO2018145064 | 8/2018 |
| WO | WO2018148284 | 8/2018 |

* cited by examiner

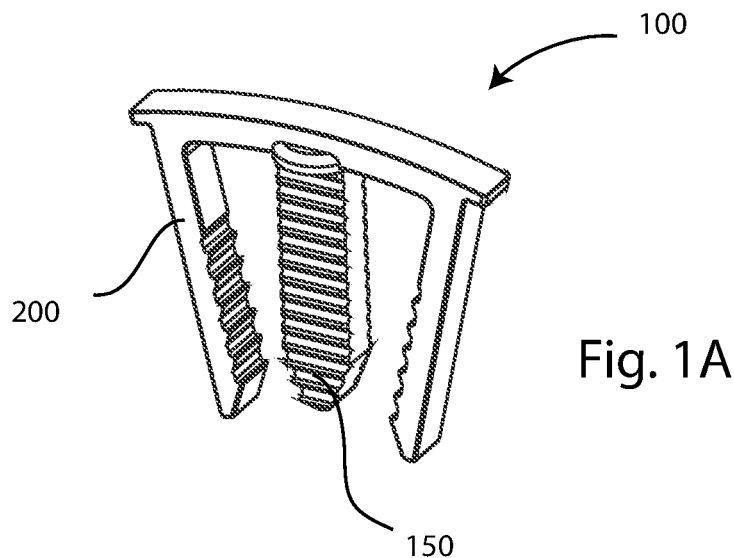
Fig. 1A
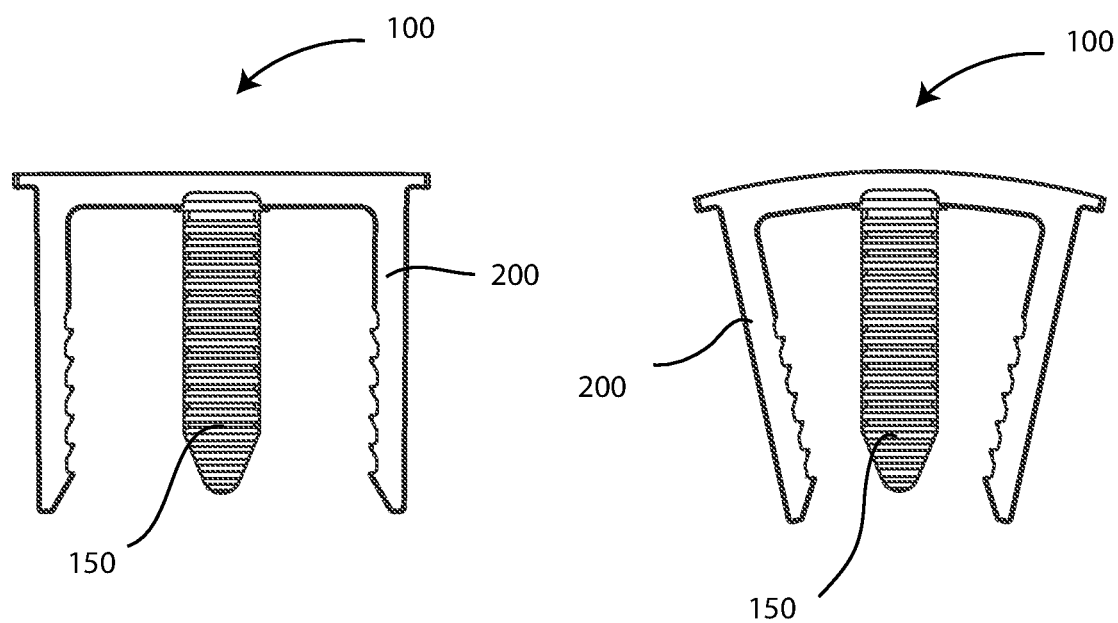
Fig. 1B
Fig. 1C

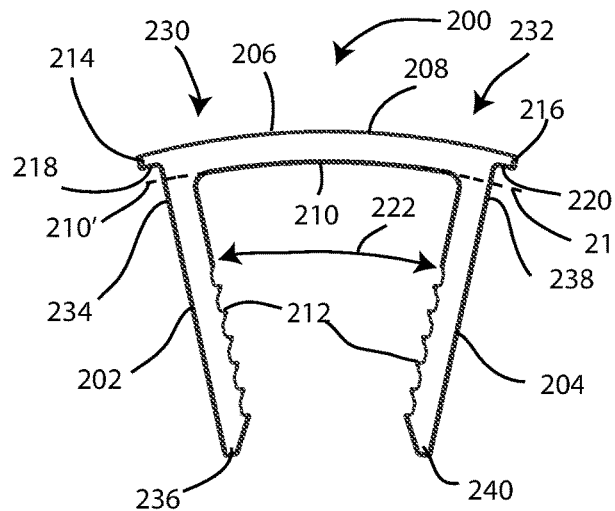
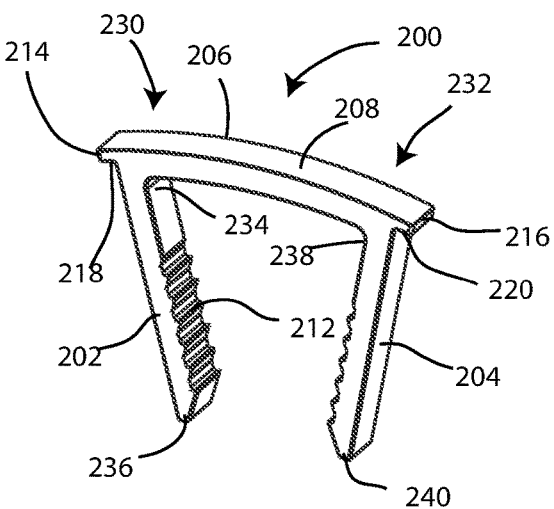
Fig. 2A    Fig. 2B
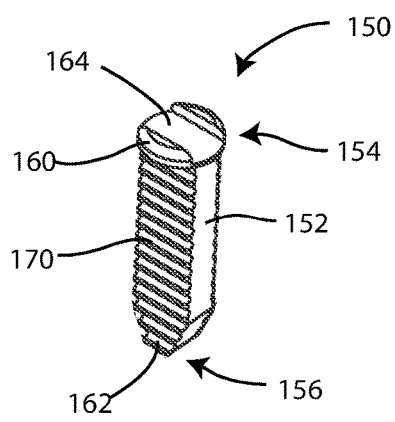
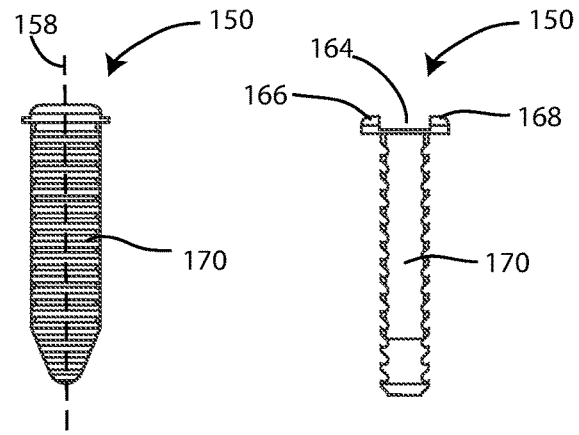
Fig. 3A    Fig. 3B    Fig. 3C
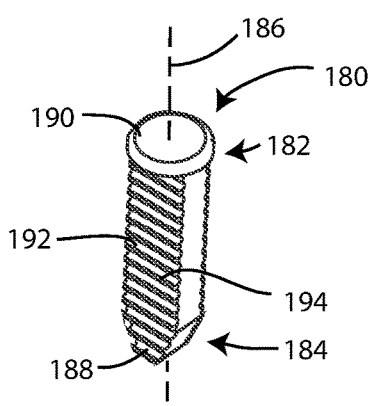
Fig. 3D

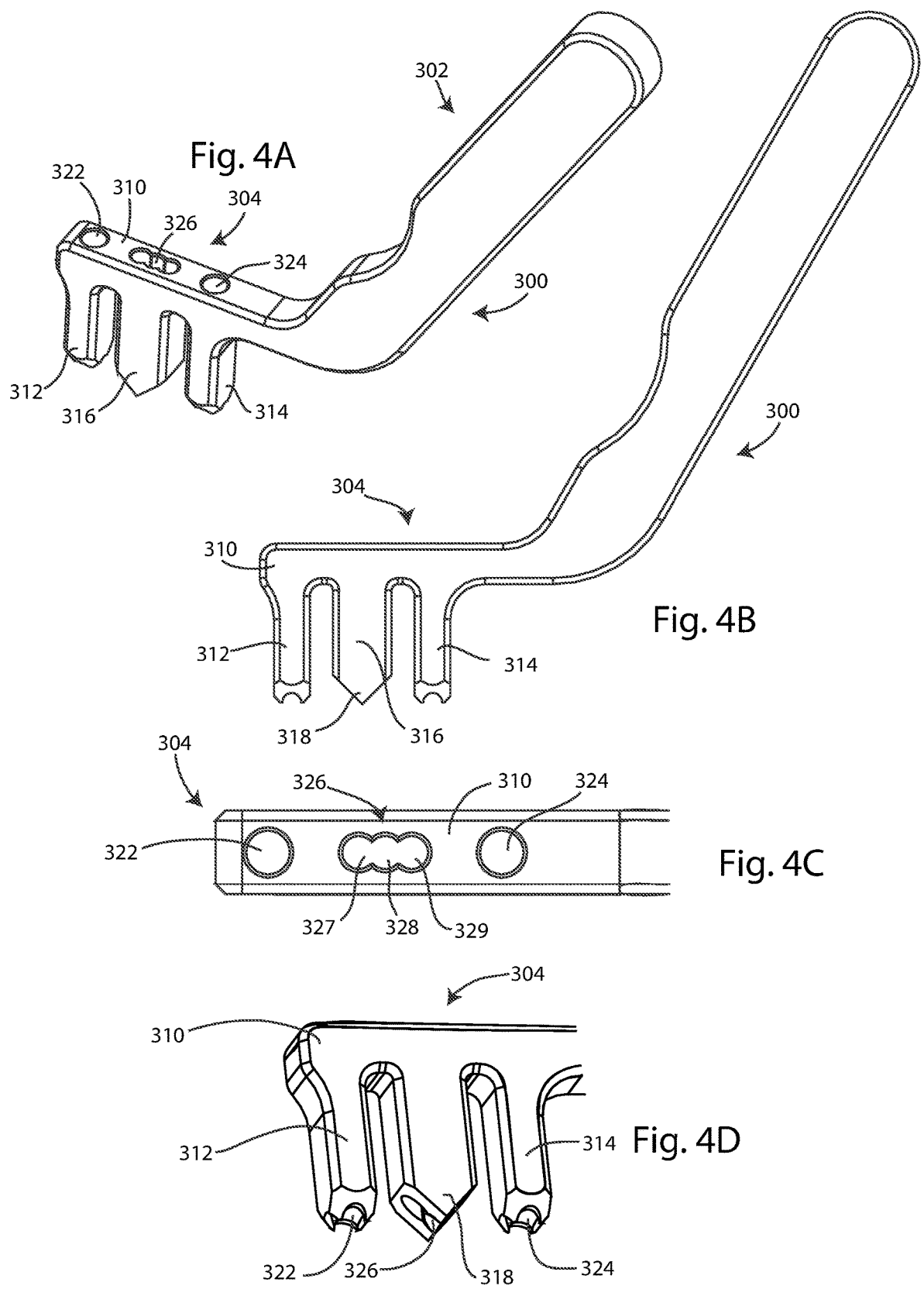

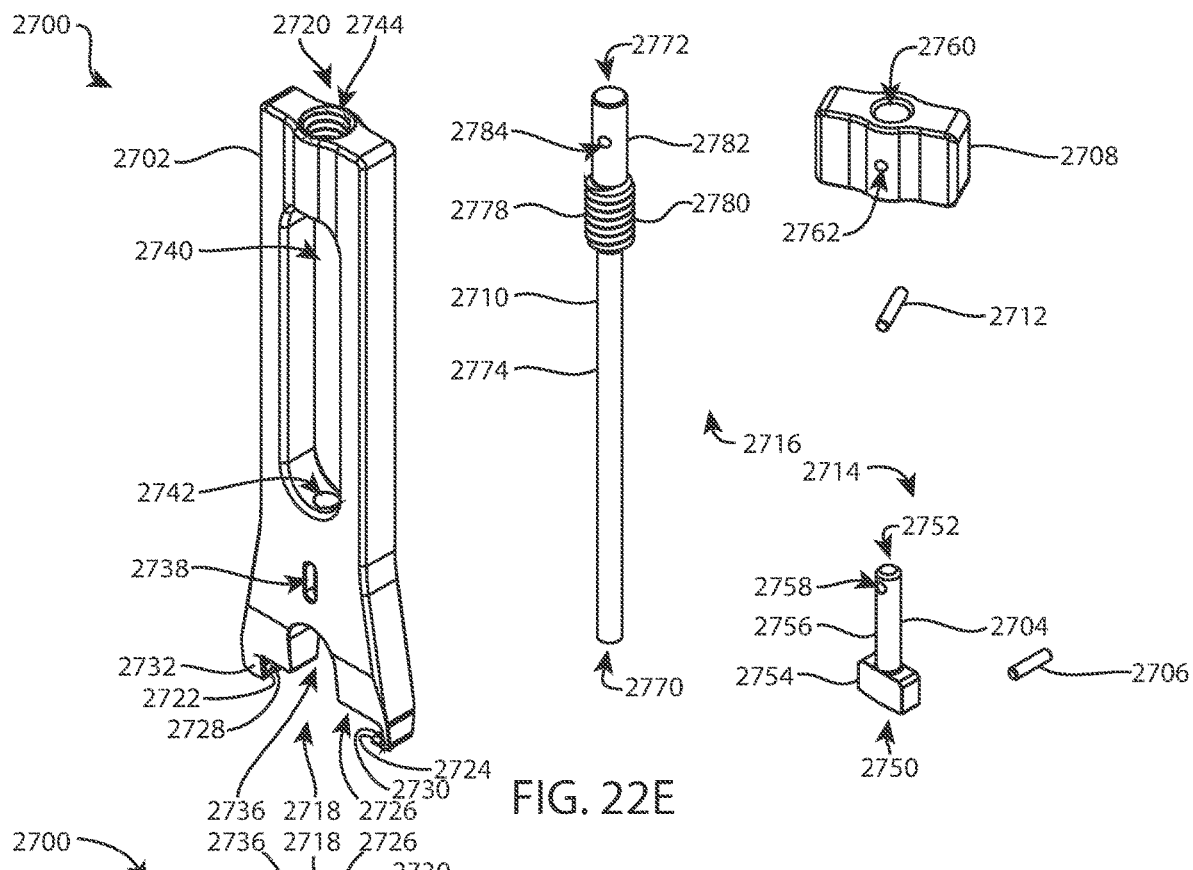
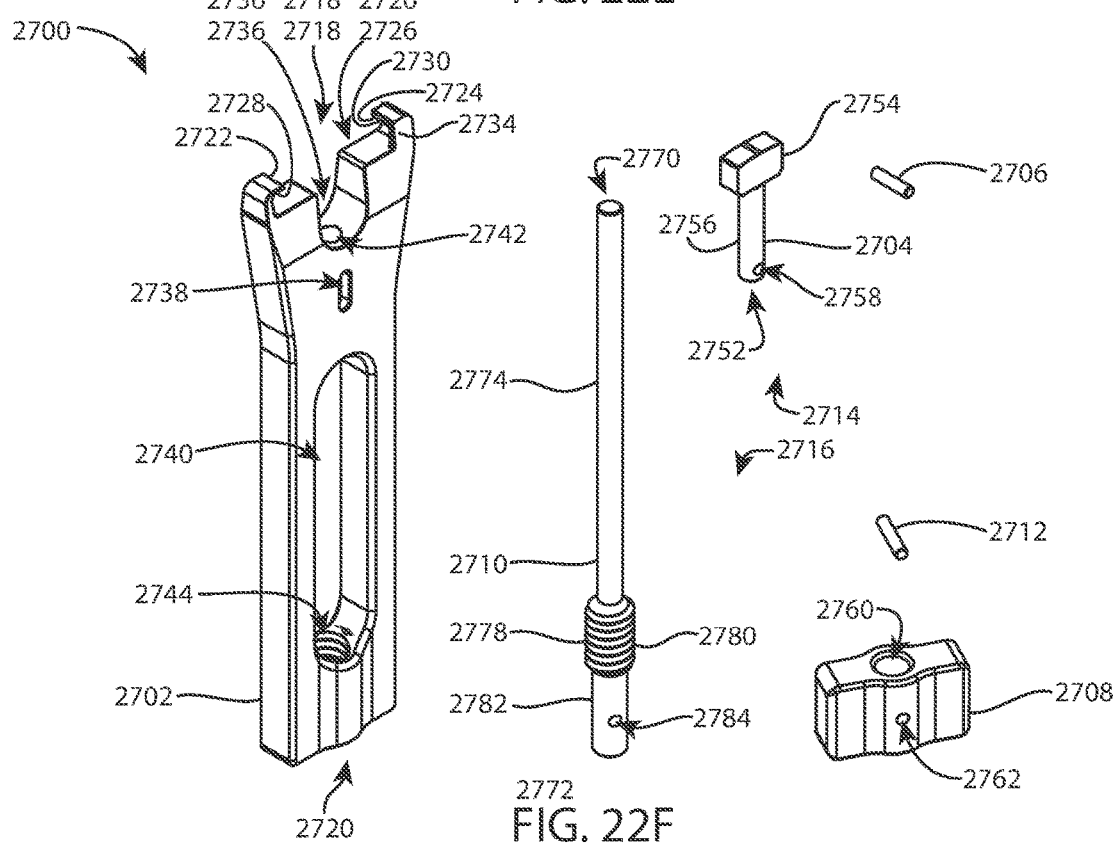

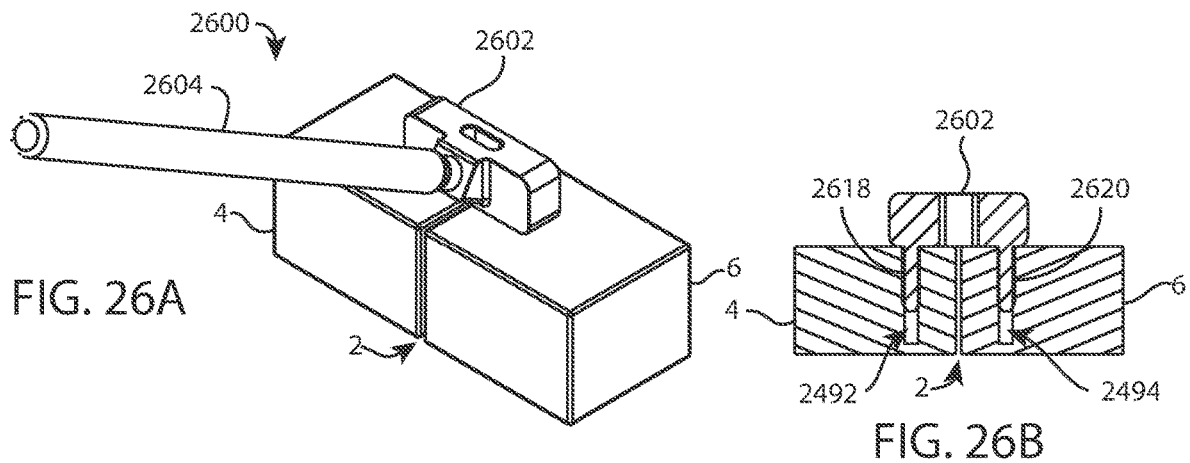
FIG. 26A
FIG. 26B
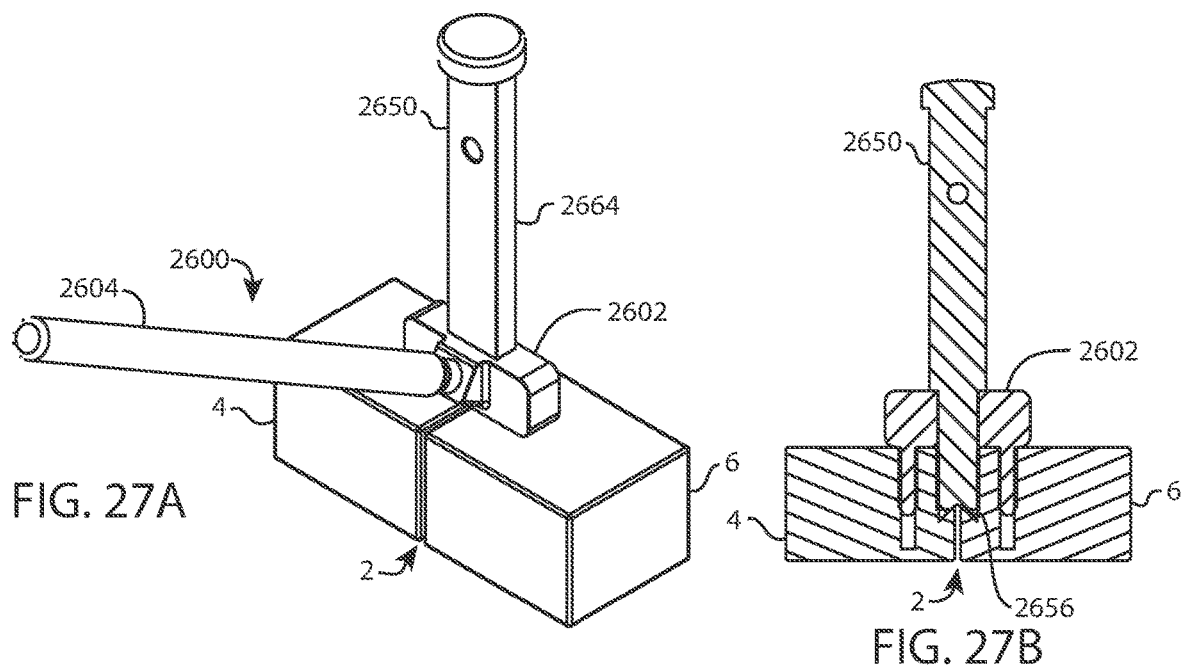
FIG. 27A
FIG. 27B
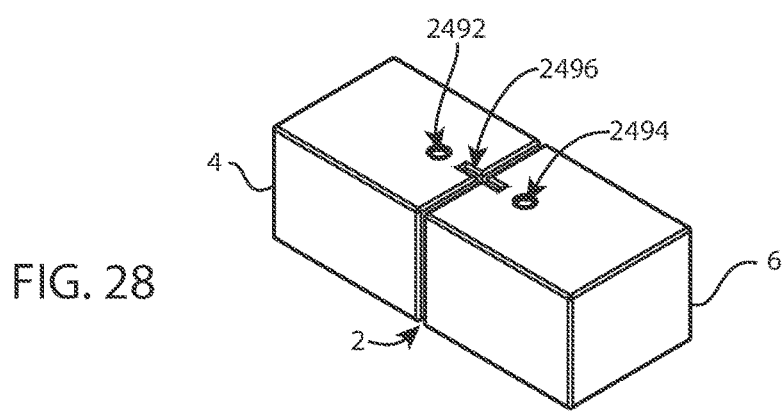
FIG. 28

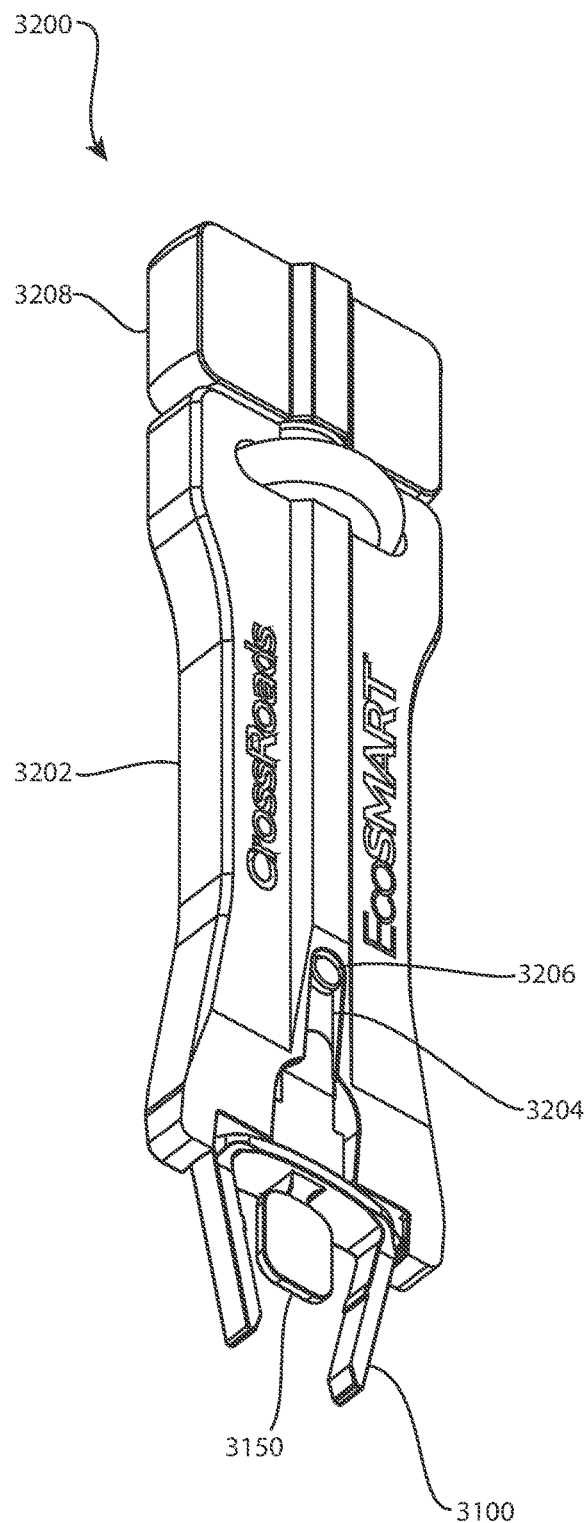
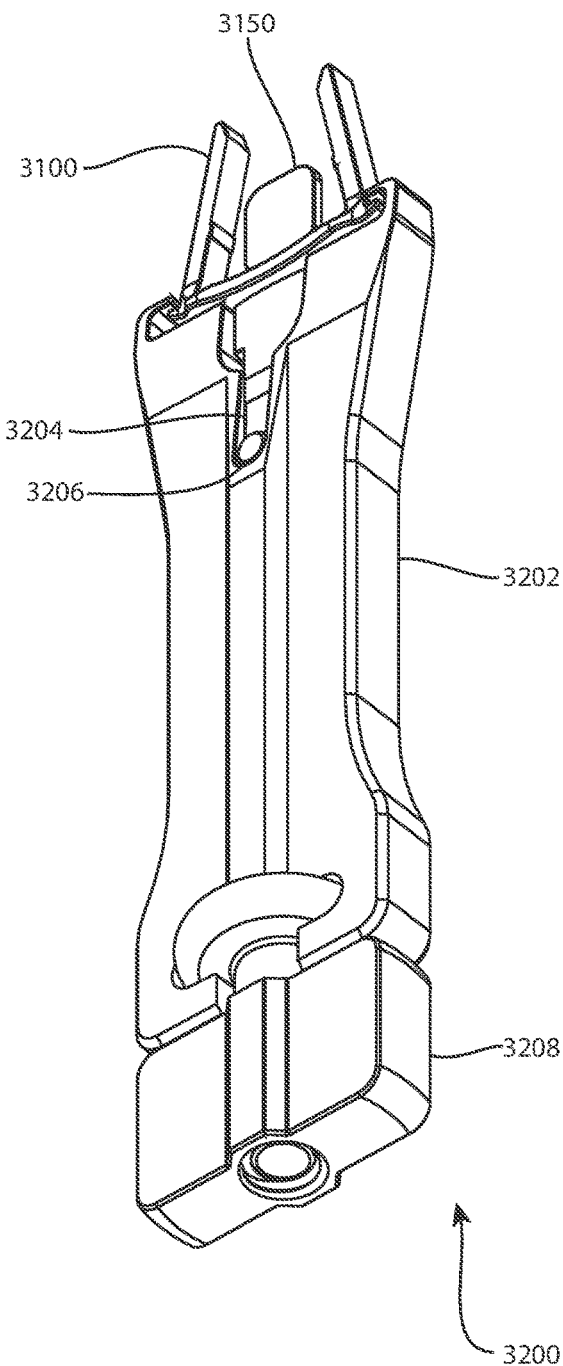
FIG. 35
FIG. 36

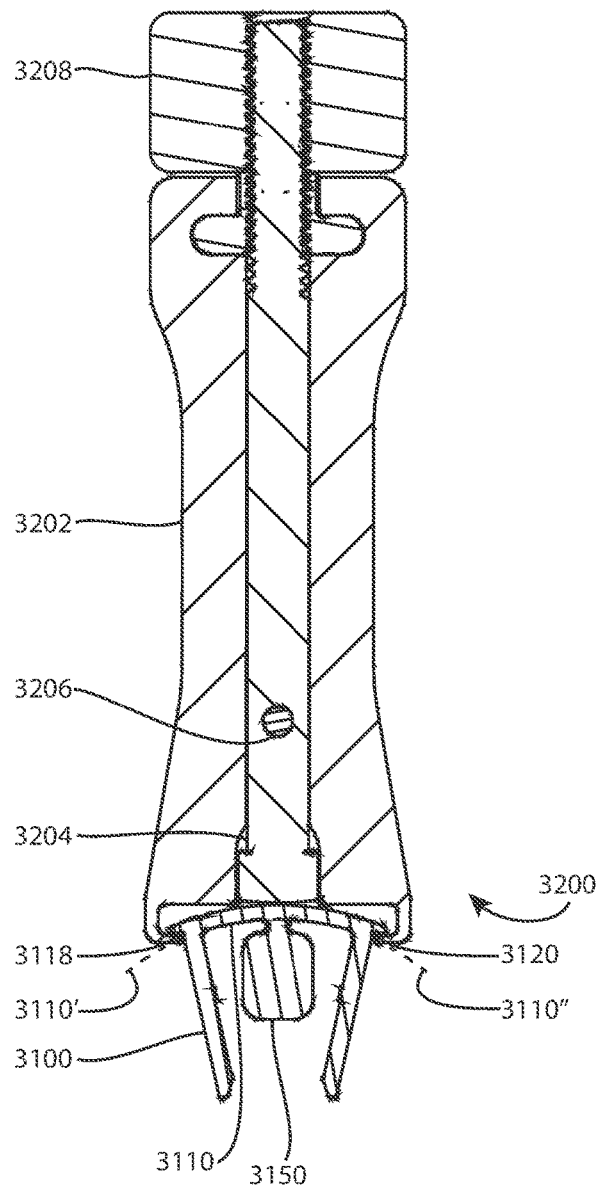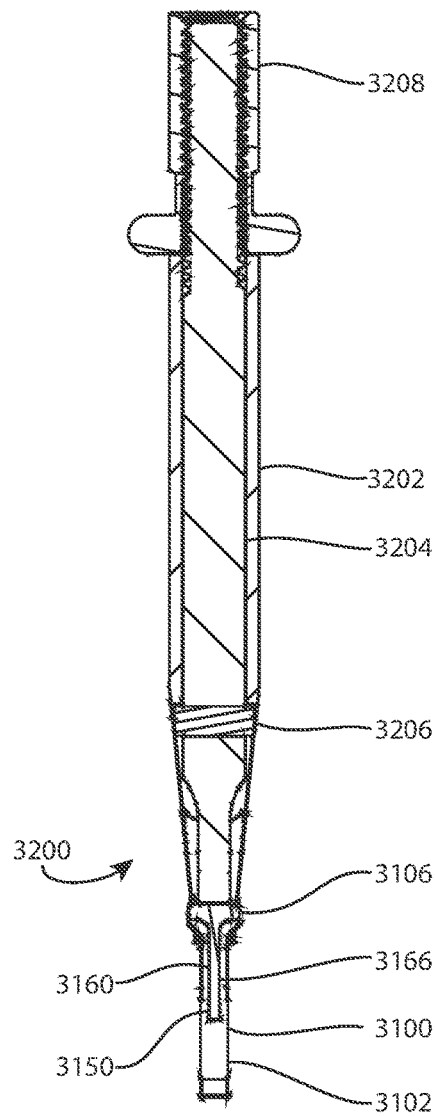
FIG. 41
FIG. 42

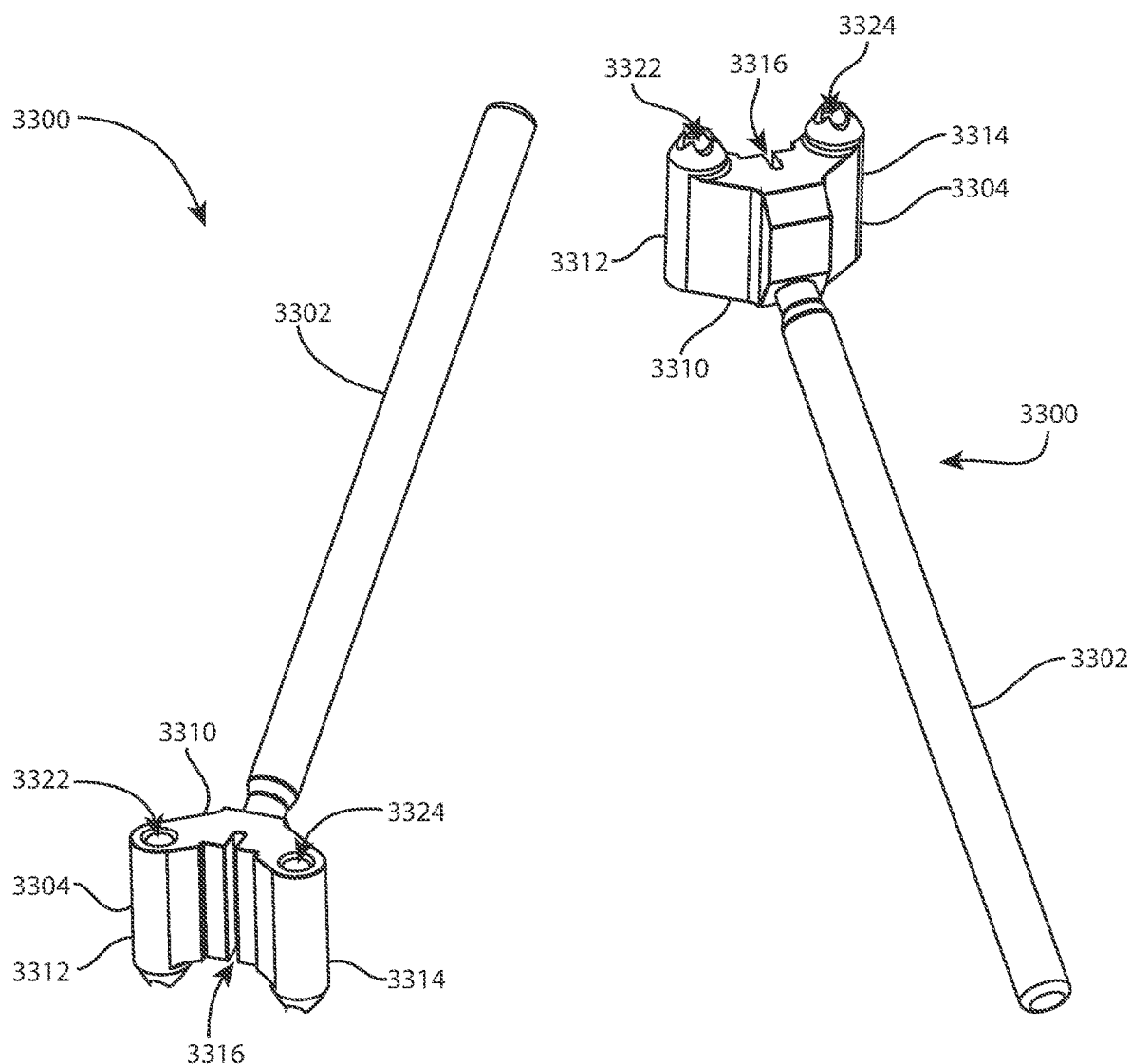
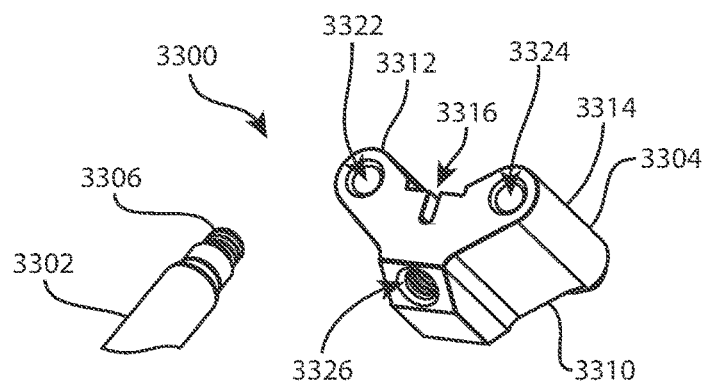
FIG. 43  FIG. 44
FIG. 45

COUNTER-TORQUE IMPLANT

CROSS-REFERENCE TO RELATED APPLICATIONS

The present application is a continuation-in-part of:

International Patent Application No. PCT/US2018/017229, filed Feb. 7, 2018, entitled COUNTER-TORQUE IMPLANT.

International Patent Application No. PCT/US2018/017229 claims priority to:

U.S. Provisional Patent Application No. 62/455,754, filed Feb. 7, 2017, entitled COUNTER-TORQUE IMPLANT, and U.S. Provisional Patent Application No. 62/456,098, filed Feb. 7, 2017, entitled COUNTER-TORQUE IMPLANT.

The foregoing are incorporated by reference as though set forth herein in their entirety.

The present application incorporates the following by reference as though set forth herein in their entirety:

U.S. patent application Ser. No. 15/209,623, filed Jul. 13, 2016, entitled BONE PLATES WITH DYNAMIC ELEMENTS.

U.S. patent application Ser. No. 15/209,623 claims the benefit of:

U.S. Provisional Application No. 62/192,059, filed Jul. 13, 2015, entitled BONE PLATES WITH DYNAMIC ELEMENTS.

U.S. patent application Ser. No. 15/209,623 is a continuation-in-part of:

International Patent Application No. PCT/US2014/070495, filed Dec. 16, 2014, entitled POLYAXIAL LOCKING HOLE.

International Patent Application No. PCT/US2014/070495 claims the benefit of:

U.S. Provisional Patent Application No. 61/919,069, filed Dec. 20, 2013, entitled POLYAXIAL LOCKING HOLE.

U.S. patent application Ser. No. 15/209,623 is a continuation-in-part of:

International Patent Application No. PCT/US2015/039551, filed Jul. 8, 2015, entitled BONE IMPLANT AND MEANS OF INSERTION.

International Patent Application No. PCT/US2015/039551 claims the benefit of:

U.S. Provisional Patent Application No. 62/022,811, filed Jul. 10, 2014, entitled BONE IMPLANT AND MEANS OF INSERTION.

U.S. patent application Ser. No. 15/209,623 is a continuation-in-part of:

International Patent Application No. PCT/US2015/039556, filed Jul. 8, 2015, entitled BONE IMPLANT WITH ANTI-ROTATION.

International Patent Application No. PCT/US2015/039556 claims the benefit of:

U.S. Provisional Patent Application No. 62/022,811, filed Jul. 10, 2014, entitled BONE IMPLANT AND MEANS OF INSERTION; and U.S. Provisional Patent Application No. 62/036,240, filed Aug. 12, 2014, entitled BONE IMPLANT WITH ANTI-ROTATION.

TECHNICAL FIELD

Implants for joint or bone fusion, and instrumentation for preparing a joint or bones to receive an implant are disclosed. The implants disclosed may be used to compress and/or provide torsional stability to a joint, osteotomy, fracture, or interface between two bodies, at least two bones, at least two bone portions, or at least two objects. The implants disclosed may be used in joint fusion procedures, fracture repair, osteotomies, or other situations where is it desirable to compress and/or provide rotational stability to two tissue portions. Each implant may also be referred to as a bone staple, clip, plate, fastener, and/or plug, and may include one or more integrated anti-torque features.

The disclosed technology includes an implant element, a plug, that is implanted in the joint or interface so that a portion of the implant element protrudes into each bone fragment. The plug resists forces such as shear and rotation at the joint or interface. The plug may be a stand alone implant or it may be combined with other implant elements, such as staples, plates, and the like. When combined, the plug may be a separate part or integrally formed with the other implant element(s). The plug does not interfere with dynamic compression provided by a staple because it is not restrained in the plane of compression, and in some examples, it may lie out of the plane of compression.

BACKGROUND

Successful bone fusion relies upon stable initial fixation of two or more bone fragments or pieces. Until fusion is achieved, one or more implants must stabilize the bone fragments against relative translation and/or rotation in response to forces acting across the joint or interface between the bone fragments.

SUMMARY

The various systems and methods of the present technology have been developed in response to the present state of the art, and in particular, in response to the problems and needs in the art that have not yet been fully solved by currently available implants or clips and corresponding instrument systems. The systems and methods of the present technology may provide enhanced rotational stability across a joint, osteotomy, fracture, or other interface between two bone portions.

To achieve the foregoing, and in accordance with the technology as embodied and broadly described herein, in an aspect of the technology, a system for stabilizing a first bone relative to a second bone, wherein a joint separates the first and second bones, the system includes: a dynamic implant having first and second legs connected by a bridge, and having a plug extending from a bone-facing side of the bridge, wherein the plug has a cross-section that is elongated along a direction parallel to a line extending between the first and second legs, wherein the implant has a free state in which the legs converge as they extend away from the bridge, and an elastically deformed state in which the legs are substantially parallel; and a drill guide having first and second lumens corresponding to the first and second legs of the implant, and having a slot corresponding to the center of the plug.

Embodiments of this aspect of the technology may further include a punch guide having first and second pegs corresponding to the first and second legs of the implant and the first and second lumens of the drill guide, and having a slot corresponding to the cross-section of the plug; and a punch having a cutting portion that has a cross-section that corresponds to the cross-section of the plug and the punch guide slot.

Another aspect of the technology is a method of stabilizing a first bone relative to a second bone, wherein a joint separates the first and second bones, the method having the steps of:

preparing a first hole in the first bone guided by a drill guide; preparing a second hole in the second bone guided by the drill guide; providing a punch guide having an elongated slot and first and second pegs; inserting the first peg of the punch guide into the first hole in the first bone and inserting the second peg of the punch guide into the second hole in the second bone, so that the elongated slot of the punch guide extends across the joint; preparing a slot in the first and second bones guided by the punch guide; providing an implant having an elongated bridge extending between opposite first and second ends, a first leg extending transversely from the first end of the bridge, a second leg extending transversely from the second end of the bridge, and a plug extending transversely from the bridge, wherein the plug has a cross-section that is elongated along a direction parallel to a plane established by the bridge, the first leg, and the second leg; implanting the implant across the joint and in the first and second bones so that the first leg of the implant is in the first hole, the second leg of the implant is in the second hole, the bridge of the implant extends across the joint between the first and second legs, and the plug of the implant is in the slot in the first and second bones.

Yet another aspect of the technology is a bone plate system, having: a bone plate having a bone-facing side, an opposite obverse side, first and second receiver holes each extending through the plate between the bone-facing and obverse sides, first and second fastener holes each extending through the plate between the bone-facing and obverse sides, and a plug extending outwardly from the bone-facing side and having a cross-section that is elongated along a direction parallel to a line extending between the first and second receiver hole centers or a line extending between the first and second fastener hole centers; and a compression bone staple having first and second legs connected by a bridge, wherein the staple has a free state in which the legs converge as they extend away from the bridge, and an elastically deformed state in which the legs are substantially parallel; wherein the staple is coupled to the plate so that the first and second legs extend through the first and second receiver holes and protrude beyond the bone-facing side.

Yet another aspect of the technology is a method of stabilizing a first bone relative to a second bone, wherein a joint separates the first and second bones, the method having the steps of: providing a bone plate having a bone-facing side, an opposite obverse side, first and second receiver holes each extending through the plate between the bone-facing and obverse sides, first and second fastener holes each extending through the plate between the bone-facing and obverse sides, and a plug extending outwardly from the bone-facing side and having a cross-section that is elongated along a direction parallel to a line extending between the first and second receiver hole centers or a line extending between the first and second fastener hole centers; providing a compression bone staple having first and second legs connected by a bridge, wherein the staple has a free state in which the legs converge as they extend away from the bridge, and an elastically deformed state in which the legs are substantially parallel; preparing a slot across the joint, wherein the slot has a cross-section that is elongated along a slot direction that is transverse to the joint; preparing a first hole in the first bone and a second hole in the second bone, wherein the first and second holes are centered on a line that is substantially parallel to the slot direction; placing a bone-facing side of a bone plate against the first and second bones; inserting a plug of the plate into the slot, wherein the plug extends outwardly from the bone-facing side and has a cross-section that is elongated complementary to the slot; placing first and second receiver holes of the plate over the first hole in the first bone and the second hole in the second bone; and inserting first and second legs of a compression bone staple through the first and second receiver holes and into the first hole in the first bone and the second hole in the second bone.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 1A is an isometric view of an implant comprising a compression bone staple and an independent plug with the staple in a relaxed state; FIG. 1B is a front view of the implant with the staple in an elastically deformed state; and FIG. 1C is a front view of the implant with the staple in the relaxed state;

FIG. 2A is a front view of the staple of FIG. 1A in the relaxed state; and FIG. 2B is an isometric view of the staple of FIG. 1A in the relaxed state;

FIG. 3A is an isometric view of the plug of FIG. 1A; FIG. 3B is a front view of the plug of FIG. 1A; FIG. 3C is a side view of the plug of FIG. 1A, the plug rotated 90° with respect to FIG. 3B; and FIG. 3D is an isometric view of an alternative embodiment of a plug;

FIG. 4A is an isometric view of a drill guide for use with the implant of FIG. 1A; FIG. 4B is a front view of the drill guide of FIG. 4A; FIG. 4C is a top detail view of a guide portion of the drill guide of FIG. 4A; and FIG. 4D is an isometric detail view of the guide portion of the drill guide of FIG. 4A;

FIG. 22E is an exploded isometric view of the implant inserter of FIG. 22A; and FIG. 22F is another exploded isometric view of the implant inserter of FIG. 22A from a different direction;

FIG. 26A is an isometric view of the joint of FIG. 25 with the assembled punch guide of FIG. 20A engaged in the holes in the first and second bone portions; and FIG. 26B is a cross-sectional view through the punch guide and bone portions of FIG. 26A;

FIG. 27A is an isometric view of the joint and punch guide of FIG. 26 with the punch of FIG. 21A inserted through the punch guide; and FIG. 27B is a cross-sectional view through the punch, punch guide, and bone portions of FIG. 27A;

FIG. 28 is an isometric view of the joint of FIG. 27 with a slot punched into the first and second bone portions and extending across the joint;

FIG. 35 is a perspective view of the compression bone staple and inserter of FIG. 34;

FIG. 36 is another perspective view of the compression bone staple and inserter of FIG. 35 from a different direction;

FIG. 41 is a cross-sectional view of the compression bone staple and inserter of FIG. 35, taken along section line 41-41 of FIG. 40;

FIG. 42 is a cross-sectional view of the compression bone staple and inserter of FIG. 35, taken along section line 42-42 of FIG. 39;

FIG. 43 is a perspective view of the drill guide assembly of FIG. 34;

FIG. 44 is another perspective view of the drill guide assembly of FIG. 43 from a different direction;

FIG. 45 is a perspective exploded detail view of a portion of the drill guide assembly of FIG. 43;

DETAILED DESCRIPTION

Figure 5A:
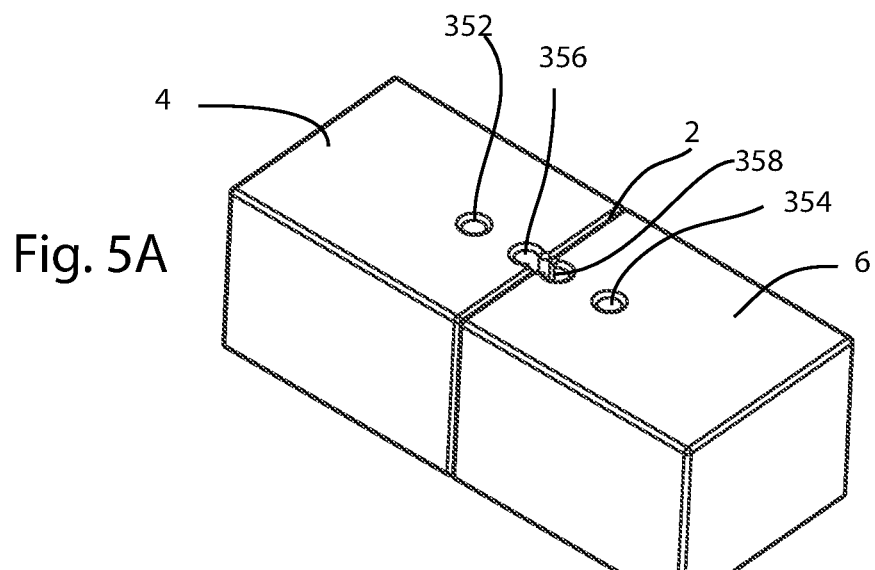
FIG. 5A is an isometric view of a joint between a first bone portion and a second bone portion, and pilot holes drilled into the joint and bone portions.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

In this specification, "substantially" means ±20% for linear dimensions and ±20° for angular dimensions.

In this specification, the terms "keel" and "plug" are used interchangeably to refer to a feature that extends into or across a joint or other interface between two bone portions.

Referring to FIGS. 1A-1C and 5C, an implant 100 includes a plug 150 and a clip 200. It is appreciated that the plug 150 and clip 200 may be used together as implant 100; however, each may also be used independently. One or more implants 100, clips 200, and/or plugs 150 may be implanted in a single procedure, for example to join two bone portions together.

Referring to FIGS. 2A and 2B, the clip 200 includes bone engaging members 202 and 204 which may be integral to a clip bridge 206, also referred to as a clip body. The bone engaging members 202 and 204 may be referred to as legs or fixation elements. In other embodiments within the scope of the disclosure, a clip may include more than two bone engaging members; or alternatively may include openings for one or more independent fasteners in lieu of integrated bone engaging members. The bone engaging member 202 extends from a left end 230 of the clip bridge 206 and the bone engaging member 204 extends from an opposite right end 232 of the clip bridge 206. Bone engaging member 202 has a proximal end 234 attached to the left end 230 of the clip bridge 206 and an opposite distal end 236 which is a free end. Bone engaging member 204 has a proximal end 238 attached to the right end 232 of the clip bridge 206 and an opposite distal end 240 which is a free end. Clip bridge 206 has an upper or proximal surface 208 and a lower surface 210. The lower surface 210 may be referred to as a bone facing surface or distal surface. Bone engaging member 202 extends from the lower surface 210 beside bone engaging member 204. The bone engaging members 202 and 204 may have features 212 that may improve bone purchase or improve pull out strength of the clip 200 from bone or soft tissue. The features 212 may be referred to as teeth or serrations. The features 212 are shown on facing sides of the bone engaging members 202, 204 but may be on any or all sides of the bone engaging members. The clip 200 may have projections or other connecting means 214 and 216 for connection with a means of insertion. The connecting means 214, 216 may be referred to as tabs, ears, protrusions, wings, retainers, connection features, or retaining members. The connecting means 214 and 216 are shown extending sideways outwardly from the left and right ends 230, 232 of the bridge 206, respectively, along a longitudinal direction established by the bridge. In other embodiments, the connecting means may project perpendicularly with respect to the bridge. The connecting means 214 and 216 may have lower surfaces 218 and 220 respectively that may releasably engage with a means of insertion that may allow an inserter or other means of insertion to be side loading, top loading or pivotably loaded. For example, an inserter for clip 200 may be side loading or pivotably loading. The lower surfaces 218, 220 may be referred to as bone facing surfaces or distal surfaces. Referring to FIG. 2A, the lower surfaces 218, 220 are proximally spaced apart from, or proximally offset from, the lower surface 210 toward the upper surface 208. The dashed extension lines 210' and 210" in FIG. 2A show the level of the lower surface 210 versus the lower surfaces 218, 220.

A means of insertion may maintain the clip 200 in a first configuration thereby allowing a second configuration once an inserter is disassembled from the implant. The first configuration may be an elastically deformed state, for example an insertion state, as seen in FIG. 1B. The second configuration may be a free state or an implanted state, as seen in FIGS. 1A, 1C, and 2A. The means of insertion may utilize features similar to connecting means 214 and 216 in combination with other surfaces such as top surface 208. This combination of means of insertion may be used to maintain one or more features or arms or projections in a particular configuration. This combination of means of insertion may create a bending modality, such as a three point or four point bend, to maintain a specific clip device configuration or combination of configurations. A combination of surfaces and means of insertion, such as connecting means 214, may be used on the entire clip or portions of a clip to create or maintain a particular configuration of a clip. For example, a tab such as 214 and top surface, such as 208 may be used to maintain one side of a clip or one leg of a clip in a particular configuration. When disassembled, that leg may have a configuration that is different from or the same as the configuration of the rest of the clip.

Referring to FIGS. 2A-2B, the clip 200 is shown in the free state, or relaxed state, which is the shape of the clip 200 when no external forces are acting upon the clip 200, other than gravity; the clip 200 experiences no elastic or plastic deflection or deformation. In the free state, the bone engaging members 202 and 204 converge as they extend away from the bridge 206 so that the distal ends 236, 240 are closer together than are the proximal ends 234, 238. An angle 222 is formed between the converging bone engaging members 202 and 204 in the free state. The angle 222 opens toward the bridge 206. The angle 222 may be referred to as a free state angle.

Referring to FIGS. 1A-1C and 3A-3C, plug 150 extends between a proximal or first end 154 and a distal or second end 156, along a longitudinal axis 158. A plug head 160 is at the first end 154, separated from a plug tip 162 by a plug body 152. The plug head 160 may include a slot or channel 164 shaped to complementarily receive the clip bridge 206, the channel flanked by opposing first and second rails 166, 168. From a superior or top down perspective, the plug head 160 may have a circular perimeter, whereas the body 152 is generally rectangular in cross-section, in order to prevent rotation of the plug 150 once inserted. The thickness of the body 152, perpendicular to the slot 164, may be the same as or similar to the thickness of the bridge 206 and/or bone engaging members 202, 204 of the clip 200 in the same direction (front-back), or the body 152 may be thicker or thinner than the clip 200. Preferably, the body 152 is thinner than the bone engaging members 202, 204. The plug tip 162 is tapered to facilitate insertion into bone. One or more sides of the plug body 152 and/or tip 162 may include features 170 that may improve bone purchase. The features 170 may be referred to as teeth or serrations. The features 170 are shown on opposing sides of the plug body 152 and tip 162, but may be on any or all sides. In an embodiment, features 170 may be absent. In other embodiments, the cross-sectional shape of the body may be rectangular, triangular, round, double-barrel or another shape.

Referring to FIGS. 4A-4D, a drill guide 300 may be employed to prepare pilot holes for implant 200 in a joint 2 between a first bone 4 and a second bone 6. The joint 2 may be an actual anatomical joint, an osteotomy, a fracture, or an interface between the first and second bones 4, 6. Drill guide BOO may include a handle portion 302 and a guide portion 304; some embodiments may exclude the handle portion 302. The guide portion 304 includes a guide bar 310 from which one or more guide elements may depend. In the embodiment depicted, guide portion 304 includes first and second single hole guide elements 312, 314 which flank a multi-hole guide element 316. Of course, other embodiment of the drill guide 300 can include any number and arrangement of guide elements; and in other embodiments the guide elements may not depend from the guide bar. Guide element 312 surrounds and supports a first lumen 322; guide element 314 surrounds and supports a second lumen 324, and guide element 316 surrounds and supports a third lumen 326. All the guide elements may include pointed or tapered tips to facilitate engagement with bone or tissues during the drilling procedure. Guide element 316 includes a wedge 318 which may be aligned with a joint 2 to control placement of the pilot holes with respect to the joint 2, during a drilling procedure.

In the embodiment depicted, the first and second lumens 322, 324 are circular in a transverse cross section, and each are shaped to guide a drill for drilling a single bore. The third lumen 326 includes three overlapping lumens 327, 328, 329. In a transverse cross section, the third lumen 326 has the shape of three overlapping circles, which may be called a "snowman shape." The elongated transverse shape of the third lumen 326 allows a single drill to be used to create a pilot hole large enough to receive the plug 150. In other embodiments, the third lumen may have an oval, circular, figure eight, rectangular, or other shape cross-sectional shape which provides a line to line or interference fit between the lumen and the plug upon insertion of the plug. In the embodiment shown, the first, second and third lumens 322, 324, 326 are co-planar. In other embodiments, one or more of the lumens may be out of the plane of the others.

Referring to FIGS. 4A-5C, a method of insertion of implant 100 is described. Drill guide 300 is positioned adjacent the first and second bone portions 4, 6, with guide portion 304 spanning the joint 302. The guide portion 304 may be impacted, with wedge 318 positioned in joint 2. Wedge 318 may be pressed, impacted or otherwise aligned into the joint 2, to ensure proper alignment of the drill guide with respect to the joint 2, and may ensure that the pilot holes are centered with respect to the joint line. Pilot holes 352, 354, and 356 are drilled into the bone portions 4, 6 and joint 2. Residual material 358, which may be in the form of ridges, may be left in pilot hole 356. This residual material may create interference for the plug 150 providing a tight fit of the plug in the pilot hole 356.

Figure 5B:
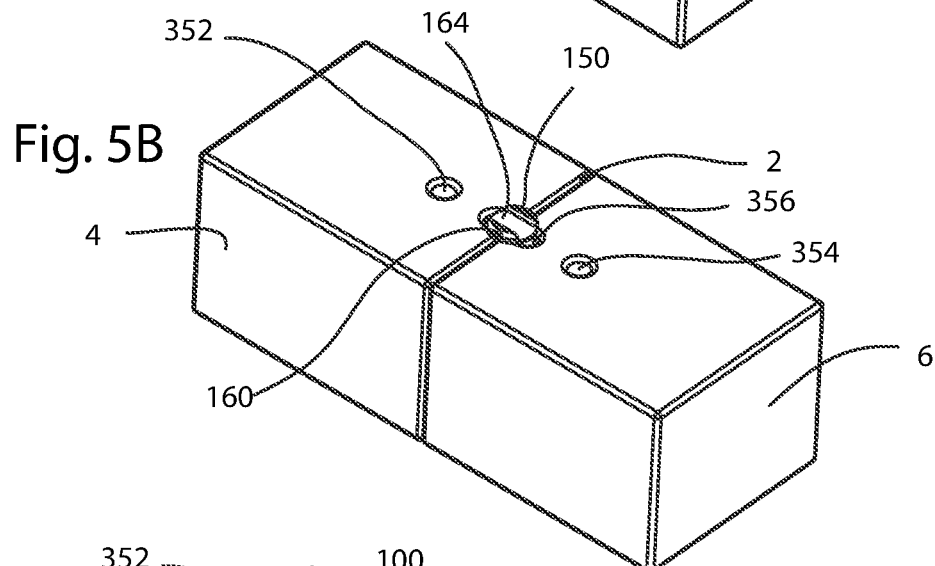
FIG. 5B is an isometric view of the joint of FIG. 5A with the plug of FIG. 1A inserted into the joint.
Figure 5C:
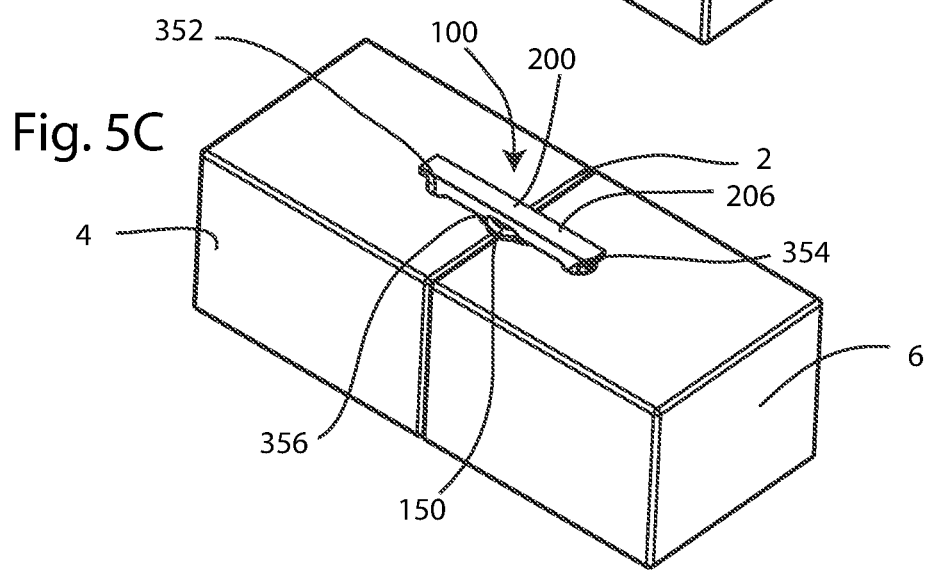
FIG. 5C is an isometric view of the joint of FIG. 5A with the plug and clip of FIG. 1A inserted into the pilot holes.

Referring to FIG. 5B, plug 150 is inserted into the pilot hole 356 and in contact with bone portions 4, 6. Thus positioned in the joint, the plug provides stability to the joint, and provides resistance to forces acting on the joint, including shear and rotational forces. Head 160 of the plug is oriented so that channel 164 is approximately perpendicular to the joint 2, and is aligned in the same plane with outboard pilot holes 352, 354. Referring to FIG. 5C, clip 200 is inserted with bridge 206 approximately perpendicular to the joint 2. During the insertion procedure, a means of insertion such as an instrument may flex clip 200 toward the insertion state to urge leg distal ends 236, 240 away from one another. Bone engaging member 202 is inserted in pilot hole 352, and bone engaging member 204 is inserted in pilot hole 354. Clip bridge 206 is received in channel 164, preventing rotation of the clip 200 once inserted, and preventing rotation of the bone portions 4, 6 relative to one another.

Figure 8A:
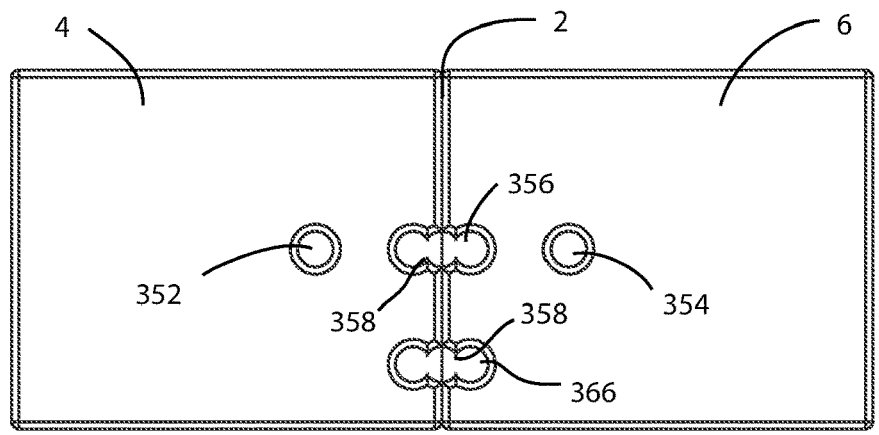
FIG. 8A is a top view of a joint between a first bone portion and a second bone portion, and pilot holes drilled into the joint and bone portions.
Figure 8B:
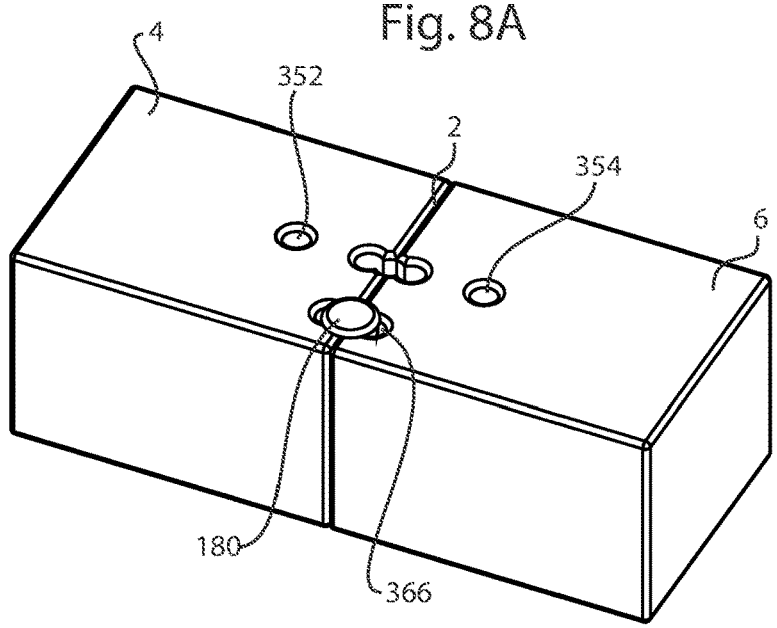
FIG. 8B is an isometric view of the joint of FIG. 8A, with the plug of FIG. 3D implanted in the joint.
Figure 8C:
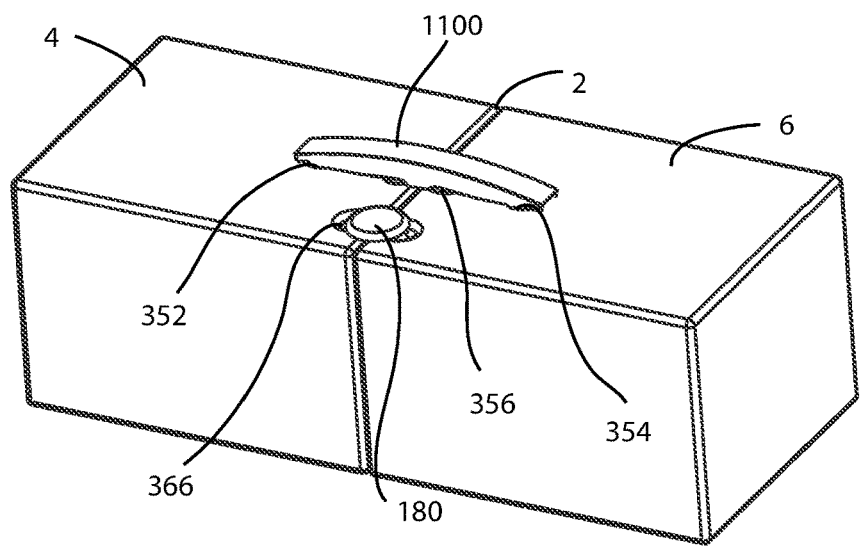
FIG. 8C is an isometric view of the joint of FIG. 8A with the implant of FIG. 6A and the independent anti-torque plug of FIG. 3D inserted into the joint.

In an alternative embodiment shown in FIG. 3D, a plug 180 includes a head 190 which lacks a channel. When implant into a joint as described above, plug 180 may be offset from the plane of corresponding implant 200, as shown in FIGS. 8B and 8C. Drill guide 300 may be used to prepare an offset pilot hole 366. Plug 180 may be implanted independently as a stand-alone implant, or may be implanted with a staple such as clip 200 or others disclosed herein. In another embodiment, plug 150 may be implanted to be offset from the plane of clip 200. Whether implanted independently into a joint, or with a clip 200, the plug 180 may provide torsional stability, preventing rotation of the bone portions 4, 6 relative to one another, and/or preventing shear forces from acting upon the joint.

In other embodiments within the scope of the disclosure, plug 150 may be implanted with another corresponding implant such as a bone plate. The plug and bone plate combination may be implanted across a joint between two bones, bodies or devices to resist rotation of the bodies about the joint. The bone plate may have two or more openings for fasteners, and a feature to cooperatively connect with plug 150.

Figure 6A:
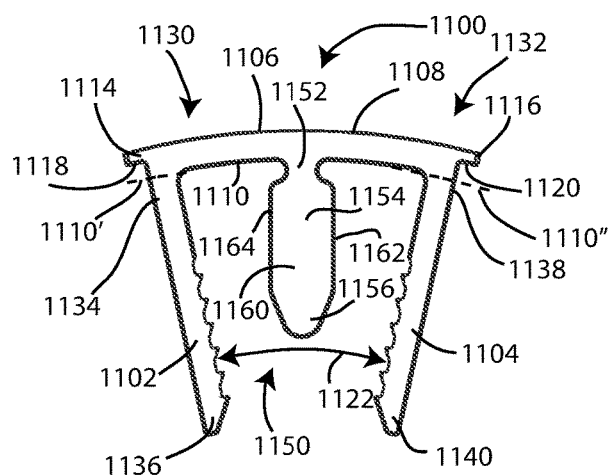
FIG. 6A is a front view of an implant comprising a compression bone staple having an integrated anti-torque plug with the staple in a relaxed state.
Figure 6B:
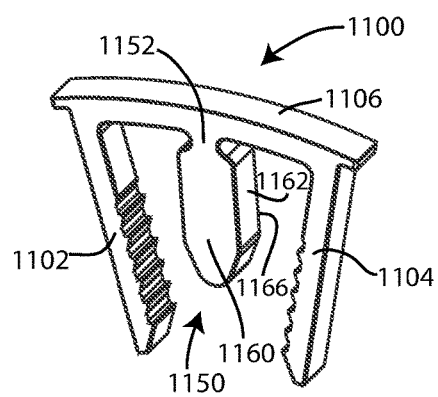
FIG. 6B is an isometric view of the implant of FIG. 6A.
Figure 6C:
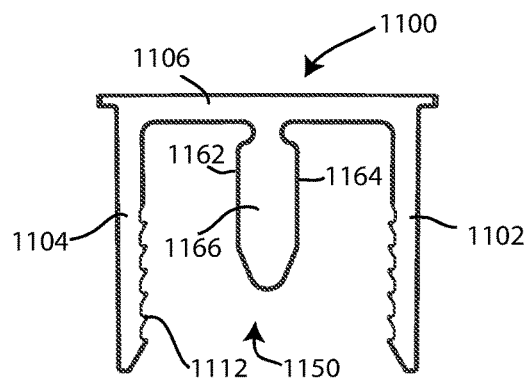
FIG. 6C is a back view of the implant of FIG. 6A with the staple in an elastically deformed state.
Figure 7A:
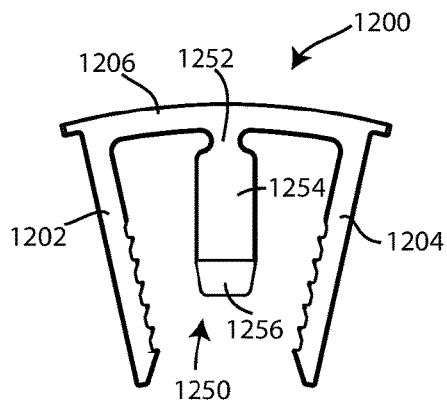
FIG. 7A is a front view of another embodiment of an implant comprising a compression bone staple and an integrated anti-torque plug with the staple in a relaxed state.
Figure 7B:
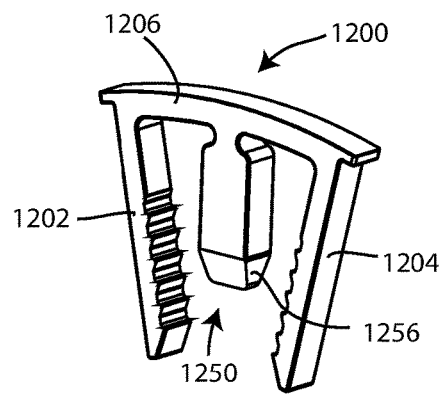
FIG. 7B is an isometric view of the staple of FIG. 7A.

Referring to FIGS. 6A-6C, a clip 1100 includes an integrated anti-torque plug 1150. Clip 1100 and other clips disclosed herein may also be referred to as a fastener, staple, or implant. Anti-torque plug 1150 and other anti-torque features disclosed herein may also be referred to as a tab, keel, post, or implant. FIGS. 7A-7B show an alternate embodiment of an implant; clip 1200 includes an integrated anti-torque plug 1250 which has a chisel-shaped tip. FIG. 3D shows an independent anti-torque plug 180. One or more clips 1100, 1200, plates and/or plugs 180 disclosed herein may be implanted in a single procedure, for example to join two bone portions together.

Referring to FIGS. 6A and 6B, the clip 1100 includes bone engaging members 1102 and 1104 which may be integral to a clip bridge 1106, also referred to as a clip body. The bone engaging members 1102 and 1104 may be referred to as legs. In other embodiments within the scope of the disclosure, a clip may include more than two bone engaging members; or alternatively may include openings for one or more independent fasteners in lieu of the bone engaging members. In other embodiments of the disclosure, the implant 1100 may be more similar to a plate. The bone engaging member 1102 extends from a left end 1130 of the clip bridge 1106 and the bone engaging member 1104 extends from an opposite right end 1132 of the clip bridge 1106. Bone engaging member 1102 has a proximal end 1134 attached to the left end 1130 of the clip bridge 1106 and an opposite distal end 1136 which is a free end. Bone engaging member 1104 has a proximal end 1138 attached to the right end 1132 of the clip bridge 1106 and an opposite distal end 1140 which is a free end. Clip bridge 1106 has at least one upper or proximal surface 1108 and at least one lower or distal surface 1110. The lower surface 1110 may be referred to as a bone facing surface. Bone engaging member 1102 extends from the lower surface 1110 beside bone engaging member 1104. The bone engaging members 1102 and 1104 may have features 1112 that may improve bone purchase or improve pull out strength of the clip 1100 from bone or soft tissue. The features 1112 may be referred to as teeth or serrations. The features 1112 are shown on facing sides of the bone engaging members 1102, 1104 but may be on any or all sides of the bone engaging members. The clip 1100 may have projections or other connecting means 1114 and 1116 for connection with a means of insertion. The connecting means 1114, 1116 may be referred to as tabs, ears, protrusions, wings, retainers, or retaining members. The connecting means 1114 and 1116 are shown extending sideways outwardly from the left and right ends 1130, 1132 of the bridge 1106, respectively, along a longitudinal direction established by the bridge. In other embodiments, the connecting means may project perpendicularly with respect to the bridge. The connecting means 1114 and 1116 may have lower or distal surfaces 1118 and 1120 respectively that may releasably engage with a means of insertion that may allow an inserter or other means of insertion to be side loading, top loading or pivotably loaded. For example, an inserter for clip 1100 may be side loading or pivotably loading. The lower surfaces 1118, 1120 may be referred to as bone facing surfaces. Referring to FIG. 6A, the lower surfaces 1118, 1120 are proximally spaced apart from, or proximally offset from, the lower surface 1110. The dashed extension lines 1110' and 1110" in FIG. 6A show the level of the lower surface 1110 versus the lower surfaces 1118, 1120.

An integrated anti-torque plug 1150 projects distally from the lower surface 1110 of bridge 1106. In the embodiment depicted, a single plug 1150 is centered between bone engaging members 1102, 1104; in other embodiments the plug may be off-center relative to the members 1102, 1104, and/or a plurality of plugs may be included. The plug may also be connected to the implant 1100 in more than one location along the lower surface 1110 of bridge 1106. Plug 1150 includes a neck portion 1152 where the plug is joined to bridge 1106, a body 1154, and a tip 1156. Neck portion 1152 may be formed as a waist having a reduced width with respect to the plug body 1154 as shown in FIGS. 6A-6C; in other embodiments the neck portion 1152 may be wider than or equal in width with respect to the plug body 1154. Preferably, plug 1150 is connected to the clip 1100 only via the bridge 1106, and not along the bone engaging members 1102, 1104. Plug 1150 may be rectangular in cross-section and includes four sides 1160, 1162, 1164, 1166. The plug thickness between sides 1160 and 1166 may be less than, the same as, similar to, or greater than the thickness of the bridge 1106 and/or bone engaging members 1102, 1104 of the clip 1100 in the same direction (front-back). Preferably, the plug thickness between sides 1160 and 1166 is less than the thickness of the bone engaging members 1102, 1104 in the same direction. The plug tip 1156 may be tapered on at least two sides 1162, 1164 with respect to the plug body to facilitate insertion into a joint. The plug sides 1160, 1162, 1164, 1166 may be smooth as seen in FIGS. 6A-6C; in other embodiments one or more plug sides may include teeth, serrations, or other surface roughening. In other embodiments, the plug may have a differently shaped cross-section. The plug does not preclude compression of the bone segments by the bone engaging members 1102, 1104, at least because the plug is oriented in a plane coplanar with, or parallel to, the plane of the bridge 1106 and bone engaging members 1102, 1104 of the clip 1100.

A means of insertion may maintain the clip 1100 in a first configuration thereby allowing a second configuration once an inserter is disassembled from the implant. The first configuration may be an elastically deformed state, for example an insertion state, as seen in FIG. 6C. The second configuration may be a free state or an implanted state, as seen in FIGS. 6A and 6B. The means of insertion may utilize features similar to connecting means 1114 and 1116 in combination with other surfaces such as top surface 1108. This combination of means of insertion may be used to maintain one or more features or arms or projections in a particular configuration. This combination of means of insertion may create a bending modality, such as a three point or four point bend, to maintain a specific clip device configuration or combination of configurations. A combination of surfaces and means of insertion, such as connecting means 1114, may be used on the entire clip or portions of a clip to create or maintain a particular configuration of a clip. For example, a tab such as 1114 and top surface, such as 1108 may be used to maintain one side of a clip or one leg of a clip in a particular configuration. When disassembled, that leg may have a configuration that is different from or the same as the configuration of the rest of the clip.

Referring to FIGS. 6A-6B, the clip 1100 is shown in the free state, or relaxed state, which is the shape of the clip 1100 when no external forces are acting upon the clip 1100, other than gravity; the clip 1100 experiences no elastic or plastic deflection or deformation. In the free state, the bone engaging members 1102 and 1104 converge as they extend away from the bridge 1106 so that the distal ends 1136, 1140 are closer together than are the proximal ends 1134, 1138. An angle 1122 is formed between the converging bone engaging members 1102 and 1104 in the free state. The angle 1122 opens toward the bridge 1106. The angle 1122 may be referred to as a free state angle.

Referring to FIGS. 7A-7B, an alternative embodiment of an implant with an integrated anti-torque plug is shown. Clip 1200 includes a first bone-engaging member 1202, a second bone-engaging member 1204, a bridge 1206, and an integrated anti-torque plug 1250. The descriptions of the bone engaging members, bridge and anti-torque plug of clip 1100 are applicable to clip 1200. In addition, the descriptions of the free state, the elastically deformed state, and means of insertion of clip 1100 are also applicable to clip 1200. The anti-torque plug 1250 of clip 1200 includes neck 1252 and body 1254 portions, as described for clip 1100. A tip portion 1256 of clip 1200 is tapered on all four sides with respect to the body 1254, to form a chisel or wedge shape. Other embodiments may include tip portions having other taper shapes in which one or more sides of the tip is tapered with respect to the body. In other embodiments, the taper may extend along one or more body portion sides.

Referring to FIG. 3D, an independent anti-torque plug 180 extends between a proximal or first end 182 and a distal or second end 184, along a longitudinal axis 186. A plug head 190 is at the first end 182, separated from a plug tip 188 by a plug body 192. From a superior or top down perspective, the plug head 190 may have a circular perimeter, whereas the body 192 is generally rectangular in cross-section, in order to prevent rotation of the plug 180 once inserted. The plug tip 188 is tapered to facilitate insertion into bone. One or more sides of the plug body 192 and/or tip 188 may include features 194 that may improve bone purchase. The features 194 may be referred to as teeth or serrations. The features 194 are shown on opposing sides of the plug body 192 and tip 188, but may be on any or all sides. In an embodiment, features 194 may be absent. In other embodiments, the cross-sectional shape of the body 192 may be rectangular, triangular, round, double-barrel or another shape. One or more plugs 180 may be implanted independently in a joint to prevent rotation of the bones or bodies about the joint, and/or one or more plugs 180 may be implanted in conjunction with any of the clips disclosed herein, as in FIG. 8C, to provide additional joint stability.

Referring to FIGS. 4A-4D, the drill guide BOO may be employed to prepare pilot holes for implants 180, 1100, 1200 or any implant disclosed herein, in a joint 2 between a first bone 4 and a second bone 6. The joint 2 may be an actual anatomical joint, an osteotomy, a fracture, or an interface between the first and second bones 4, 6. Drill guide BOO may be used to prepare a joint for implantation of any of the implants disclosed herein. Other instrumentation may be used to prepare a site to receive one or more of the implants described herein, including punches, drills, saws, sawblades, or any other instrument capable of creating an opening through the tissue, bone or joint material.

Referring to FIGS. 4A-4D and 8A-8C, a method of insertion of implant 1100 is described. It is understood that the method of insertion may employed for any of the implants described herein. Drill guide 300 is positioned adjacent the first and second bone portions 4, 6, with guide portion 304 spanning the joint 2. The guide portion 304 may be impacted, with wedge 318 positioned in joint 2. Wedge 318 may be pressed, impacted or otherwise aligned into the joint 2, to ensure proper alignment of the drill guide with respect to the joint 2, and may ensure that the pilot holes are centered with respect to the joint line. Pilot holes 352, 354, and 356 are drilled into the bone portions 4, 6 and joint 2. Residual material 358, which may be in the form of ridges, may be left in pilot hole 356. This residual material may create interference for the plug 1150 providing a tight fit of the plug in the pilot hole 356. If desired, another pilot hole 366 may be created for implantation of an independent anti-torque plug 180. Pilot hole 366 may be drilled in joint 2, and may be offset from pilot holes 352, 354, and 356.

Referring to FIG. 8C, clip 1100 is inserted into the pilot holes 352, 354, 356, with bridge 1106 approximately perpendicular to the joint 2. During the insertion procedure, a means of insertion such as an instrument may flex clip 1100 toward the insertion state to urge leg distal ends 1136, 1140 away from one another. Bone engaging member 1102 is inserted into pilot hole 352, bone engaging member 1104 is inserted into pilot hole 354, and plug 1150 is inserted into the joint, in pilot hole 356 and in contact with bone portions 4, 6. Thus positioned in the joint, the plug 1150 provides stability to the joint, and provides resistance to forces acting on the joint, including shear and rotational forces. Before or after insertion of clip 1100, an auxiliary independent anti-torque plug 180 may be implanted in optional pilot hole 366. The plug 180 may be oriented so that features 70 are approximately perpendicular to the joint 2, in order to provide an interference fit with any residual material in pilot hole 366. Plug 180 may be offset from the plane of the bone engaging members 1102, 1104 and plug 1150 of clip 1100.

Figure 9A:
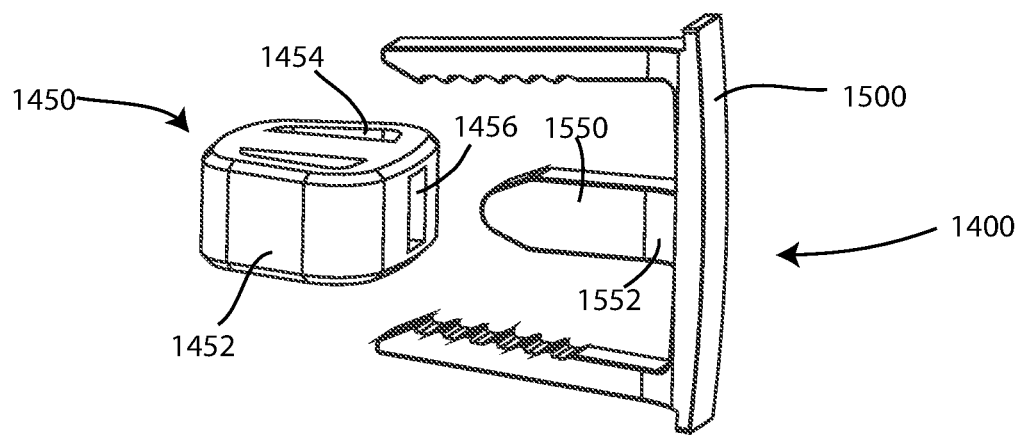
FIG. 9A is an isometric view of an implant including a clip and an interbody spacer.
Figure 9B:
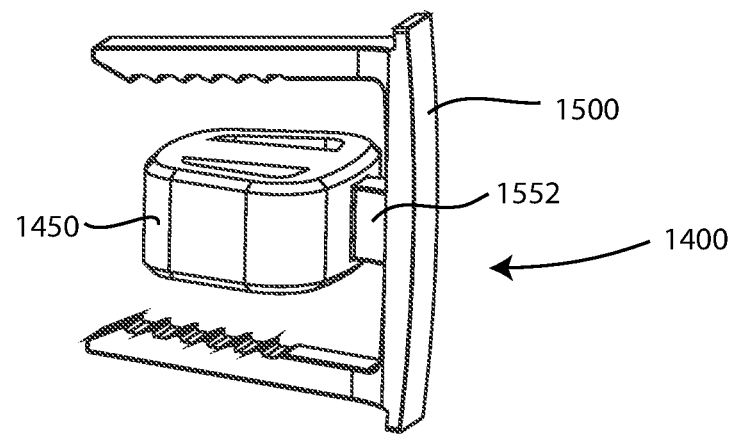
FIG. 9B is an isometric view of the implant of FIG. 9A with the clip joined to the spacer.

Clips disclosed herein may also be implanted in combination with a spacer or other interbody device. Referring to FIGS. 9A and 9B, implant 1400 includes a clip 1500 and a spacer 1450. The description of clip 1100 may apply to clip 1500, with the exception that clip 1500 includes a plug 1550 having neck portion 1552 which may be greater to or equal in width to the body of the plug. Spacer 1450 includes a body 1452, and may have one or more fenestrations 1454 for insertion of bone graft material and/or for bone in-growth. Spacer 1450 also includes a slot 1456 shaped to receive a plug such as plug 1550, and may form an interference fit with neck 1552 when joined with the plug as shown in FIG. 9B. In a method of implantation, spacer 1450 may be joined to clip 1500, and the resultant implant 1400 may be implanted as a unit. Alternately, spacer 1450 may be implanted into a prepared joint space first, and then clip 1500 may be implanted, with slot 1456 receiving plug 1550.

Figure 10A:
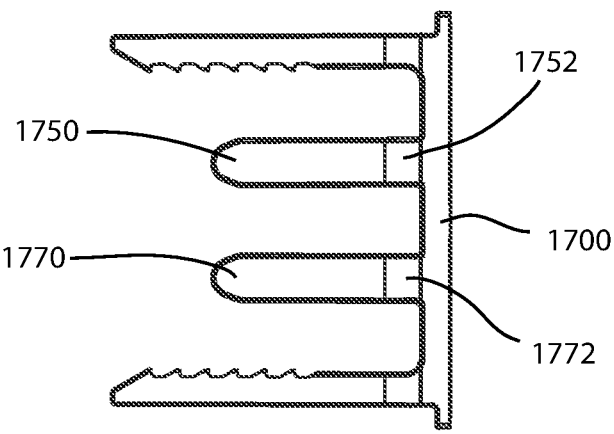
FIG. 10A is a side view of another embodiment of an implant comprising a compression bone staple and two integrated anti-torque plugs with the staple in an elastically deformed state.
Figure 10B:
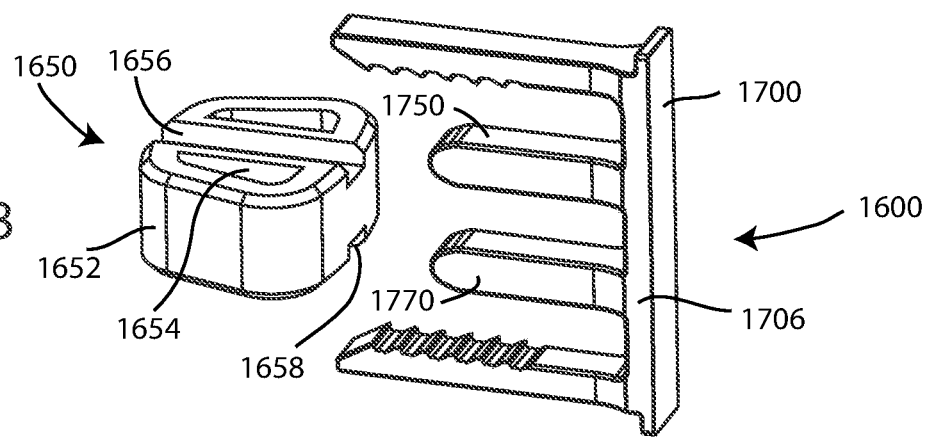
FIG. 10B is an isometric view of the implant of FIG. 10A and another interbody spacer.
Figure 10C:
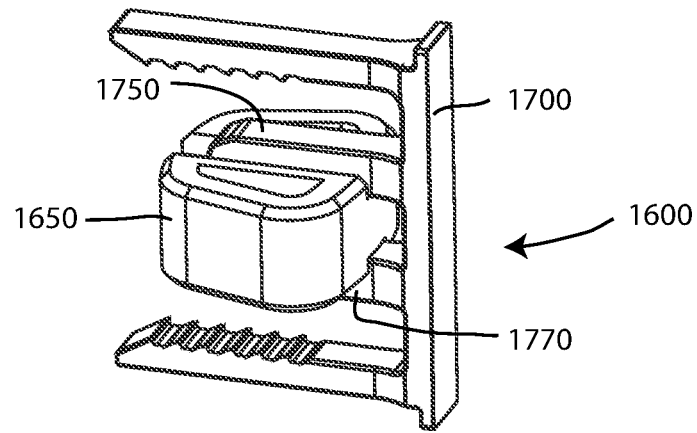
FIG. 10C is an isometric view of the interbody spacer of FIG. 10B joined to the implant of FIG. 10A.

Referring to FIGS. 10A-10C, implant 1600 includes a clip 1700 and a spacer 1650. The description of clip 1100 may apply to clip 1700, with the exception that clip 1700 includes two anti-torque plugs 1750, 1770. Each anti-torque plug 1750, 1770 may include a neck portion 1752, 1772 which may taper outward from the neck to the clip bridge 1706. Spacer 1650 includes a body 1652, and may have one or more fenestrations 1654 for insertion of bone graft material and/or for bone in-growth. Spacer 1650 also includes slots 1656, 1658 shaped to receive plugs 1750, 1770, which may form an interference fit when the spacer 1650 joined with the plugs as shown in FIG. 10C. In a method of implantation, spacer 1650 may be joined to clip 1700, and the resultant implant 1600 may be implanted as a unit into a joint between two bodies, for example two bones. Alternately, spacer 1650 may be implanted into a prepared joint space first, and then clip 1700 may be implanted, with slots 1656, 1658 receiving plugs 1750, 1770. When implanted as described, the inner or medial facing surfaces of plugs 1750, 1770 interfere with spacer 1650, and the outer or lateral facing surfaces of plugs 1750, 1770 interfere with the bone(s) in which they are implanted. This may prevent rotation or counteraction forces between the bone(s) and the implant, while also preventing rotation of the bones with respect to one another.

Figure 11A:
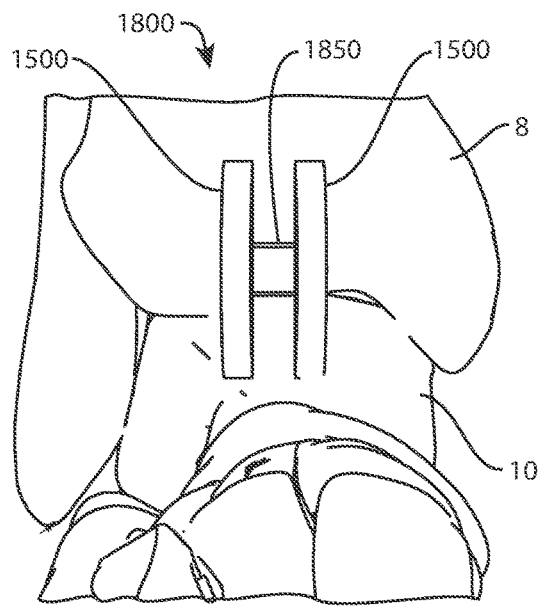
FIG. 11A is an anterior view of an implant including a spacer and two clips, implanted together in a tibiotalar joint.
Figure 11B:
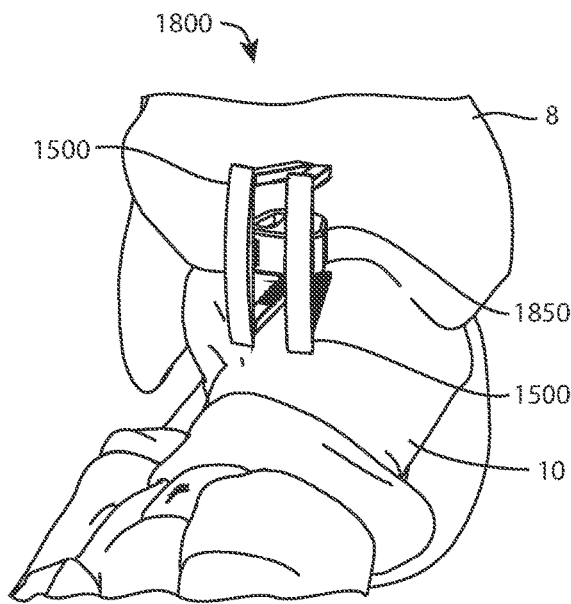
FIG. 11B is an oblique view of the implant and tibiotalar joint of FIG. 11B.
Figure 11C:
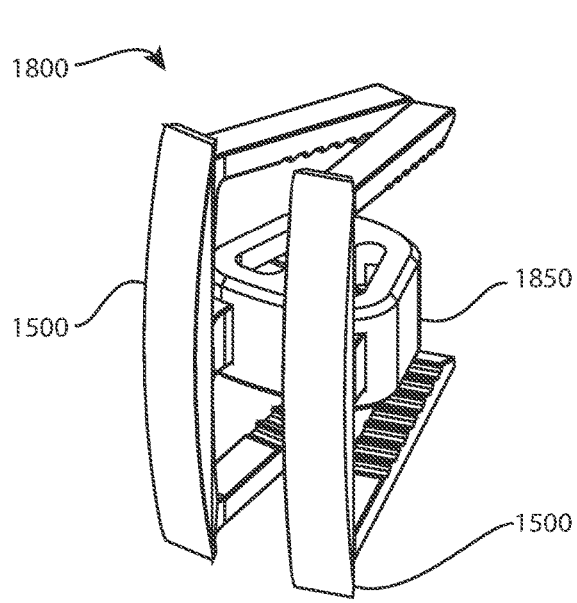
FIG. 11C is an isometric view of the implant of FIG. 11A.
Figure 11D:
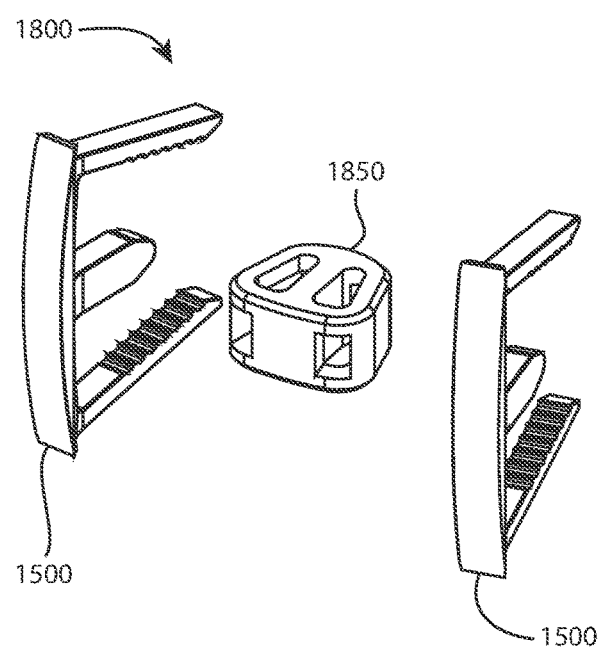
FIG. 11D is an exploded isometric view of the implant of FIG. 11A.
Figure 12A:
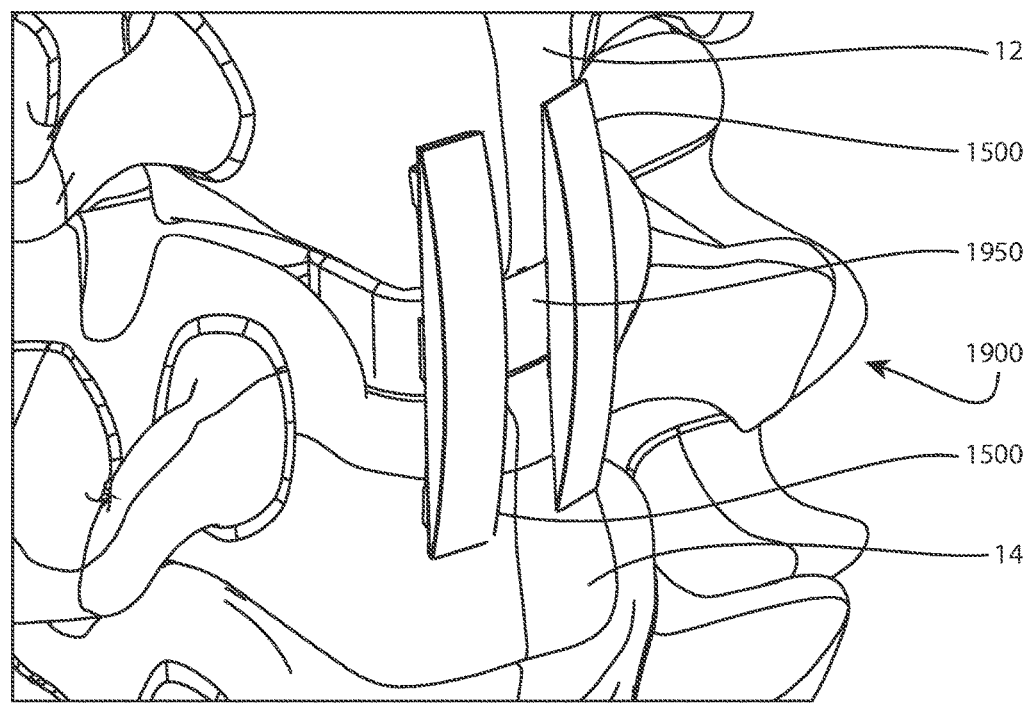
FIG. 12A is an isometric anterior view of an implant including a spacer and two clips, implanted together in an intervertebral joint.
Figures 12B, 12C:
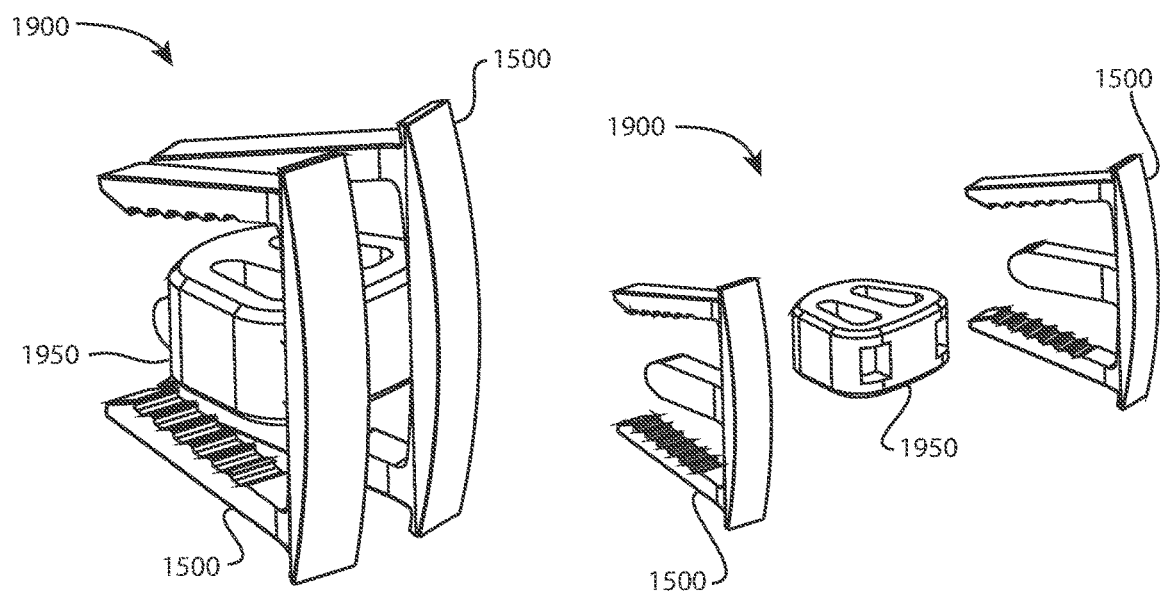
FIG. 12B is an isometric view of the implant of FIG. 12A.
FIG. 12C is an exploded isometric view of the implant of FIG. 12A.

Referring to FIGS. 11A-12C, additional examples of implants comprising clips and spacers are shown. FIGS. 11A and 11B depict an implant 1800 implanted into a tibiotalar joint between a tibia 8 and a talus 10. FIGS. 11C and 11D illustrate that implant 1800 comprises two clips 1500 in combination with a spacer 1850. FIG. 12A depicts an implant 1900 implanted into an intervertebral joint between a first vertebra 12 and a second vertebra 14. FIGS. 12B and 12C illustrate that implant 1900 comprises two clips 1500 in combination with a spacer 1950.

Figure 13:
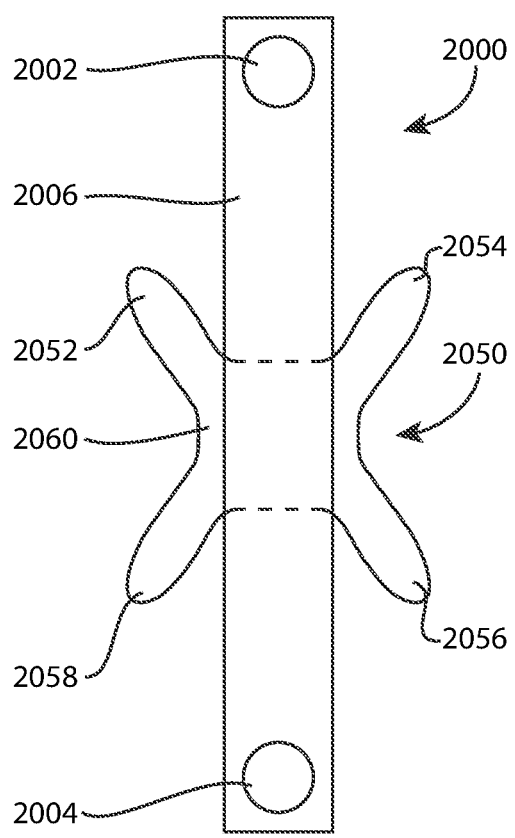
FIG. 13 is a top view of another embodiment of an implant including an anti-torque plug.

Referring to FIG. 13, another embodiment of an implant with an associated keel is shown. Implant 2000 includes implant body 2006, and keel 2050 which projects away from implant body 2006. Implant 2000 may include one or more bone engagement features 2002, 2004 to fasten the implant 2000 to bone, tissue, and/or another device. Bone engagement features 2002, 2004 may be integrated into implant body 2006, for example as posts, legs, or pins; or may be separate fasteners such as screws. The implant 2000 may include a first configuration which is an elastically deformed state for insertion, and a second configuration which is a relaxed or free state when implanted, as described above for implants 1100, 1200. In the embodiment shown, the keel 2050 has a star-shaped cross-sectional shape, with four flanges or lobes 2052, 2054, 2056, 2058 protruding from a central keel body 2060. A distal tip of the keel may be tapered to facilitate introduction into a joint. The keel 2050 may be integrally formed with the implant body 2006 as one piece, or may be a separate entity joined to the implant body before or during implantation. Implant 2000 may be implanted according to the methods described above for implants 1100, 1200. When implanted in a joint, the flanges 2052, 2054, 2056, 2058 can have an interference fit with the surrounding joint tissues, to resist rotation and shear forces around the joint.

Figure 14:
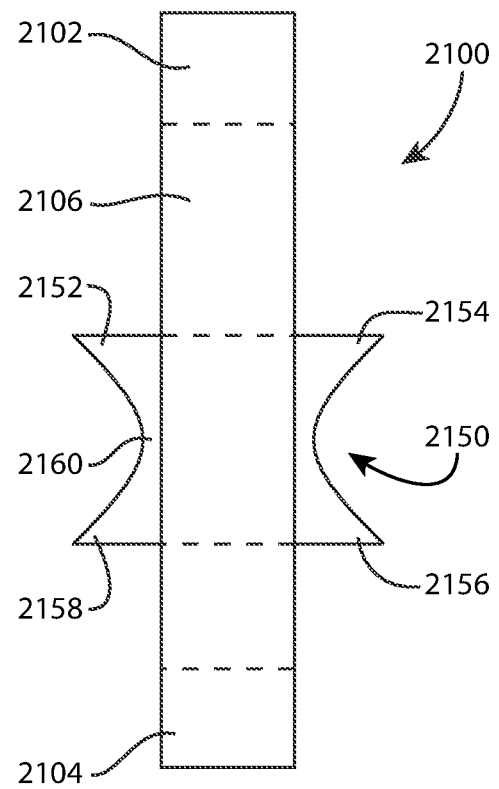
FIG. 14 is a top view of another embodiment of an implant including an anti-torque plug.
Figure 15A:
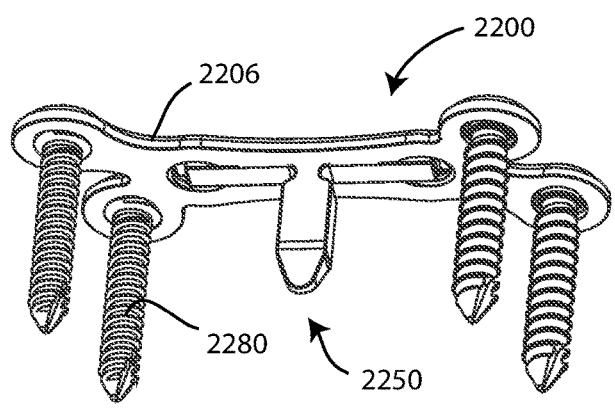
FIG. 15A is an inferior isometric view of an implant include a plate with an anti-torque plug.
Figure 15B:
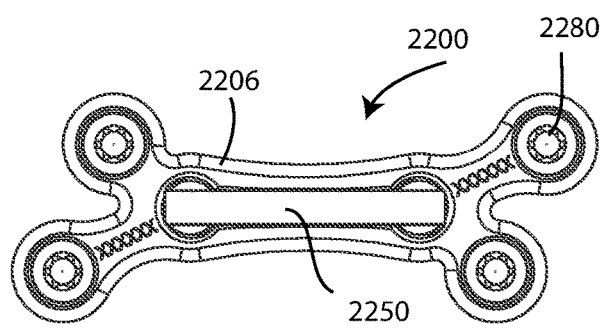
FIG. 15B is a top view of the implant of FIG. 15A.
Figure 15C:
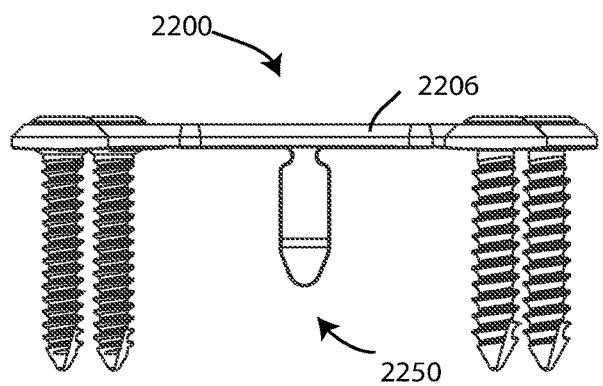
FIG. 15C is a front view of the implant of FIG. 15A.
Figure 15D:
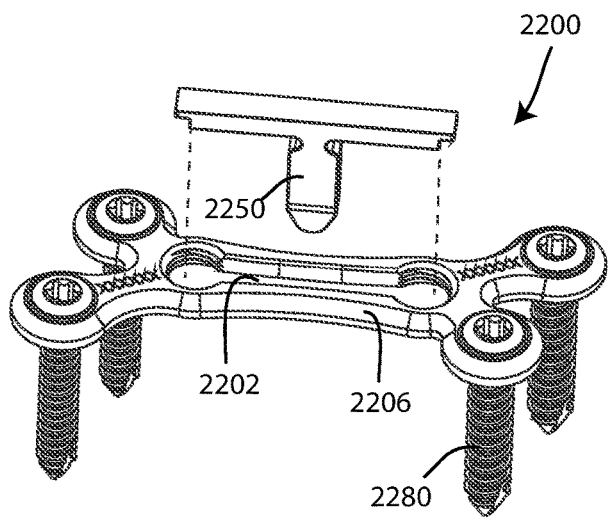
FIG. 15D is a partially exploded view of the implant of FIG. 15A.

Referring to FIG. 14, another embodiment of an implant with an associated keel is shown. Implant 2100 includes implant body 2106, and keel 2150 which projects away from implant body 2106. Implant 2100 may include one or more bone engagement features 2102, 2104 to fasten the implant 2100 to bone, tissue and/or another device. Bone engagement features 2102, 2104 may be integrated into implant body 2106, for example as posts, legs, or pins; or may be separate fasteners such as screws. The implant 2100 may include a first configuration which is an elastically deformed state for insertion, and a second configuration which is a relaxed or free state when implanted, as described above for implants 1100, 1200. In the embodiment shown, the keel 2150 includes four longitudinal edges 2152, 2154, 2156, 2158 projecting from a central keel body 2160. A distal tip of the keel may be tapered to facilitate introduction into a joint. The keel 2150 may be integrally formed with the implant body 2106 as one piece, or may be a separate entity joined to the implant body before or during implantation. Implant 2100 may be implanted according to the methods described above for implants 1100, 1200. When implanted in a joint, the edges 2152, 2154, 2156, 2158 can have an interference fit with the surrounding joint tissues, to resist rotation and shear forces acting on the joint.

Referring to FIGS. 15A-15D, another embodiment of an implant with an associated keel is shown. Implant 2200 includes a plate 2206 and a keel 2250. The plate 2206 depicted includes openings for a plurality of bone screws 2280 for fastening the plate 2206 across a joint between two bones or bodies. In other embodiments, fasteners may be formed integrally with the plate 2206. In the embodiment depicted, the keel 2250 is received in a slot 2202 in the plate and projects inferiorly below the plate. In other embodiments, the keel may be formed integrally with the plate, as shown for implants 1100, 1200. In a method of implantation, drill guide BOO may be used to create a pilot hole for keel 2250 in a joint 2 between first second bodies 4, 6. Plate 2206 may be oriented perpendicular to the joint and fastened to the bodies 4, 6 with fasteners 2280. Keel 2250 may be inserted through slot 2202 and into the joint 2. Keel 2250 may be fastened to the plate 2206. In other methods of implantation, keel 2250 may be joined to the plate 2206 before implantation. The keel 2250 may be replaced by implant 1100, 1200, 1500, 1700, 2000, or 2100. It is appreciated that within the scope of the disclosure, other shapes or configurations of plates may include an integrated or associated keel.

It is appreciated that in other embodiments of the disclosure, keels 1150, 1250, 2060, 2160, 2250 and other keels disclosed herein may have other shapes, including but not limited to square, rectangular, triangular, star, and/or irregular or asymmetric. The keels disclosed herein may also have rounded shapes, if they are sufficiently sized to provide an interference fit with the surrounding tissues or bodies in which they are implanted, in order to resist rotation and shear forces.

Figure 16A:
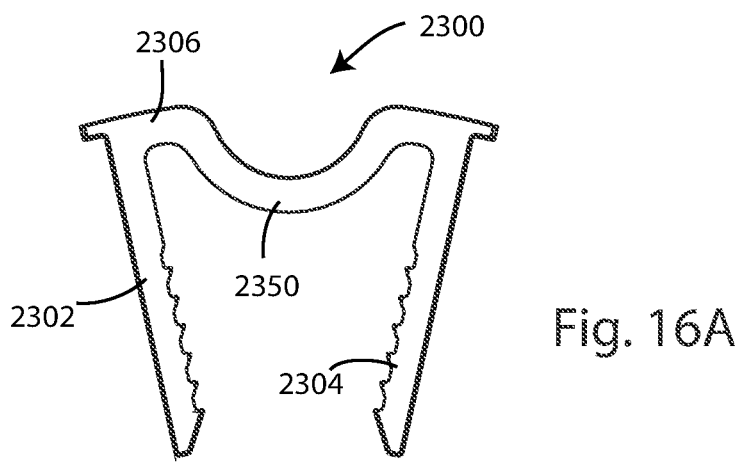
FIG. 16A is a front view of another embodiment of an implant including an anti-torque plug.
Figure 16B:
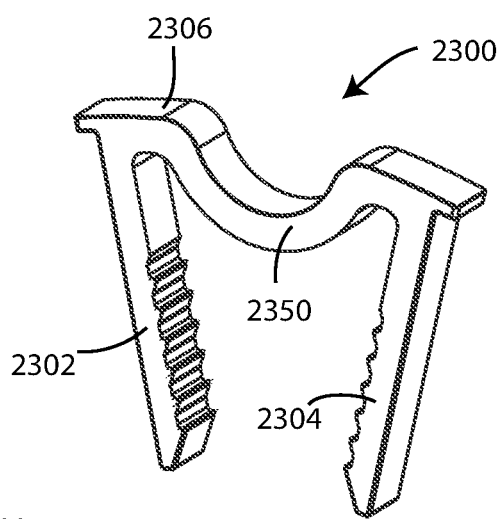
FIG. 16B is an isometric view of the implant of FIG. 16A.
Figure 16C:
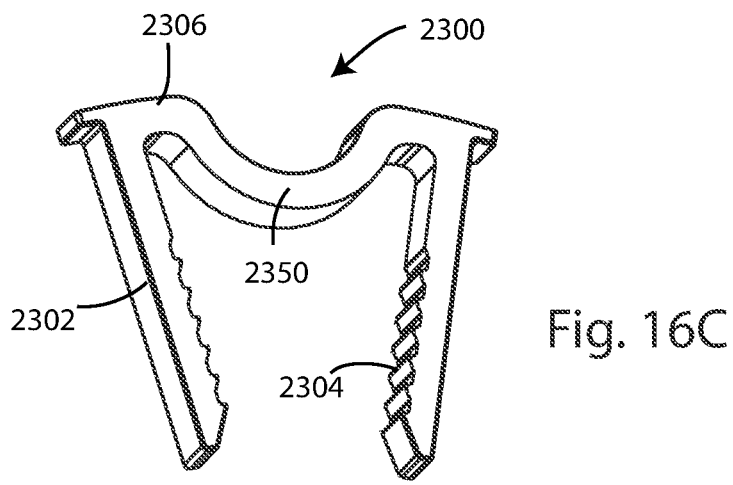
FIG. 16C is another isometric view of the implant of FIG. 16A.

Referring to FIGS. 16A-16C, another embodiment of an implant with an integrated counter-torque feature is shown. Implant 2300 includes first and second bone engagement members 2302, 2304 and an implant body 2306. The implant 2300 may include a first configuration which is an elastically deformed state for insertion, and a second configuration which is a relaxed or free state when implanted, as described above for implants 1100, 1200. The implant 2300 includes protrusion 2350 which projects inferiorly from the implant body 2306. Implant 2300 may be implanted into a joint, as described previously for implants 1100, 1200. Protrusion 2350 is received in joint 2 and may form an interference fit in a prepared pilot hole, and the bone engagement members 2302, 2304 may provide compression across the joint. The protrusion 2350 may provide stability to the joint and resist rotation and shear forces acting on the joint.

Referring to FIGS. 17A-17D, another implant or clip 2400 includes an integrated anti-torque plug 2450. Clip 2400 and other clips disclosed herein may also be referred to as a fastener, staple, or implant. Anti-torque plug 2450 and other anti-torque features disclosed herein may also be referred to as a tab, keel, post, or implant. One or more clips 2400 may be implanted in a single procedure, for example to join two bone portions together.

Figure 17A:
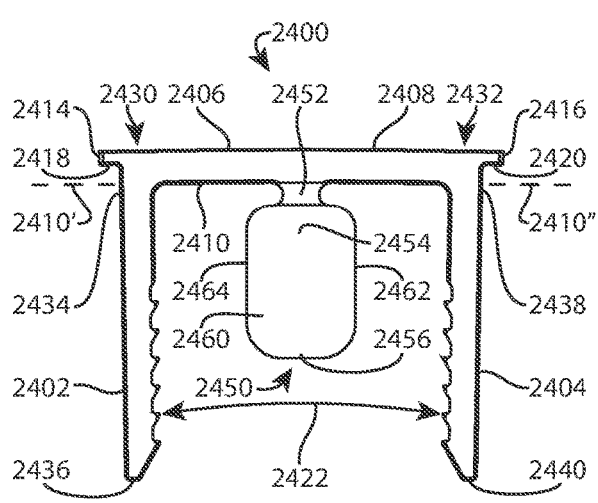
FIG. 17A is a front view of another implant comprising a compression bone staple having an integrated anti-torque plug.
Figure 17B:
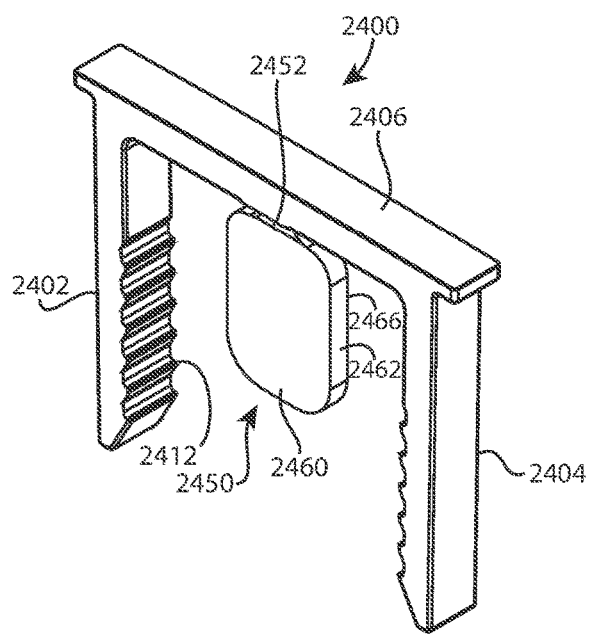
FIG. 17B is an isometric view of the implant of FIG. 17A.

Referring to FIGS. 17A and 17B, the clip 2400 includes bone engaging members 2402 and 2404 which may be integral to a clip bridge 2406, also referred to as a clip body. The bone engaging members 2402 and 2404 may be referred to as legs. In other embodiments within the scope of the disclosure, a clip may include more than two bone engaging members; or alternatively may include openings for one or more independent fasteners in lieu of the bone engaging members. In other embodiments of the disclosure, the implant 2400 may be more similar to a plate. The bone engaging member 2402 extends from a left end 2430 of the clip bridge 2406 and the bone engaging member 2404 extends from an opposite right end 2432 of the clip bridge 2406. Bone engaging member 2402 has a proximal end 2434 attached to the left end 2430 of the clip bridge 2406 and an opposite distal end 2436 which is a free end. Bone engaging member 2404 has a proximal end 2438 attached to the right end 2432 of the clip bridge 2406 and an opposite distal end 2440 which is a free end. Clip bridge 2406 has at least one upper or proximal surface 2408 and at least one lower or distal surface 2410. The lower surface 2410 may be referred to as a bone facing surface. Bone engaging member 2402 extends from the lower surface 2410 beside bone engaging member 2404. The bone engaging members 2402 and 2404 may have features 2412 that may improve bone purchase or improve pull out strength of the clip 2400 from bone or soft tissue. The features 2412 may be referred to as teeth or serrations. The features 2412 are shown on facing sides of the bone engaging members 2402, 2404 but may be on any or all sides of the bone engaging members. The clip 2400 may have projections or other connecting means 2414 and 2416 for connection with a means of insertion. The connecting means 2414, 2416 may be referred to as tabs, ears, protrusions, wings, retainers, or retaining members. The connecting means 2414 and 2416 are shown extending sideways outwardly from the left and right ends 2430, 2432 of the bridge 2406, respectively, along a longitudinal direction established by the bridge. In other embodiments, the connecting means may project perpendicularly with respect to the bridge. The connecting means 2414 and 2416 may have lower or distal surfaces 2418 and 2420 respectively that may releasably engage with a means of insertion that may allow an inserter or other means of insertion to be side loading, top loading or pivotably loaded. For example, an inserter for clip 2400 may be side loading or pivotably loading. The lower surfaces 2418, 2420 may be referred to as bone facing surfaces. Referring to FIG. 17A, the lower surfaces 2418, 2420 are proximally spaced apart from, or proximally offset from, the lower surface 2410. The dashed extension lines 2410' and 2410" in FIG. 17A show the level of the lower surface 2410 versus the lower surfaces 2418, 2420.

Figure 17C:
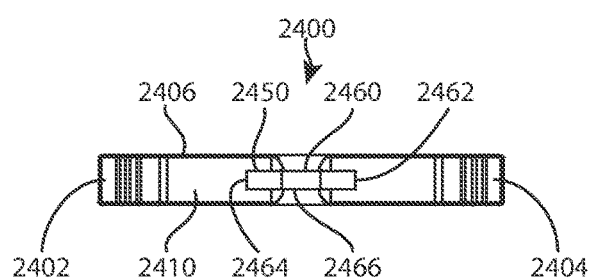
FIG. 17C is a bottom view of the implant of FIG. 17A.
Figure 17D:
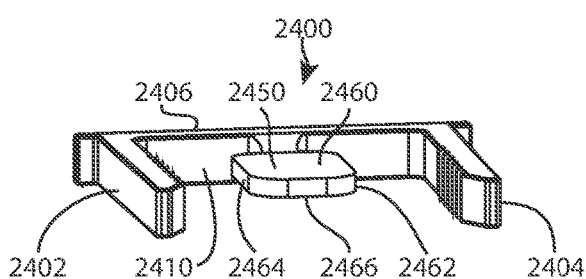
FIG. 17D is a bottom oblique view of the implant of FIG. 17A.
Figure 18A:
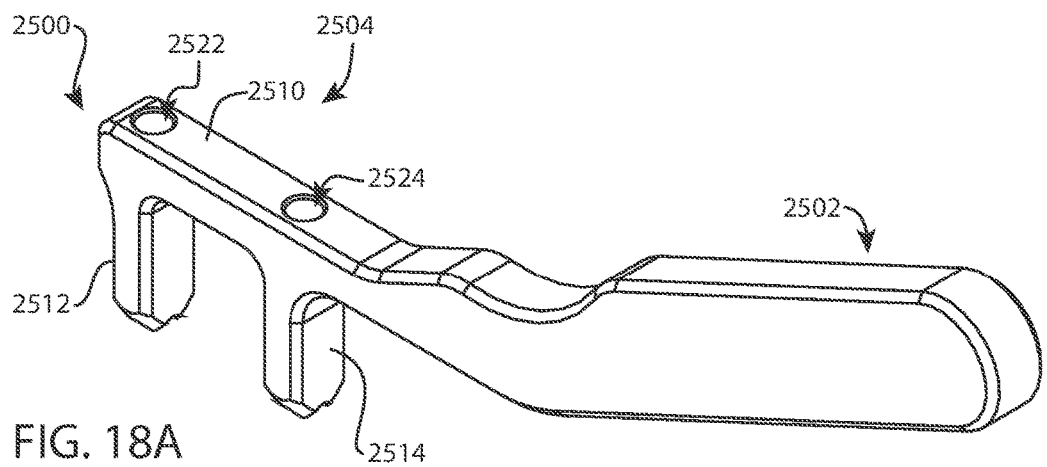
FIG. 18A is an isometric view of a drill guide for use with the implant of FIG. 17A.
Figure 18B:
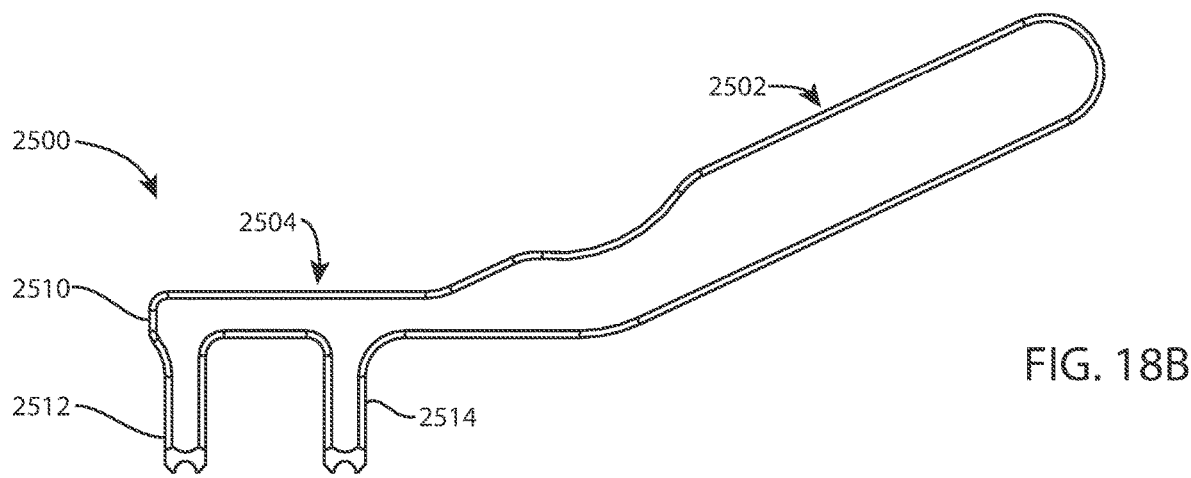
FIG. 18B is a front view of the drill guide of FIG. 18A.
Figure 18C:
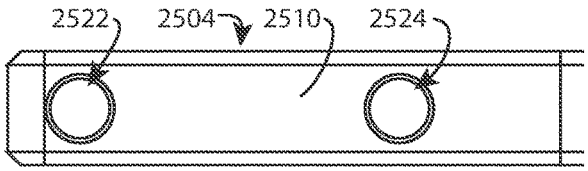
FIG. 18C is a top detail view of a guide portion of the drill guide of FIG. 18A.
Figure 18D:
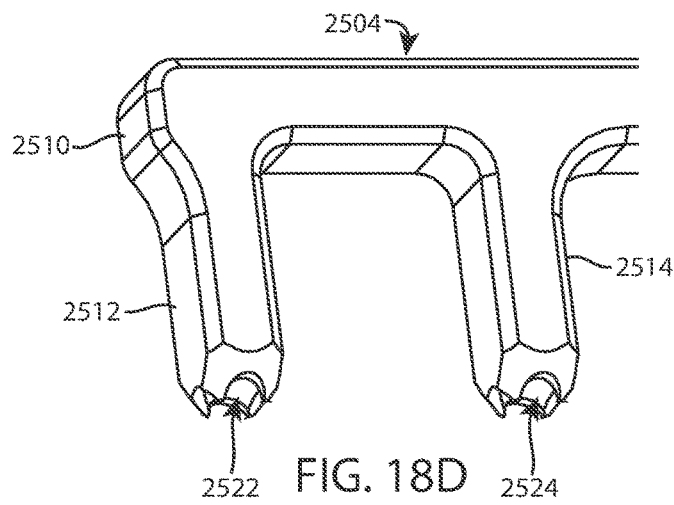
FIG. 18D is an isometric detail view of the guide portion of the drill guide of FIG. 18A.

An integrated anti-torque plug 2450 projects distally from the lower surface 2410 of bridge 2406. In the embodiment depicted, a single plug 2450 is centered between bone engaging members 2402, 2404; in other embodiments the plug may be off-center relative to the members 2402, 2404, and/or a plurality of plugs may be included. The plug may also be connected to the implant 2400 in more than one location along the lower surface 2410 of bridge 2406. Plug 2450 includes a neck portion 2452 where the plug is joined to bridge 2406, a body 2454, and a tip 2456. Neck portion 2452 may be formed as a waist having a reduced width with respect to the plug body 2454 as shown in FIGS. 17A-17D; in other embodiments the neck portion 2452 may be wider than or equal in width with respect to the plug body 2454. Preferably, plug 2450 is connected to the clip 2400 only via the bridge 2406, and not along the bone engaging members 2402, 2404. Plug 2450 may be rectangular in cross-section and includes four sides 2460, 2462, 2464, 2466. The plug thickness between sides 2460 and 2466 may be less than, the same as, similar to, or greater than the thickness of the bridge 2406 and/or bone engaging members 2402, 2404 of the clip 2400 in the same direction (front-back). Preferably, the plug thickness between sides 2460 and 2466 is less than the thickness of the bridge and bone engaging members 2402, 2404 in the same direction, as seen best in FIGS. 17C-17D. The plug tip 2456 may be tapered on at least two sides 2462, 2464 with respect to the plug body to facilitate insertion into a joint. The plug sides 2460, 2462, 2464, 2466 may be smooth as seen in FIGS. 17A-17D; in other embodiments one or more plug sides may include teeth, serrations, or other surface roughening. In other embodiments, the plug may have a differently shaped cross-section. The plug does not preclude compression of the bone segments by the bone engaging members 2402, 2404, at least because the plug is oriented in a plane coplanar with, or parallel to, the plane of the bridge 2406 and bone engaging members 2402, 2404 of the clip 2400, as shown in FIG. 17C.

A means of insertion may maintain the clip 2400 in a first configuration thereby allowing a second configuration once an inserter is disassembled from the implant. The first configuration may be an elastically deformed state, for example an insertion state. The second configuration may be a free state or an implanted state, as seen in FIG. 17A. The means of insertion may utilize features similar to connecting means 2414 and 2416 in combination with other surfaces such as top surface 2408. This combination of means of insertion may be used to maintain one or more features or arms or projections in a particular configuration. This combination of means of insertion may create a bending modality, such as a three point or four point bend, to maintain a specific clip device configuration or combination of configurations. A combination of surfaces and means of insertion, such as connecting means 2414, may be used on the entire clip or portions of a clip to create or maintain a particular configuration of a clip. For example, a tab such as 2414 and top surface, such as 2408 may be used to maintain one side of a clip or one leg of a clip in a particular configuration. When disassembled, that leg may have a configuration that is different from or the same as the configuration of the rest of the clip.

Referring to FIGS. 17A-17B, the clip 2400 is shown in the free state, or relaxed state, which is the shape of the clip 2400 when no external forces are acting upon the clip 2400, other than gravity; the clip 2400 experiences no elastic or plastic deflection or deformation. In the free state, the bone engaging members 2402 and 2404 converge as they extend away from the bridge 2406 so that the distal ends 2436, 2440 are closer together than are the proximal ends 2434, 2438. An angle 2422 is formed between the converging bone engaging members 2402 and 2404 in the free state. The angle 2422 opens toward the bridge 2406. The angle 2422 may be referred to as a free state angle.

Referring to FIGS. 18A-18D, a drill guide 2500 may be employed to prepare pilot holes for implant 2400 in a joint 2 between a first bone 4 and a second bone 6. The joint 2 may be an actual anatomical joint, an osteotomy, a fracture, or an interface between the first and second bones 4, 6. Drill guide 2500 may include a handle portion 2502 and a guide portion 2504; some embodiments may exclude the handle portion 2502. The guide portion 2504 includes a guide bar 2510 from which one or more guide elements may depend. In the embodiment depicted, guide portion 2504 includes first and second single hole guide elements 2512, 2514. Other embodiments of the drill guide 2500 can include any number and arrangement of guide elements corresponding to a particular implant or clip, or set of implants; and in other embodiments the guide elements may not depend from the guide bar. Guide element 2512 surrounds and supports a first lumen 2522 and guide element 2514 surrounds and supports a second lumen 2524. All the guide elements may include pointed or tapered distal tips to facilitate engagement with bone or tissues during the drilling procedure.

In the embodiment depicted, the first and second lumens 2522, 2524 are circular in a transverse cross section, and each is shaped to guide a drill for drilling a single bore. In the embodiment shown, the first and second lumens 2522, 2524 are co-planar. In other embodiments, one or more of the lumens may be out of the plane of the others.

Figure 19A:
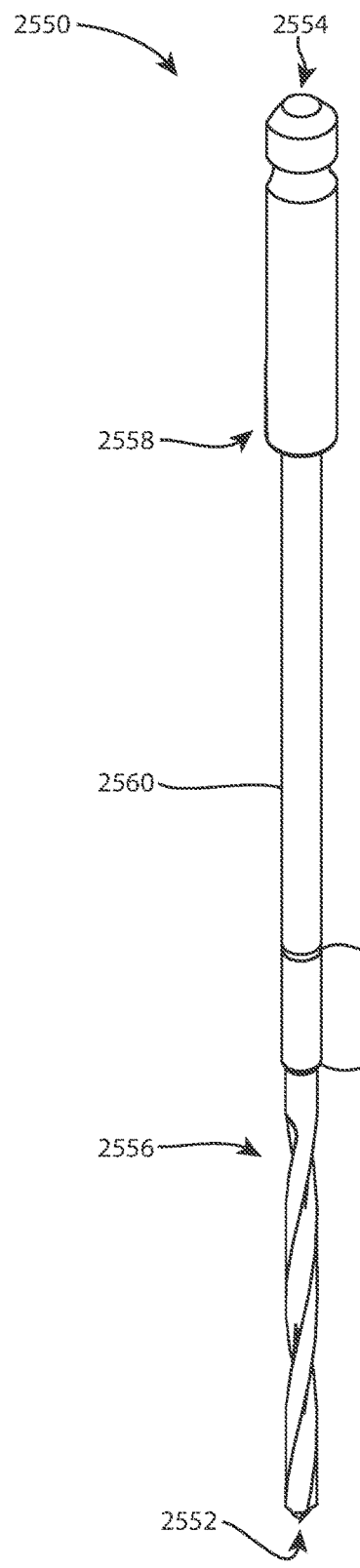
FIG. 19A is an isometric view of a drill for use with the drill guide of FIG. 18A.
Figure 19B:
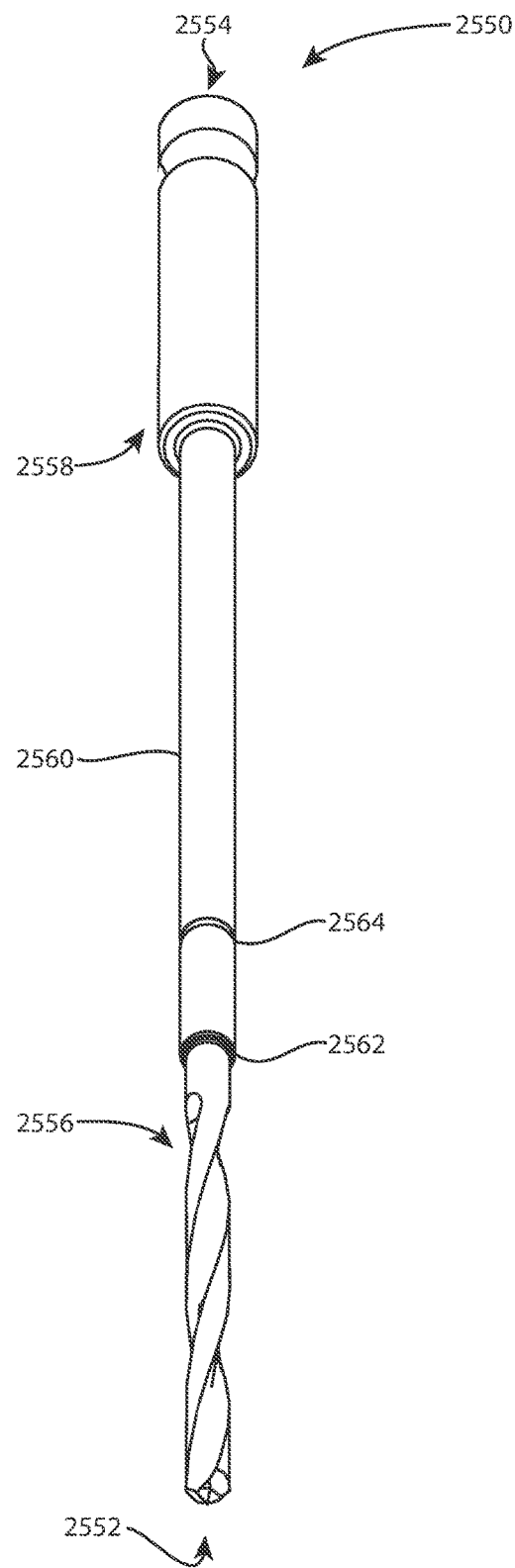
FIG. 19B is a bottom oblique view of the drill of FIG. 19A.

Referring to FIGS. 19A-19B, a drill bit 2550 may be used with the drill guide 2500 to prepare pilot holes for implant 2400. The drill bit 2550 extends between a distal end 2552 and a proximal end 2554. The distal end 2552 includes a cutting portion 2556 with side and/or end cutting flutes. The proximal end 2554 includes a torque coupling portion 2558 for connection to a powered or manual torque source, such as an electric drill or a T-handle. The drill bit 2550 is shown with an optional intermediate portion 2560 with an outer diameter that is larger than the outer diameter of the cutting portion 2556 and smaller than the outer diameter of the torque coupling portion 2558. The drill bit 2550 may include one or more depth marks and/or depth stops and/or indicia. For example, a shoulder 2562 between the cutting portion 2556 and the intermediate portion 2560 may serve as a depth mark or depth stop. Another depth mark 2564 is shown in the intermediate portion 2560 proximal to the shoulder 2562. The shoulder 2562 and/or depth mark 2564 may align with, or may make contact with, a corresponding feature of the drill guide 2500. For example, the depth mark 2564 may align with the proximal side of the guide bar 2510 to indicate that the drill bit 2550 has been advanced to the proper depth.

Figure 20A:
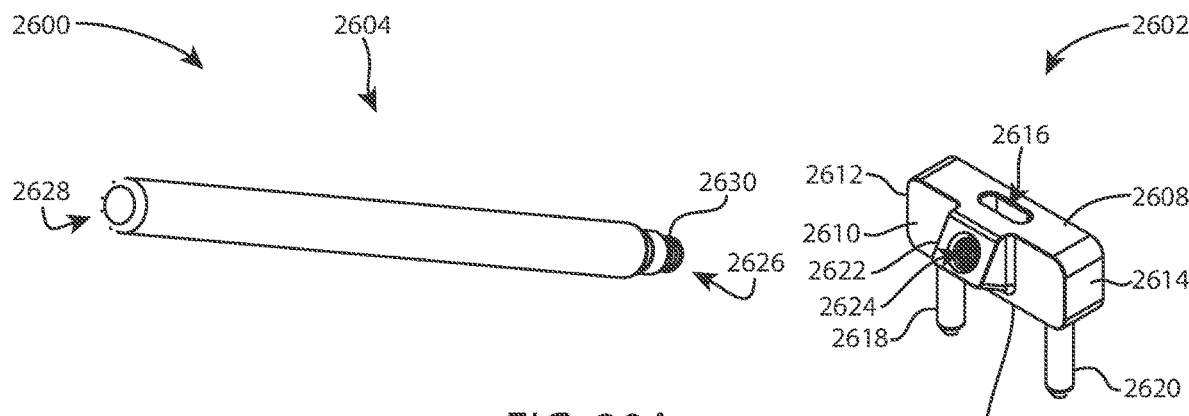
FIG. 20A is an exploded isometric view of a handle and a punch guide body of a punch guide for use with the implant of FIG. 17A.
Figure 20B:
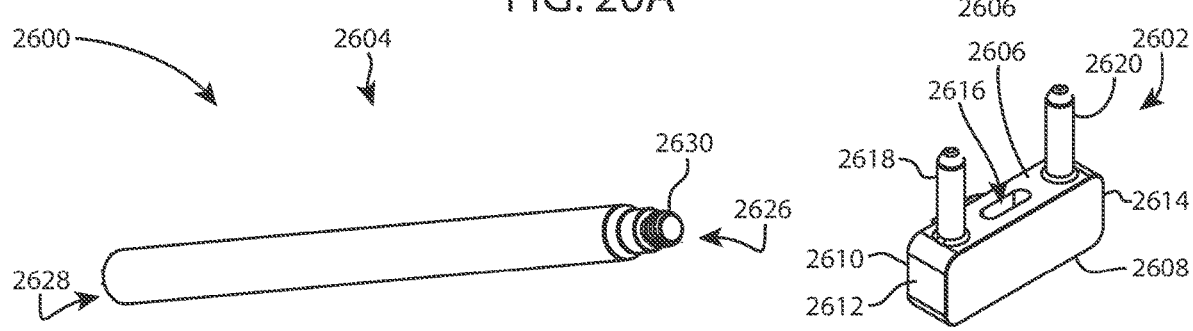
FIG. 20B is another exploded isometric view of the handle and punch guide body of FIG. 20A from a different direction.

Referring to FIGS. 20A-20B, a punch guide 2600 may include a punch guide body 2602 and a handle 2604. The punch guide 2600 is illustrated in exploded views in FIGS. 20A-20B and operatively assembled in FIGS. 26A-27B.

The punch guide body 2602 may be a generally rectangular shape with a distal side 2606, a proximal side 2608, a handle-facing side 2610, a left side 2612, and a right side 2614. A lumen 2616 extends through the punch guide body 2602 between the distal and proximal sides 2606, 2608. The lumen 2616 may have a transverse cross section that is elongated in a left-right direction as shown. The cross-sectional shape may be rectangular, oval, snowman, or another shape. An oval shape is shown. The lumen 2616 may be centered in the left-right width of the punch guide body 2602. Bilateral pegs 2618, 2620 extend distally from the distal side 2606 to the left and right of the lumen 2616. The pegs 2618, 2620 may have distal tapered or pointed tips as shown in FIG. 20B. A boss 2622 may extend obliquely outwardly and proximally from the handle-facing side 2610. The boss 2622 may be centered in the left-right width of the punch guide body 2602. An internally threaded hole 2624 may extend into the boss 2622.

The handle 2604 may be a generally cylindrical shaft that extends between a distal end 2626 and a proximal end 2628. The distal end 2626 may include an externally threaded distal tip portion 2630 with threads that are complementary to the internal threads in the hole 2624 of the punch guide body 2602. The proximal end 2628 may function as a handle.

The punch guide 2600 may be assembled by threading the distal tip portion 2630 into the internally threaded hole 2624. In use, the punch guide body 2602 and handle 2604 are fixed together.

Figure 21A:
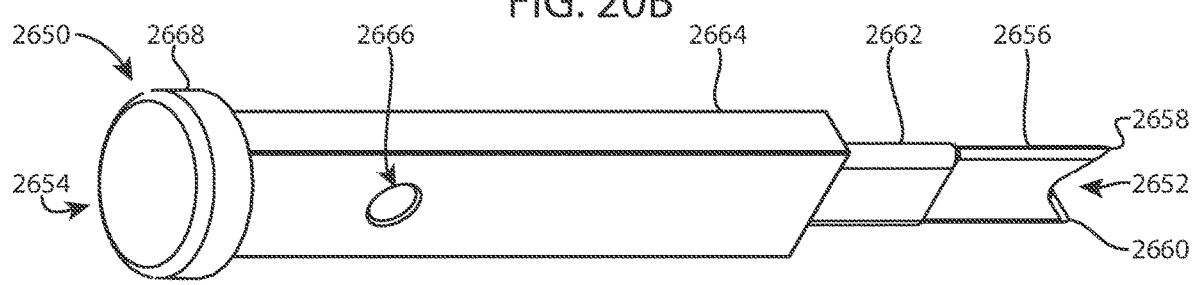
FIG. 21A is an isometric view of a punch for use with the punch guide of FIG. 20A.
Figure 21B:
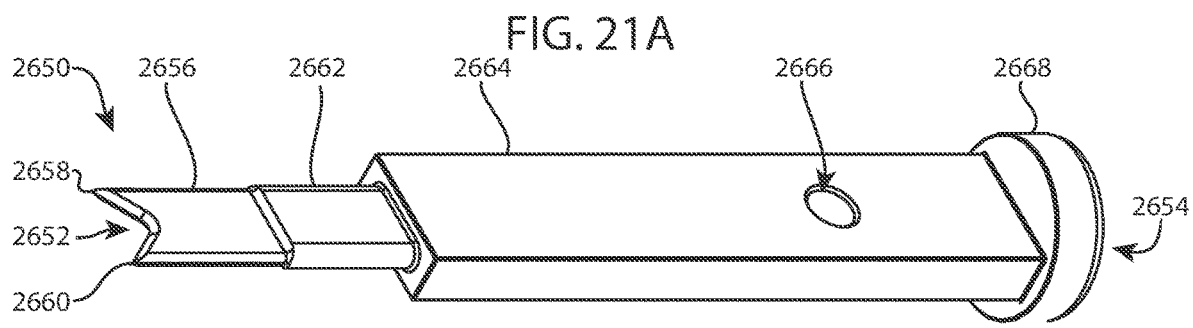
FIG. 21B is another isometric view of the punch of FIG. 21A from a different direction.

Referring to FIGS. 21A-21B, a punch 2650 may be used with the punch guide 2600 to prepare a slot to receive the plug 2450 of the clip 2400. The punch 2650 extends between a distal end 2652 and a proximal end 2654. The punch 2650 may include four portions or segments along its distal-proximal length. A first portion 2656 may extend proximally from the distal end 2652. The first portion 2656 may have an elongated cross-sectional shape that is complementary to the cross-sectional shape of the lumen 2616 of the punch guide 2600. The distal-most aspect of the first portion 2656 may be sharpened or pointed to penetrate bone. Two points 2658, 2660 are shown, with a distal sharp concave profile between the points. A second portion 2662 may extend proximally from the first portion 2656. The second portion 2662 may have the same cross-sectional shape as the first portion, outwardly offset so that the second portion is wider and/or thicker than the first portion. A third portion 2664 may extend proximally from the second portion 2662. The third portion 2664 may have a cross sectional shape that is similar to, or different from, the cross-sectional shapes of the first and second portions 2656, 2662, and which may be outwardly offset so that the third portion is wider and/or thicker than the second portion. The third portion 2664 is shown with a rectangular cross-sectional shape. A transverse hole 2666 may extend through the thickness of the punch 2650 in the third portion 2664. A fourth portion 2668 may extend proximally from the third portion 2664. The fourth portion 2668 may have a circular cross-sectional shape that is outwardly offset so that the fourth portion is wider and/or thicker than the third portion 2664. The third and fourth portions 2664, 2668, together or separately, may function as a handle. The fourth portion 2668 may function as a strike platform to impact the punch 2650 distally into bone or proximally out of bone.

In an alternate embodiment, the punch guide 2600 and punch 2650 may be combined together in a single instrument. In one example of this embodiment, the punch guide body 2602, handle 2604, and punch 2650 may be formed together as a unitary part. In this example, the feature corresponding to the punch 2650 may be equivalent to the first portion 2656 shown in FIGS. 21A, 21B, and 27B, which is the portion that protrudes distally from the punch guide body 2602 between the pegs 2618, 2620.

Referring to FIGS. 22A-22F, an inserter 2700 may be used with any of the implants or clips disclosed herein. The inserter 2700 may include a body 2702, a ram 2704, a ram pin 2706, a knob 2708, a shaft 2710, and a knob pin 2712. The ram 2702 and the ram pin 2706 may be coupled together as a ram sub-assembly 2714. The knob 2708, the shaft 2710, and the knob pin 2712 may be coupled together as a shaft sub-assembly 2716.

The body 2702 extends between a distal end 2718 and a proximal end 2720. The body 2702 may be a generally plate-like part that is wider at the distal end 2718 and narrower at the proximal end 2720. The distal-most aspect of the body 2702 may include two jaws or hooks 2722, 2724 that face each other across a shallow alcove 2726. The hooks 2722, 2724 include proximal surfaces 2728, 2730, respectively. The hook 2722 includes a front wall 2732 and the hook 2724 includes a back wall 2734. A notch 2736 extends proximally from a central portion of the alcove 2726. A first slot 2738 extends through the body 2702 proximal to the notch 2736 along a front-back direction. The slot 2738 is elongated along a proximal-distal direction. A second slot 2740 extends through the body 2702 proximal to the slot 2738 along the front-back direction. The slot 2740 is elongated along the proximal-distal direction. The second slot 2740 is longer than the first slot 2738 in the proximal-distal direction and is wider than the first slot 2738 in the left-right direction. A first central longitudinal hole 2742 extends proximally into the body 2702 from the distal end 2718 to the slot 2740. The slot 2738 and the hole 2742 intersect at right angles. A second central longitudinal hole 2744 extends distally into the body 2702 from the proximal end 2720 to the slot 2740. The hole 2744 may be internally threaded. The body 2702 may be thickened in the vicinity of the hole 2744 so as to adequately support the hole 2744 under expected loads.

The ram 2704 extends between a distal end 2750 and a proximal end 2752. The ram 2704 includes a distal head 2754, which may be generally rectangular as shown. As seen best in FIGS. 22A and 22C, the distal-most aspect of the head 2754 may be convex in a front or back view. A shaft 2756 extends proximally from the head 2754. The shaft 2756 may have a circular cross section as shown. The outer diameter of the shaft 2756 may be similar to the thickness of the head 2754 in a front-back direction, and may be less than the width of the head in a left-right direction. A transverse hole 2758 extends through the shaft 2756 near the proximal end 2752.

The ram 2702 and the ram pin 2706 may be coupled together to form the ram sub-assembly 2714 by inserting the ram pin through the hole 2758.

The knob 2708 may be a generally rectangular part which may be contoured to match the proximal end 2720 of the body 2702. A central longitudinal hole 2760 may extend through the knob in a proximal-distal direction. A transverse hole 2762 may extend through the knob in a front-back direction.

The shaft 2710 extends between a distal end 2770 and a proximal end 2772. The shaft 2710 may include three portions or segments along its distal-proximal length. A first portion 2774 extends proximally from the distal end 2770, has a circular cross section, and a smooth outer surface. A second portion 2778 extends proximally from the first portion 2774 and has external threads 2780. The minor diameter of the external threads may be greater than the outer diameter of the first portion 2774. A third portion 2782 extends proximally from the second portion 2778 to the proximal end 2720, has a circular cross section, and a smooth outer surface. The outer diameter of the third portion 2782 may be similar to the minor diameter of the external threads 2780. A transverse hole 2784 extends through the third portion 2782 near the proximal end 2772.

The knob 2708, the shaft 2710, and the knob pin 2712 may be coupled together to form the shaft sub-assembly 2716 by inserting the third portion 2782 of the shaft 2710 into the hole 2760 of the knob 2708, aligning the transverse holes 2762, 2784, and inserting the knob pin 2712 through the holes 2762, 2784.

Figure 22A:
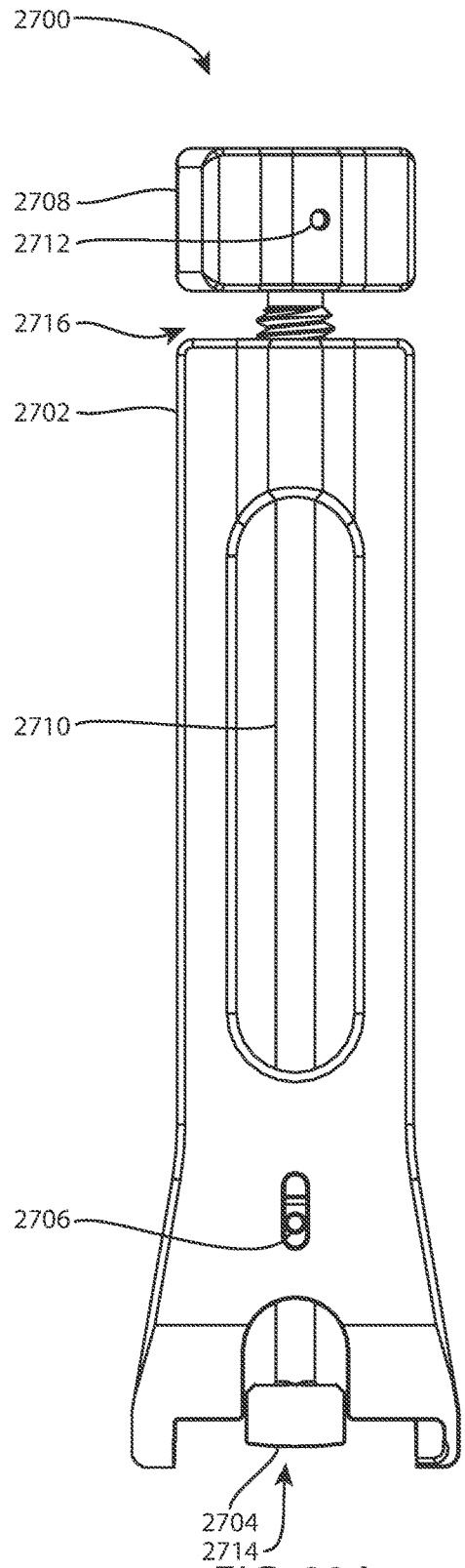
FIG. 22A is a front view of an implant inserter.
Figure 22B:
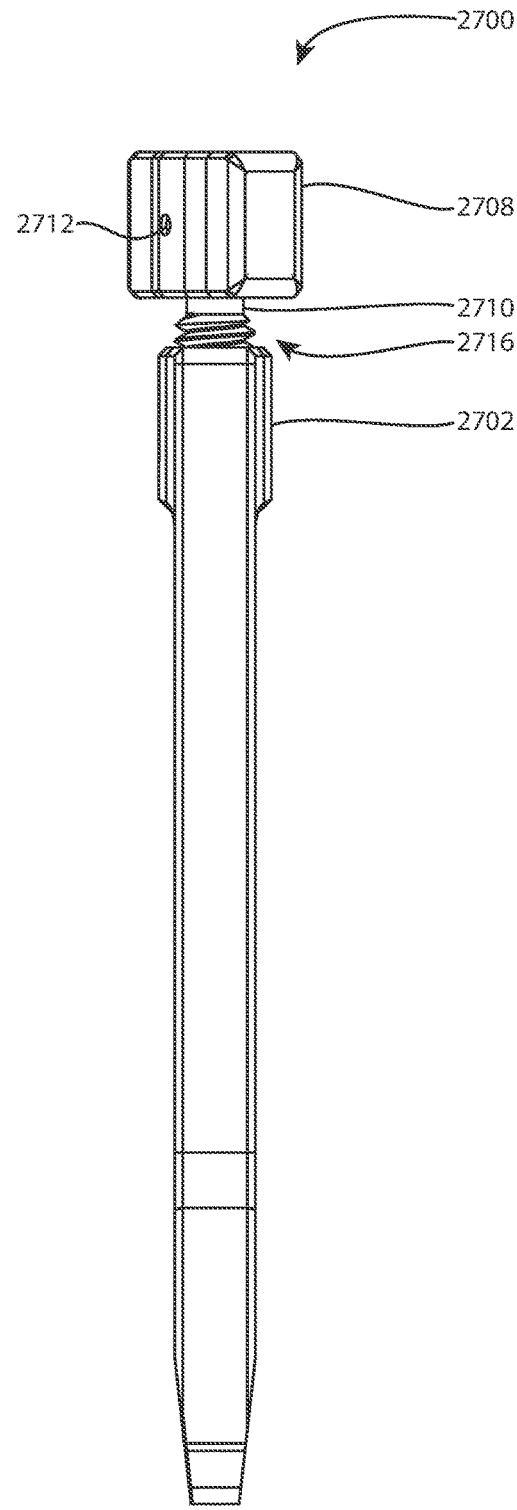
FIG. 22B is a side view of the implant inserter of FIG. 22A.
Figure 22C:
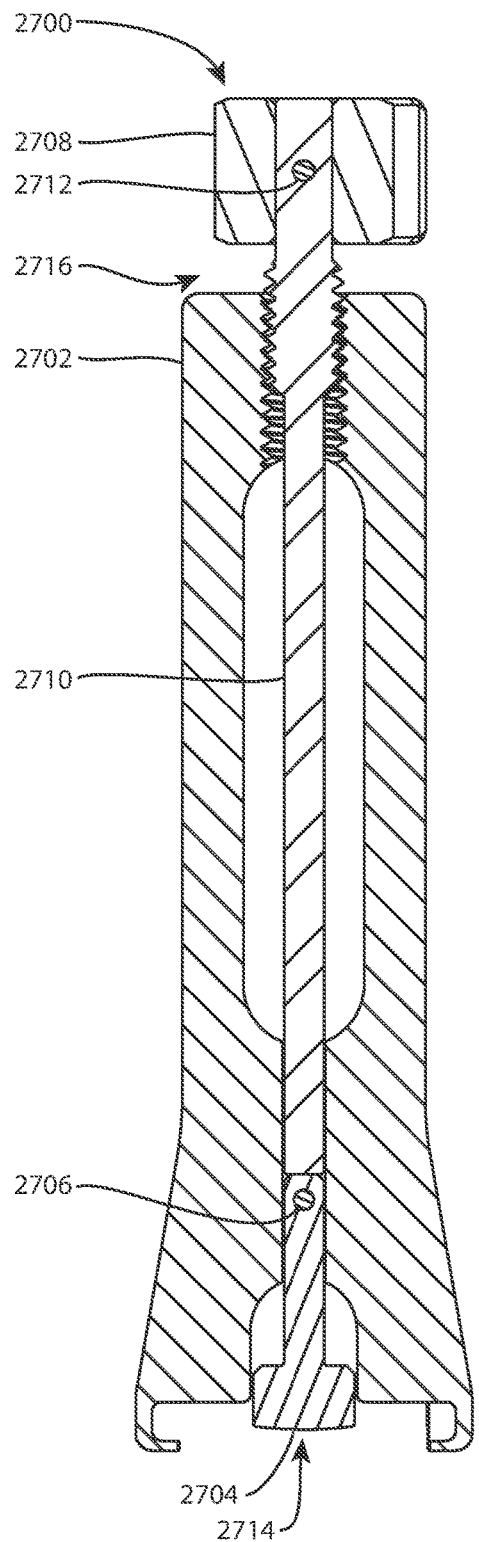
FIG. 22C is a front cross-sectional view of the implant inserter of FIG. 22A, taken along section line 22C-22C of FIG. 22B.
Figure 22D:
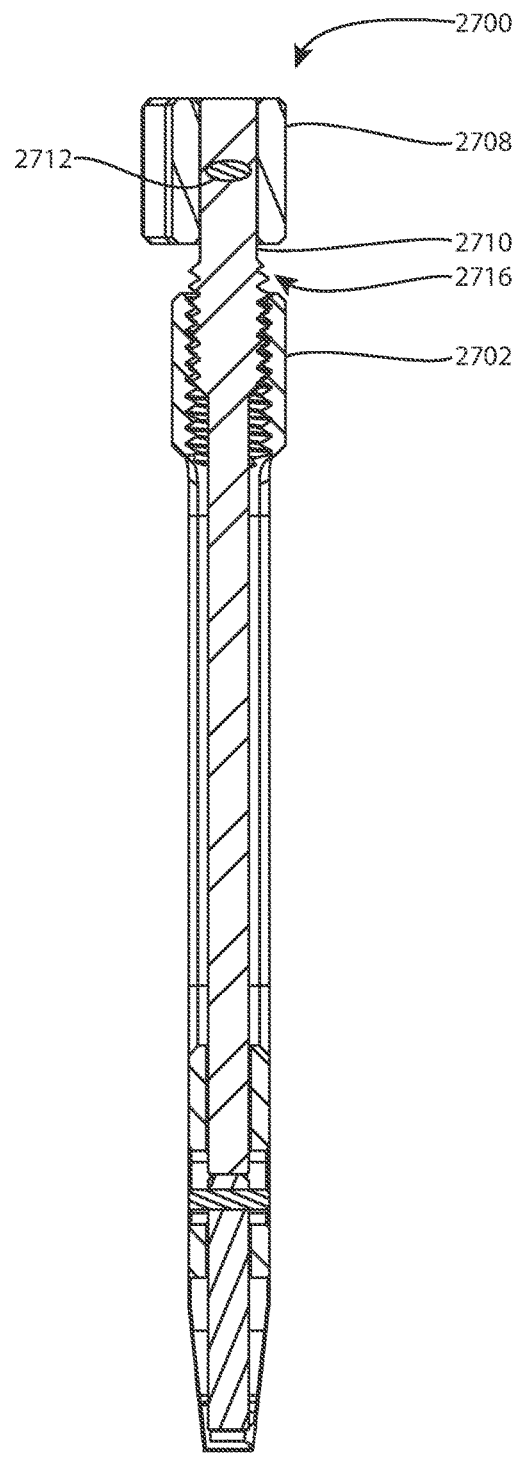
FIG. 22D is a side cross-sectional view of the implant inserter of FIG. 22A, taken along section line 22D-22D of FIG. 22A.

The inserter 2700 may be assembled by inserting the shaft 2756 of the ram 2704 into the hole 2742 of the body 2702, aligning the transverse hole 2758 with the first slot 2738, and inserting the ram pin 2706 through the slot 2738 and hole 2758; and by inserting the first portion 2774 of the shaft 2710 into the hole 2744 of the body 2702 and advancing the shaft distally relative to the body until the first portion enters the hole 2742 and the external threads 2780 engage the internal threads of the hole 2744. The head 2754 may be at least partially received in the notch 2736. Referring to FIGS. 22C and 22D, the distal end 2770 of the shaft 2710 directly contacts the proximal end 2752 of the ram 2704, but the two parts are not otherwise mechanically connected.

When the inserter 2700 is operatively assembled, the ram 2704 is free to translate proximal-distal relative to the body 2702 within the constraint provided by the ram pin 2706 in the slot 2738, but the ram is prevented from rotating about its shaft 2756 relative to the body by the ram pin in the slot. The shaft sub-assembly 2716 engages the body 2702 via the external threads 2780 engaged with the internal threads of the hole 2744. Thus the shaft sub-assembly rotates and translates simultaneously relative to the body. The shaft sub-assembly 2716 is removable from the assembled body 2702, ram 2704, and ram pin 2706, which is advantageous at least for cleaning. Turning the knob 2708 clockwise advances the shaft sub-assembly 2716 distally, which pushes the ram sub-assembly 2714 distally. Turning the knob 2708 counterclockwise moves the shaft sub-assembly proximally, which permits the ram sub-assembly to move proximally under an external force such as the elastic force of a clip bridge or the force of gravity. However, the distal end 2770 of the shaft 2710 is not mechanically coupled to the proximal end 2752 of the ram 2704 in a way that enables the shaft sub-assembly 2716 to pull the ram sub-assembly 2714 proximally.

The inserter 2700 may be coupled to any implant or clip disclosed herein. Clip 2400 will be used as an example. A method of coupling the inserter 2700 to the clip 2400 may include any or all of the following steps in any order: rotating the knob 2708 counterclockwise; rotating the shaft 2710 counterclockwise; rotating the shaft sub-assembly 2714 clockwise; moving the ram 2704 proximally; moving the ram sub-assembly 2714 proximally; positioning the upper surface 2408 of the bridge 2406 of the clip 2400 against the distal-most aspect of the ram 2704; orienting the bridge 2406 relative to the body 2702 so that the front wall 2732 is in front of the connecting means 2414 and the back wall 2734 is in back of the connecting means 2416; orienting the bridge 2406 relative to the body 2702 so that the longitudinal direction established by the bridge is oblique to the left-right direction between the hooks 2722, 2724; rotating the body 2702 clockwise; sliding the hooks 2722, 2724 under the connecting means 2414, 2416; rotating the knob 2708 clockwise; rotating the shaft 2710 clockwise; rotating the shaft sub-assembly 2714 clockwise; moving the ram 2704 distally relative to the body 2702; moving the ram sub-assembly 2714 distally relative to the body 2702; and contacting the upper surface 2408 of the bridge 2406 of the clip 2400 with the distal-most aspect of the ram 2704.

The inserter 2700 may be disconnected from the implant 2400 at least by reversing the assembly steps.

When the implant 2400 and the inserter 2700 are operatively assembled, the inserter 2700 may be actuated to move the implant 2400 between the free state and an elastically deformed state. Referring to FIG. 22C, clockwise rotation of the knob 2708, the shaft 2710, or the shaft sub-assembly 2716 causes the ram 2704 or the ram sub-assembly 2714 to move distally relative to the body 2702 against the static resistance or support of the hooks 2722, 2724 or other static support feature(s). This causes the bridge 2406 to elastically deform in three or four point bending, which causes the bone engaging members 2402, 2404 to spread apart. Counter-clockwise rotation of the knob 2708, the shaft 2710, or the shaft sub-assembly 2716 causes the ram 2704 or the ram sub-assembly 2714 to move proximally relative to the body 2702, reducing the proximal force of the hooks 2722, 2724 on the connecting means 2414, 2416. This allows the implant 2400 to relax toward the free state.

A surgical method for stabilizing first and second bone fragments may include any or all of the following steps in any order: assembling the punch guide 2600; assembling the inserter 2700; assembling the implant 2400 and the inserter 2400; actuating the inserter 2400; moving the ram 2704 or the ram sub-assembly 2714 distally relative to the body 2702; moving the implant 2400 from the free state to an elastically deformed state; moving the bone engaging members 2402, 2404 from a distally-converging state to a parallel state; creating a first hole in a first bone fragment; creating a second hole in a second bone fragment; creating a third hole in the first and second bone fragments; inserting the left bone engaging member 2402 in the first hole; inserting the right bone engaging member 2404 in the second hole; inserting the plug 2450 in the third hole; seating the lower surface 2410 against a surface of the first or second bone fragment; releasing the inserter 2700; moving the ram 2704 or the ram sub-assembly 2714 proximally relative to the body 2702; moving the implant 2400 from the elastically deformed state toward the free state; moving the bone engaging members 2402, 2404 from a parallel state toward a distally-converging state; and disconnecting the inserter 2700 from the implant 2400.

Creating the first and second holes may include the steps of: positioning the guide element 2512 of the drill guide 2500 against the first bone fragment; positioning the guide element 2514 against the second bone fragment so that the guide elements 2512, 2514 are on either side of an interface between the first and second bone fragments; inserting the drill bit 2550 through the first lumen 2522 of the drill guide 2500; rotating the drill bit 2550 to form the first hole in the first bone fragment; inserting the drill bit 2550 through the second lumen 2524; and rotating the drill bit 2550 to form the second hole in the second bone fragment.

Creating the third hole in the first and second bone fragments may include the steps of: inserting the peg 2618 of the punch guide 2600 in the first hole; inserting the peg 2620 in the second hole; inserting the first portion 2656 of the punch 2650 in the lumen 2616 of the punch guide 2600; advancing the punch 2650 in the lumen 2616; impacting the punch; and abutting the third portion 2664 of the punch 2650 against the proximal side 2608 of the punch guide body 2602.

Figure 23:
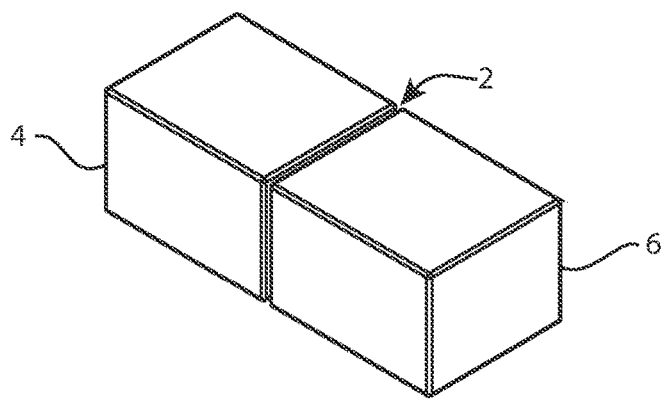
FIG. 23 is an isometric view of a joint between a first bone portion and a second bone portion.

FIG. 23 shows a joint 2 between a first bone 4 and a second bone 6.

Figure 24:
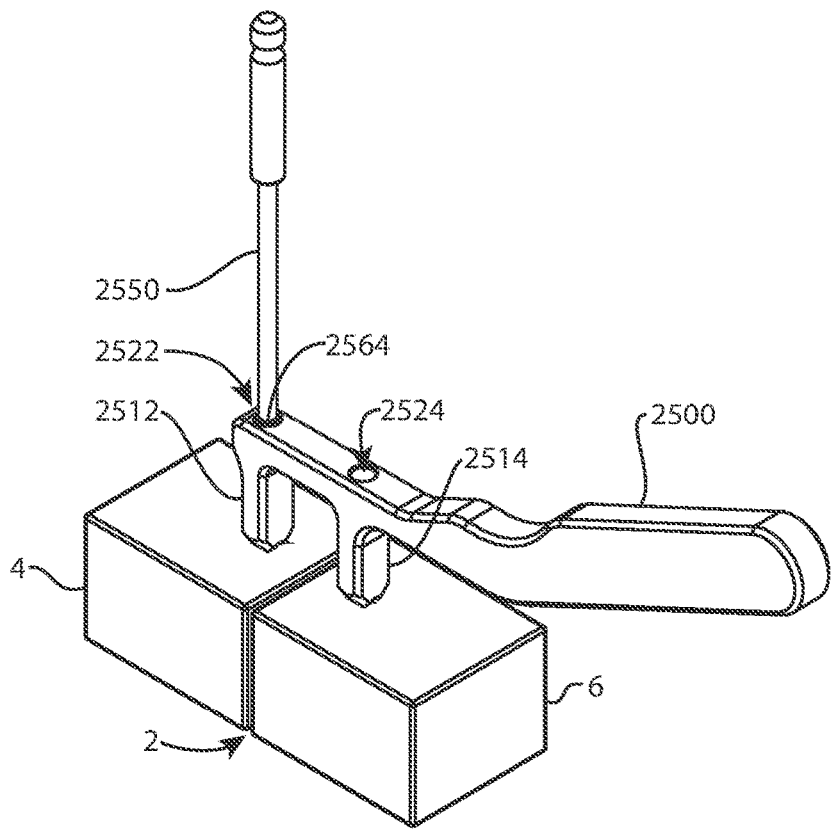
FIG. 24 is an isometric view of the joint of FIG. 23 with the drill guide of FIG. 18A positioned over the joint and the drill of FIG. 19A inserted through the drill guide.

FIG. 24 shows the steps of positioning the guide element 2512 of the drill guide 2500 against the first bone fragment 4; positioning the guide element 2514 against the second bone fragment 6 so that the guide elements 2512, 2514 are on either side of an interface 2 between the first and second bone fragments 4, 6; and inserting the drill bit 2550 through the first lumen 2522 of the drill guide 2500; rotating the drill bit 2550 to form the first hole in the first bone fragment 4.

Figure 25:
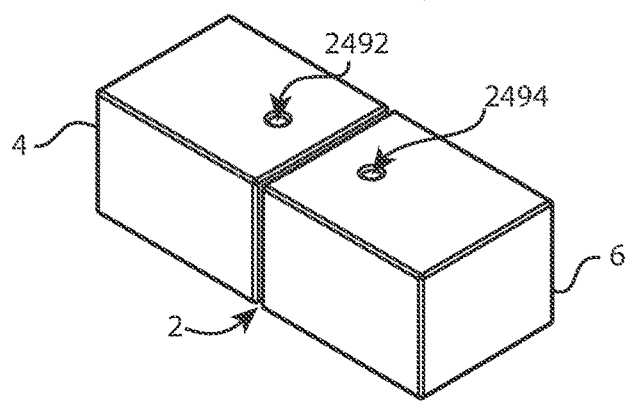
FIG. 25 is an isometric view of the joint of FIG. 24 with holes drilled in the first and second bone portions.

FIG. 25 shows the joint 2 after creating first and second holes 2492, 2494 in the first and second bone fragments 4, 6.

FIGS. 26A and 26B show the steps of inserting the peg 2618 of the punch guide 2600 in the first hole 2492; and inserting the peg 2620 in the second hole 2494.

FIGS. 27A and 27B show the steps of inserting the first portion 2656 of the punch 2650 in the lumen 2616 of the punch guide 2600; advancing the punch 2650 in the lumen 2616; impacting the punch; and abutting the third portion 2664 of the punch 2650 against the proximal side 2608 of the punch guide body 2602.

FIG. 28 shows the joint 2 after creating the third hole 2496 in the first and second bone fragments 4, 6.

Figure 29:
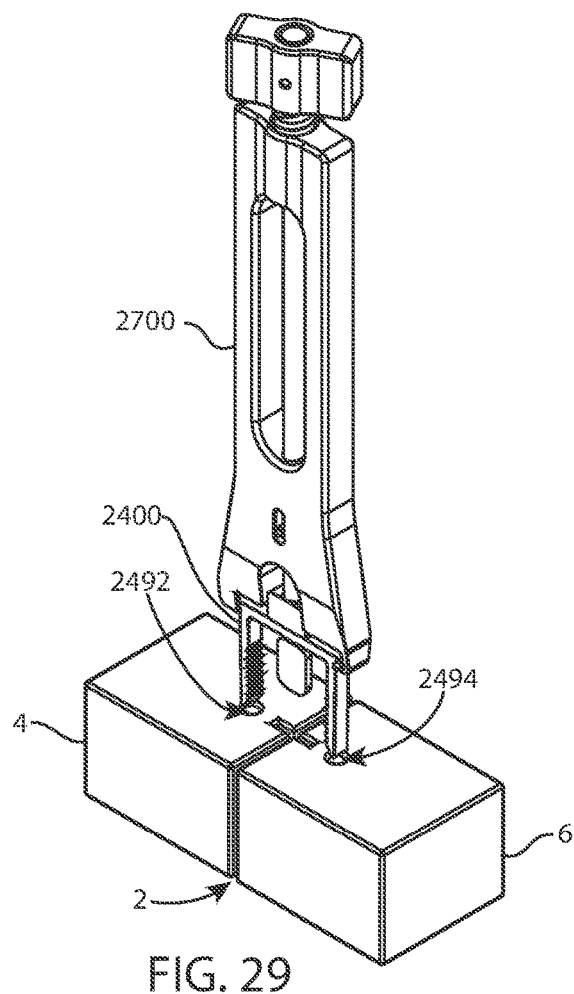
FIG. 29 is an isometric view of the joint of FIG. 28 with the implant of FIG. 17A coupled to the implant inserter of FIG. 22A, the implant in an insertion state.

FIG. 29 shows the steps of assembling the implant 2400 and the inserter 2400; actuating the inserter 2400; moving the ram 2704 or the ram sub-assembly 2714 distally relative to the body 2702; moving the implant 2400 from the free state to an elastically deformed state; moving the bone engaging members 2402, 2404 from a distally-converging state to a parallel state; inserting the left bone engaging member 2402 in the first hole 2492; and inserting the right bone engaging member 2404 in the second hole 2494.

Figure 30:
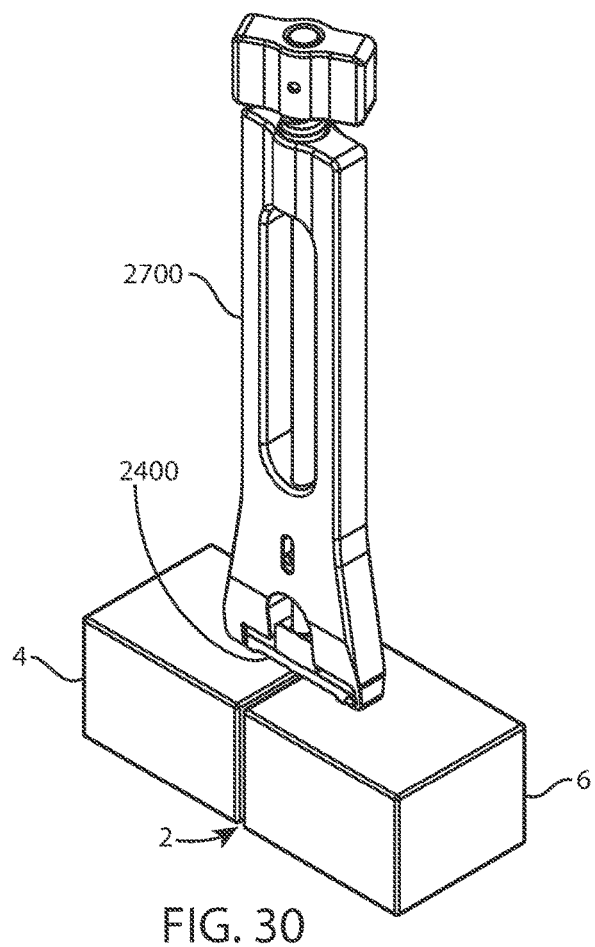
FIG. 30 is an isometric view of the joint, implant, and implant inserter of FIG. 29 with the implant inserted into the holes and slot in the first and second bone portions.
Figure 31:
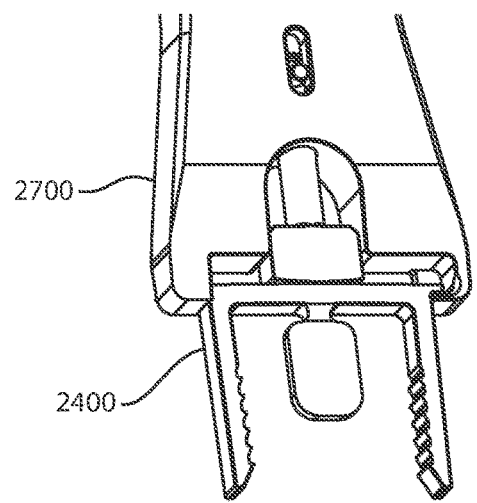
FIG. 31 is a bottom oblique view of the implant of FIG. 17A coupled to the implant inserter of FIG. 22A.

FIG. 30 shows the steps of inserting the plug 2450 in the third hole 2496; and seating the lower surface 2410 against a surface of the first or second bone fragment. FIG. 31 is an oblique detail view of the distal end of the inserter 2700 coupled to the implant 2400.

Figure 32:
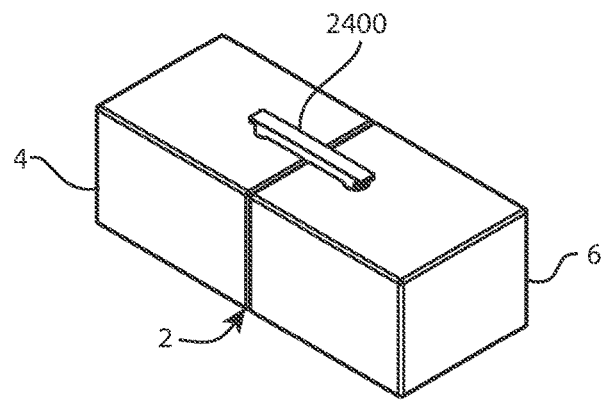
FIG. 32 is an isometric view of the joint and implant of FIG. 30 after disconnecting the implant inserter from the implant.
Figure 33:
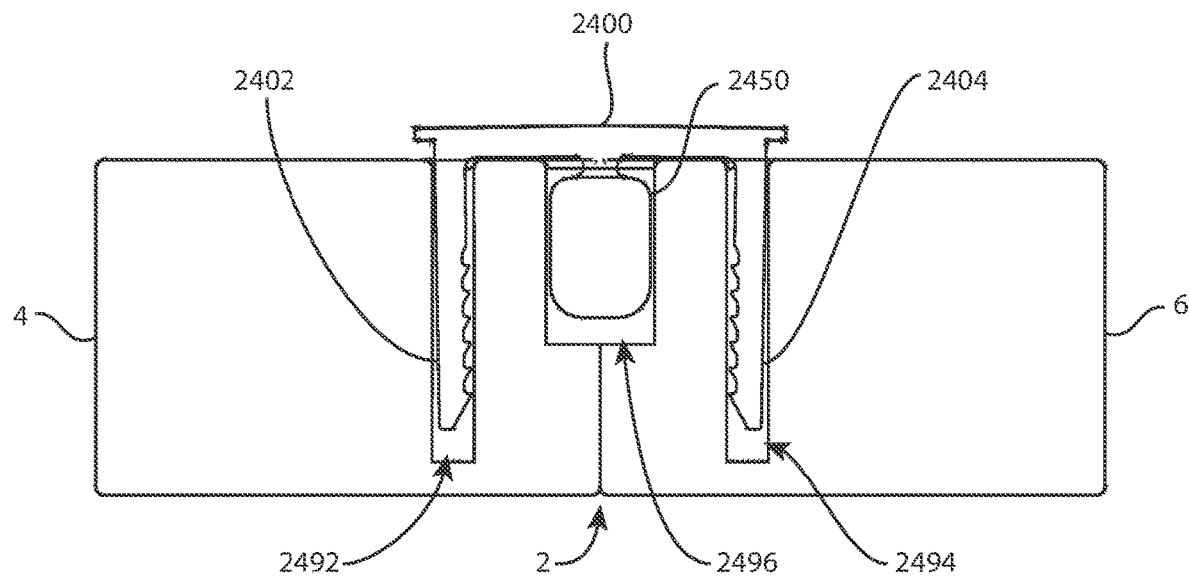
FIG. 33 is a cross-sectional view of the joint and implant of FIG. 32.

FIGS. 32 and 33 show the implant 2400 fully seated in the bone fragments 4, 6.

Figure 34:
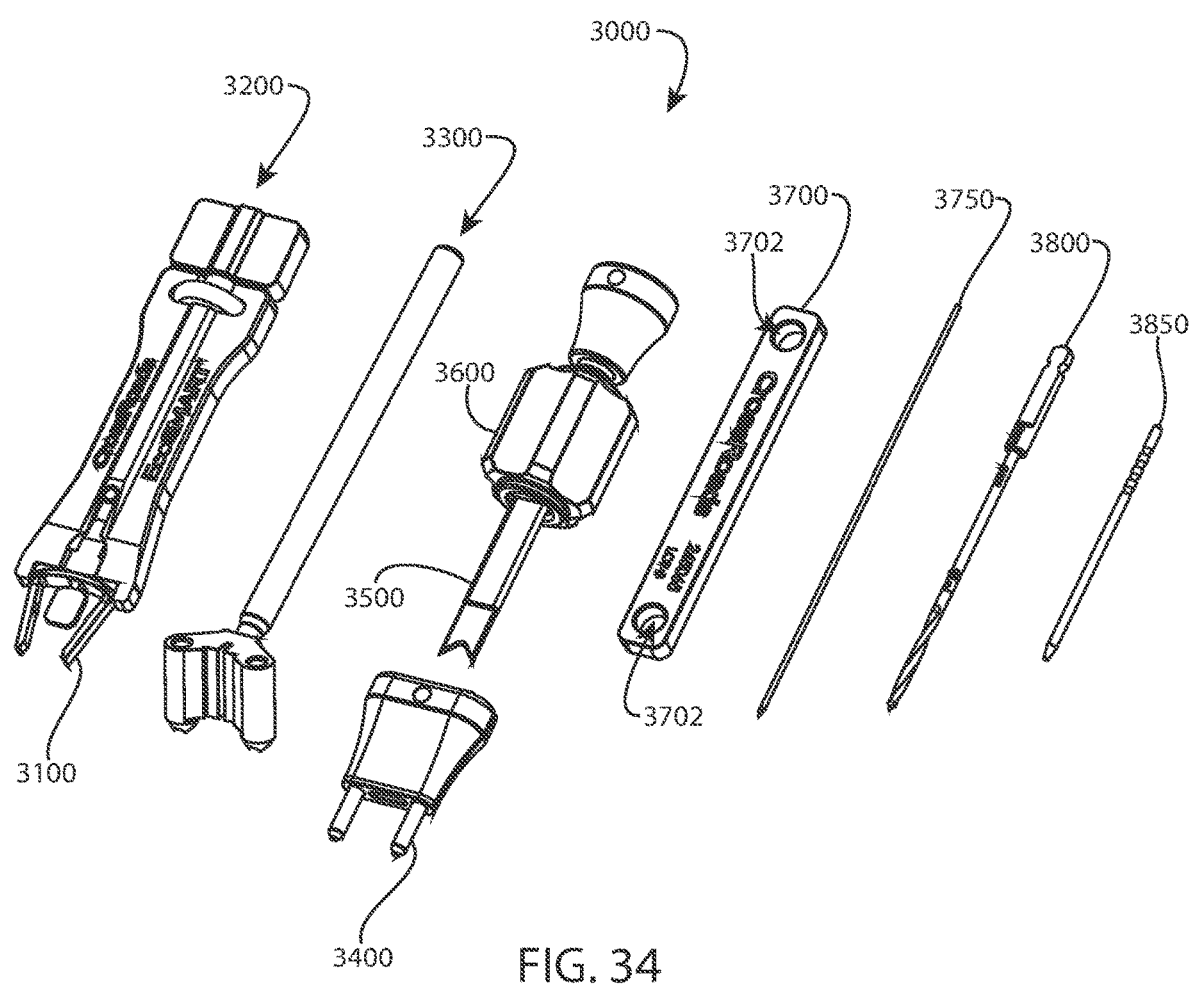
FIG. 34 is a perspective view of a system including a clip, an inserter, a drill guide assembly, a broach guide, a punch, a broach removal knob, a tamp, a k-wire, a reamer, and a bone pin.

Referring to FIG. 34, an implant and instrument system 3000 may include an implant 3100 and one or more instruments. The system 3000 is shown with an implant or clip 3100, an inserter 3200, a drill guide assembly 3300, a broach guide 3400, a punch 3500, a broach removal knob 3600, a tamp 3700, a k-wire 3750, a reamer 3800, and a bone pin 3850.

Referring to FIGS. 35-42, the clip 3100 and inserter 3200 are shown operatively assembled, with the clip 3100 in the free state, or relaxed state.

The clip 3100 includes an integrated anti-torque plug 3150. Clip 3100 and other clips disclosed herein may also be referred to as a fastener, staple, or implant. Anti-torque plug 3150 and other anti-torque features disclosed herein may also be referred to as a tab, keel, post, or implant. One or more clips 3100 may be implanted in a single procedure, for example to join two bone portions together. The clip 3100 may be similar to the implant or clip 2400.

Figure 37:
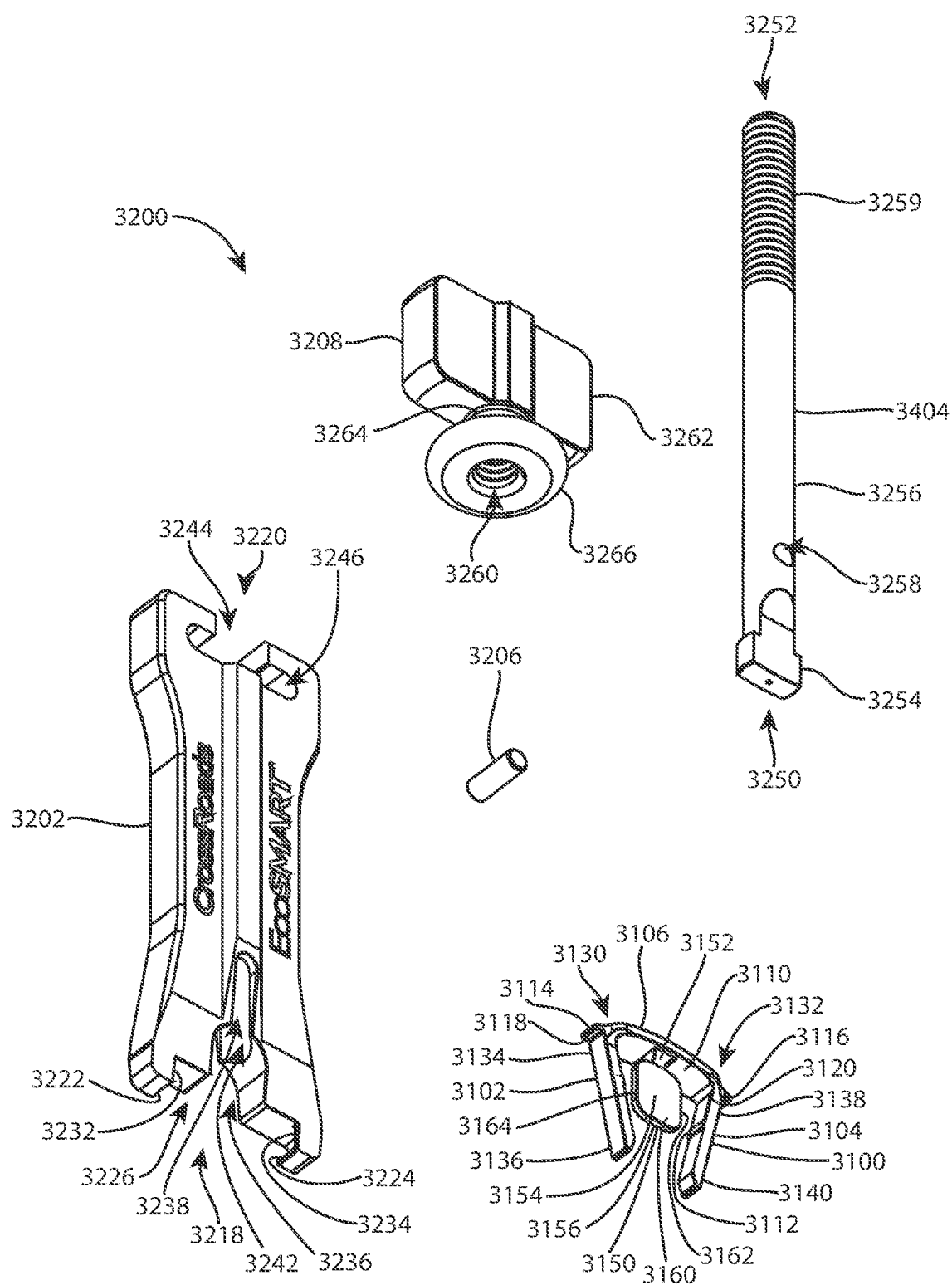
FIG. 37 is a perspective exploded view of the compression bone staple and inserter of FIG. 35.
Figure 38:
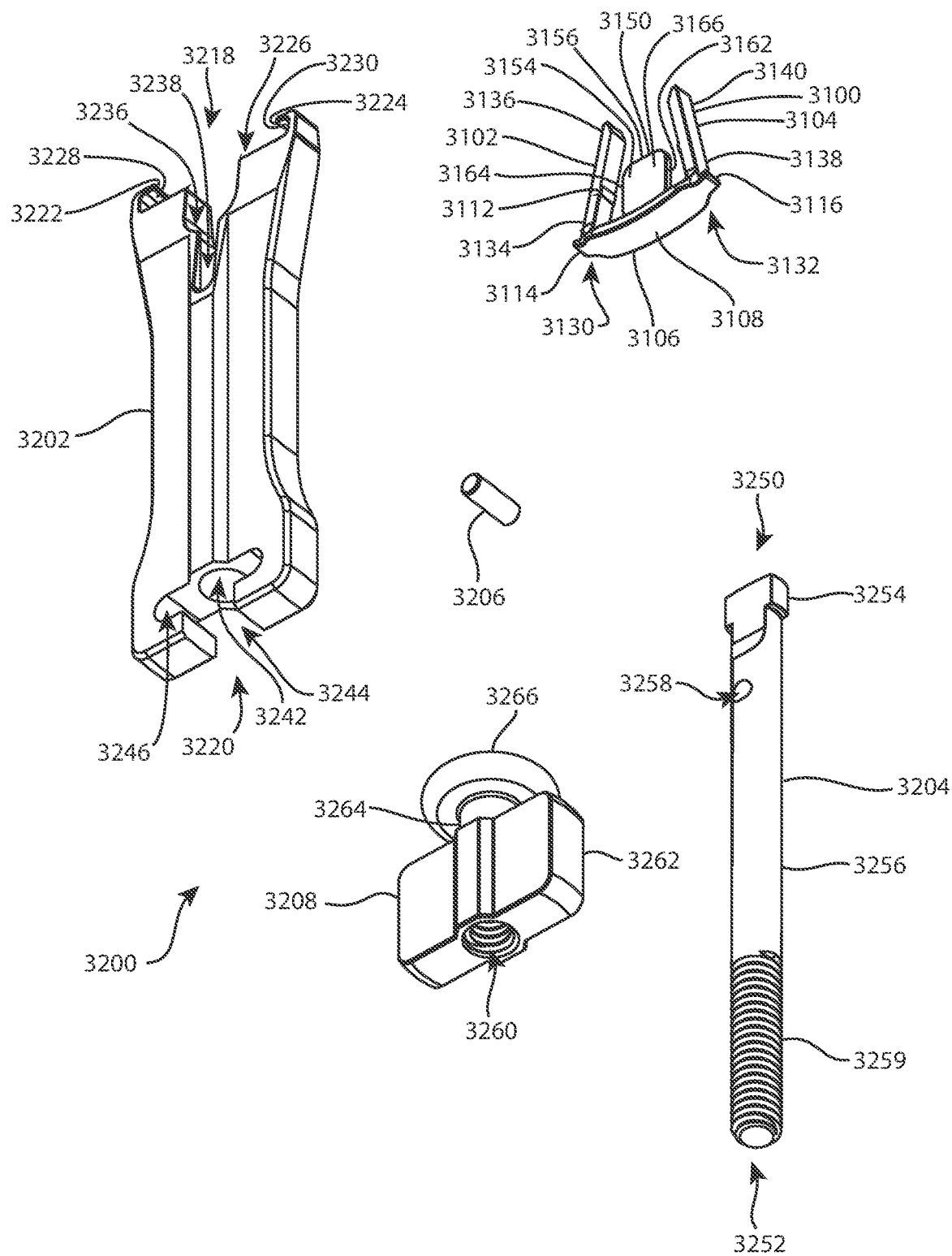
FIG. 38 is another perspective exploded view of the compression bone staple and inserter of FIG. 35 from a different direction.

Referring to FIGS. 37 and 38, the clip 3100 includes bone engaging members 3102 and 3104 which may be integral to a clip bridge 3106, also referred to as a clip body. The bone engaging members 3102 and 3104 may be referred to as legs. In other embodiments within the scope of the disclosure, a clip may include more than two bone engaging members; or alternatively may include openings for one or more independent fasteners in lieu of the bone engaging members. In other embodiments of the disclosure, the implant 3100 may be more similar to a plate. The bone engaging member 3102 extends from a left end 3130 of the clip bridge 3106 and the bone engaging member 3104 extends from an opposite right end 3132 of the clip bridge 3106. Bone engaging member 3102 has a proximal end 3134 attached to the left end 3130 of the clip bridge 3106 and an opposite distal end 3136 which is a free end. Bone engaging member 3104 has a proximal end 3138 attached to the right end 3132 of the clip bridge 3106 and an opposite distal end 3140 which is a free end. Clip bridge 3106 has at least one upper or proximal surface 3108 and at least one lower or distal surface 3110. The lower surface 3110 may be referred to as a bone facing surface. Bone engaging member 3102 extends from the lower surface 3110 beside bone engaging member 3104. The bone engaging members 3102 and 3104 may have features 3112 that may improve bone purchase or improve pull out strength of the clip 3100 from bone or soft tissue. The features 3112 may be referred to as teeth or serrations. The features 3112 may be on facing sides of the bone engaging members 3102, 3104 or on any or all sides of the bone engaging members. The clip 3100 may have projections or other connecting means 3114 and 3116 for connection with a means of insertion. The connecting means 3114, 3116 may be referred to as tabs, ears, protrusions, wings, retainers, or retaining members. The connecting means 3114 and 3116 are shown extending sideways outwardly from the left and right ends 3130, 3132 of the bridge 3106, respectively, along a longitudinal direction established by the bridge. In other embodiments, the connecting means may project perpendicularly with respect to the bridge. The connecting means 3114 and 3116 may have lower or distal surfaces 3118 and 3120 respectively that may releasably engage with a means of insertion that may allow an inserter or other means of insertion to be side loading, top loading or pivotably loaded. For example, an inserter for clip 3100 may be side loading or pivotably loading. The lower surfaces 3118, 3120 may be referred to as bone facing surfaces. Referring to FIG. 41, the lower surfaces 3118, 3120 are proximally spaced apart from, or proximally offset from, the lower surface 3110. The dashed extension lines 3110' and 3110" in FIG. 41 show the level of the lower surface 3110 versus the lower surfaces 3118, 3120.

Figure 39:
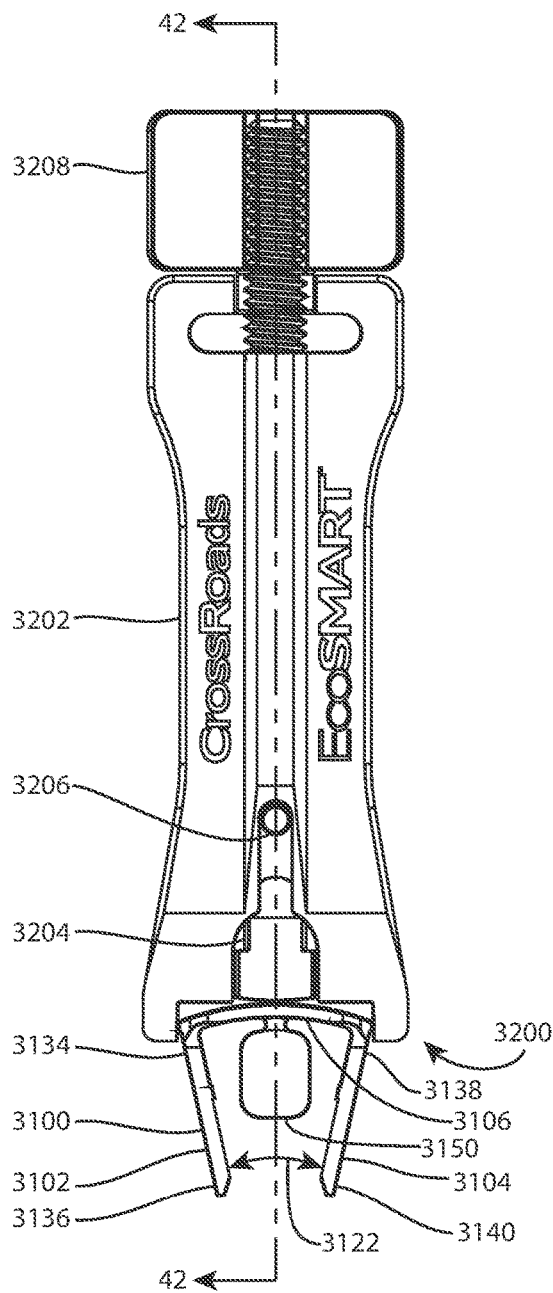
FIG. 39 is a front view of the compression bone staple and inserter of FIG. 35.
Figure 40:
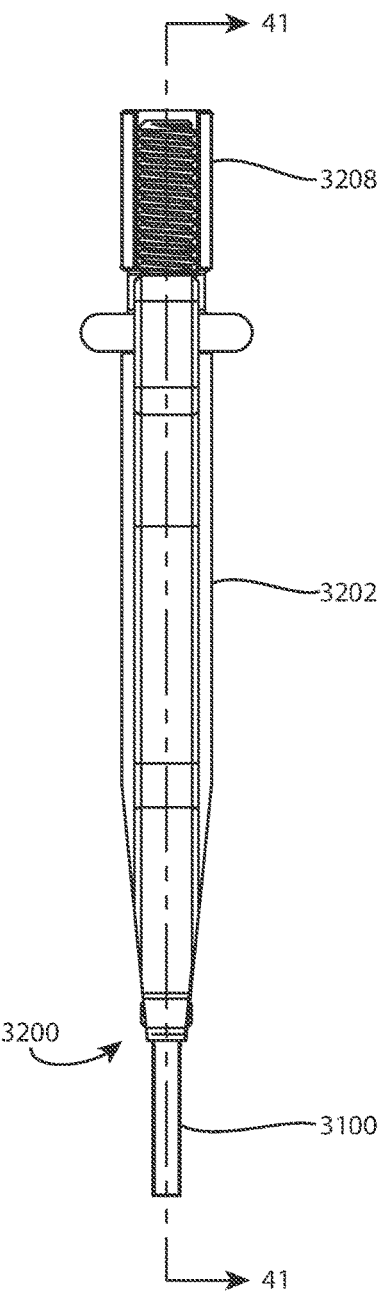
FIG. 40 is a right view of the compression bone staple and inserter of FIG. 35.

An integrated anti-torque plug 3150 projects distally from the lower surface 3110 of bridge 3106. In the embodiment depicted, a single plug 3150 is centered between bone engaging members 3102, 3104; in other embodiments the plug may be off-center relative to the members 3102, 3104, and/or a plurality of plugs may be included. The plug may also be connected to the implant 3100 in more than one location along the lower surface 3110 of bridge 3106. Plug 3150 includes a neck portion 3152 where the plug is joined to bridge 3106, a body 3154, and a tip 3156. Neck portion 3152 may be formed as a waist having a reduced width with respect to the plug body 3154 as shown in FIG. 39; in other embodiments the neck portion 3152 may be wider than or equal in width with respect to the plug body 3154. Preferably, plug 3150 is connected to the clip 3100 only via the bridge 3106, and not along the bone engaging members 3102, 3104. Plug 3150 may be rectangular in cross-section and includes four sides 3160, 3162, 3164, 3166. Plug 3150 may have another elongated cross-sectional shape, such as oval, polygonal, elliptical, etc., The plug thickness between sides 3160 and 3166 may be less than, the same as, similar to, or greater than the thickness of the bridge 3106 and/or bone engaging members 3102, 3104 of the clip 3100 in the same direction (front-back). Preferably, the plug thickness between sides 3160 and 3166 is less than the thickness of the bridge and bone engaging members 3102, 3104 in the same direction, as seen best in FIG. 42. Preferably, the thickness of the bridge 3106 is greater than the thickness of the bone engaging members 3102, 3104, as seen best in FIG. 42; referring to FIG. 38, the bridge 3106 may decrease in thickness toward the left and right ends 3130, 3132 and connecting means 3114, 3116. The major front-back dimension of the bridge 3106 may be 5 mm, the front-back dimension of the connecting means 3114, 3116 may be 2.7 mm, and the front-back dimension of the plug 3150 between sides 3160 and 3166 may be 1 mm. The plug tip 3156 may be tapered on at least two sides 3162, 3164 with respect to the plug body to facilitate insertion into a joint. The plug sides 3160, 3162, 3164, 3166 may be smooth as seen in FIGS. 37 and 38; in other embodiments one or more plug sides may include teeth, serrations, or other surface roughening. In other embodiments, the plug may have a differently shaped cross-section. The plug does not preclude compression of the bone segments by the bone engaging members 3102, 3104, at least because the elongated cross-section of the plug 3150 is oriented in a plane coplanar with, or parallel to, the plane of the bridge 3106 and bone engaging members 3102, 3104 of the clip 3100, as shown in FIGS. 41 and 42. In other words, the cross-section of the plug 3150 is elongated along a direction parallel to, or colinear with, a line extending between the bone engaging members 3102, 3104.

A means of insertion may maintain the clip 3100 in a first configuration thereby allowing a second configuration once an inserter is disassembled from the implant. The first configuration may be an elastically deformed state, for example an insertion state. The second configuration may be a free state or an implanted state, as seen in FIG. 39. The means of insertion may utilize features similar to connecting means 3114 and 3116 in combination with other surfaces such as top surface 3108. This combination of means of insertion may be used to maintain one or more features or arms or projections in a particular configuration. This combination of means of insertion may create a bending modality, such as a three point or four point bend, to maintain a specific clip device configuration or combination of configurations. A combination of surfaces and means of insertion, such as connecting means 3114, may be used on the entire clip or portions of a clip to create or maintain a particular configuration of a clip. For example, a tab such as 3114 and top surface, such as 3108 may be used to maintain one side of a clip or one leg of a clip in a particular configuration. When disassembled, that leg may have a configuration that is different from or the same as the configuration of the rest of the clip.

Referring to FIG. 39, the clip 3100 is shown in the free state, or relaxed state, which is the shape of the clip 3100 when no external forces are acting upon the clip 3100, other than gravity; the clip 3100 experiences no elastic or plastic deflection or deformation. In the free state, the bone engaging members 3102 and 3104 converge as they extend away from the bridge 3106 so that the distal ends 3136, 3140 are closer together than are the proximal ends 3134, 3138. An angle 3122 is formed between the converging bone engaging members 3102 and 3104 in the free state. The angle 3122 opens toward the bridge 3106. The angle 3122 may be referred to as a free state angle.

The inserter 3200 may be used with any of the implants or clips disclosed herein. The inserter 3200 may include a body 3202, a ram or shaft 3204, a pin 3206, and a knob 3208. The inserter 3200 may be similar to inserter 2700. The ram 3204 and the ram pin 3206 may be coupled together as a ram sub-assembly 3214.

The body 3202 extends between a distal end 3218 and a proximal end 3220. The body 3202 may be a generally plate-like part that is wider at the distal and proximal ends 3218, 3220 and narrower in between. The distal-most aspect of the body 3202 may include two jaws or hooks 3222, 3224 that face each other across a shallow alcove 3226. The hooks 3222, 3224 include proximal surfaces 3228, 3230, respectively. The hooks 3222, 3224 include front walls 3232, 3234, respectively. A first notch 3236 extends proximally from a central portion of the alcove 3226. A second notch 3238 extends proximally from a central portion of the first notch 3236. The second notch 3238 is narrower than the first notch 3236. A central longitudinal hole 3242 extends proximally through the body 3202 between the distal and proximal ends 3218, 3220. The body 3203 may be thickened in the vicinity of the hole 3242 so as to adequately support the hole 3242 under expected loads. A third notch 3244 extends distally into a central portion of the proximal end 3220 and intersects a transverse slot 3246 that extends between the front and back sides of the body 3202.

The ram or shaft 3204 extends between a distal end 3250 and a proximal end 3252. The ram 3204 includes a distal head 3254, which may be generally rectangular as shown. As seen best in FIGS. 39 and 41, the distal-most aspect of the head 3254 may be convex in a front or back view. A shaft 3256 extends proximally from the head 3254. The shaft 3256 may have a circular cross section as shown. The outer diameter of the shaft 3256 may be greater than the thickness of the head 3254 in a front-back direction, and may be less than the width of the head in a left-right direction, as seen best in FIGS. 41 and 42. A transverse hole 3258 extends through the shaft 3256 proximal to the head 3254. The proximal end 3252 of the ram 3204 may include external threads 3259.

The ram 3204 and the ram pin 3206 may be coupled together to form the ram sub-assembly 3214 by inserting the ram pin through the hole 3258. The ram pin 3206 may be fixed within the hole 3258 by a press fit, swaging operation, welding or brazing operation, or the like.

The knob 3208 may include a generally rectangular body 3262 which may be contoured to match the proximal end 3220 of the body 3202. A central longitudinal internally threaded hole 3260 may extend through the knob 3208 along a proximal-distal direction. The knob 3208 may include a first shaft portion 3264 extending distally from the body 3262 concentric with the hole 3260. The outer diameter of the first shaft portion 3264 may be less than the outer dimensions of the body 3262 in a front, back, left, or right view. A second shaft portion 3266 may extend distally from the first shaft portion 3264 concentric with the hole 3260. The outer diameter of the second shaft portion 3266 may be greater than the outer diameter of the first shaft portion 3264.

The inserter 3200 may be assembled by coupling the knob 3208 to the body 3202 so that the first shaft portion 3264 is in the third notch 3244 and the second shaft portion 3266 is in the transverse slot 3246; inserting the ram pin 3206 into the hole 3258 of the ram 3204 to form the ram sub-assembly 3214; inserting the proximal end 3252 of the ram into the distal end of the hole 3242 of the body 3202; advancing the ram proximally until the proximal end 3252 reaches the knob 3208; and engaging the external and internal threads 3259, 3260 so that the head 3254 is received in the first notch 3236 and the pin 3206 is received in the second notch 3238.

When the inserter 3200 is assembled, the ram 3204, pin 3206, and knob 3208 are captive to the body 3202. Clockwise and counterclockwise rotation of the knob 3208 causes the ram 3204 to translate along the proximal-distal direction. The pin 3206 in the second notch 3238 prevents the ram 3204 from rotating and limits the proximal travel of the ram. However, there is no limit to the distal travel of the ram in this embodiment, so that the inserter 3200 is readily disassembled for cleaning.

The clip 3100 and inserter 3200 may be operatively assembled by turning the knob 3208 to move the ram 3204 proximally so that the distal aspect of the head 3254 is within the first notch 3236; sliding the hooks 3222, 3224 over the connecting means 3114, 3116; and turning the knob 3208 to move the ram 3204 distally so that the distal aspect of the head 3254 contacts the bridge 3106. The connecting means 3114, 3116 may contact the front walls 3232, 3234.

When the clip 3100 and inserter 3200 are operatively assembled, clockwise and counterclockwise rotation of the knob 3208 causes the bridge 3106 to move between an elastically deformed state and a relaxed state, or free state. In the elastically deformed state, the distal aspect of the head 3254 presses against the proximal surface 3108 of the bridge 3106, flattening the bridge against the resistance of the connecting means 3114, 3116 in the hooks 3222, 3224 and spreading apart the free ends 3136, 3140 of the bone engaging members 3102, 3104. In the relaxed state, the distal aspect of the head 3254 may be spaced apart from the proximal surface 3108 of the bridge 3106, or may contact the proximal surface 3108 so lightly that the bridge remains undeformed.

Referring to FIGS. 43-45, the drill guide assembly 3300 may include a handle 3302 and a guide 3304. The drill guide assembly 3300 may be similar to the drill guide 2500. The drill guide assembly 3300 may be used to prepare holes in a first bone 4 and a second bone 6 on either side of a joint 2. The joint 2 may be an anatomical joint, an osteotomy, a fracture, or an interface between the first and second bones 4, 6.

The handle 3302 necks down to an externally threaded distal tip 3306, seen in FIG. 45.

The guide 3304 includes first and second guide elements 3312, 3314. The first guide element 3312 surrounds and supports a first lumen 3322, while the second guide element 3314 surrounds and supports a second lumen 3324. In the embodiment shown, the first and second lumens 3322, 3324 are coplanar. In other embodiments, the lumens may not be coplanar. Each guide element 3312, 3314 includes a pointed or tapered distal tip to facilitate engagement with bone or tissues during use. The guide elements 3312, 3314 are carried by a generally Y- or V-shaped body 3310. A linear slot 3316 extends in a plane perpendicular to the plane of the first and second lumens 3322, 3324, and is located halfway between the first and second lumens. The slot 3316 may be replaced by a hole, a lumen, a ring, or the like. An internally threaded hole 3326 extends into the body 3310 opposite the slot 3316.

The drill guide assembly 3300 may be assembled by threading the distal tip 3306 of the handle 3302 into the hole 3326 of the guide 3304. When the drill guide assembly 3300 is assembled, the handle 3302 and guide 3304 may be rigidly fixed together.

Figure 46:
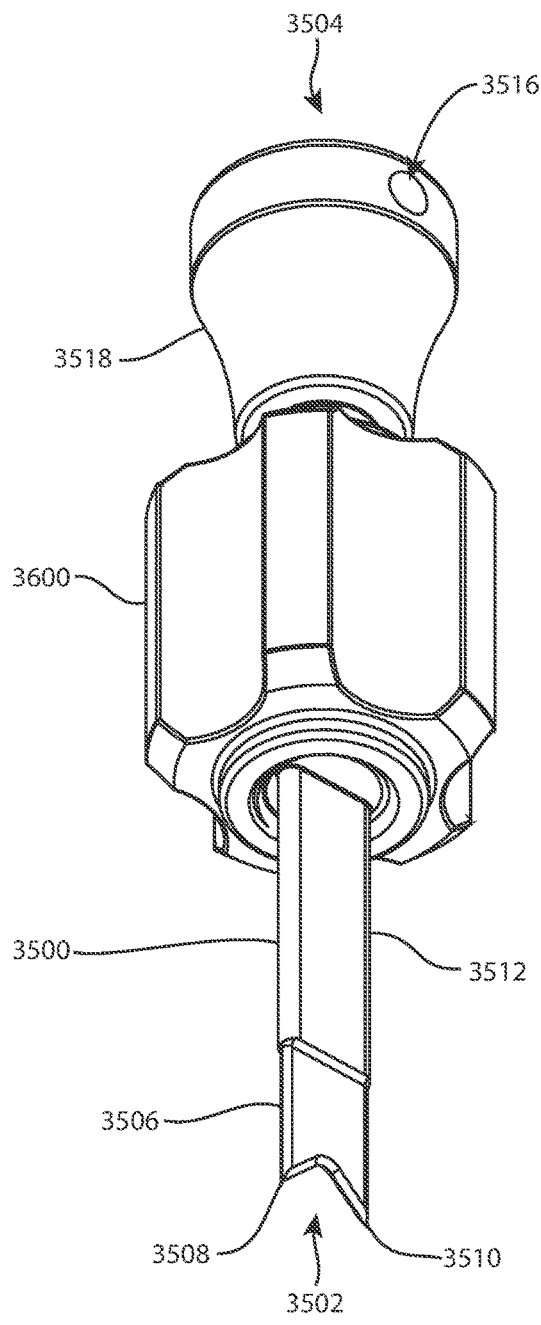
FIG. 46 is a perspective view of the punch and broach removal knob of FIG. 34 operatively assembled together.
Figure 47:
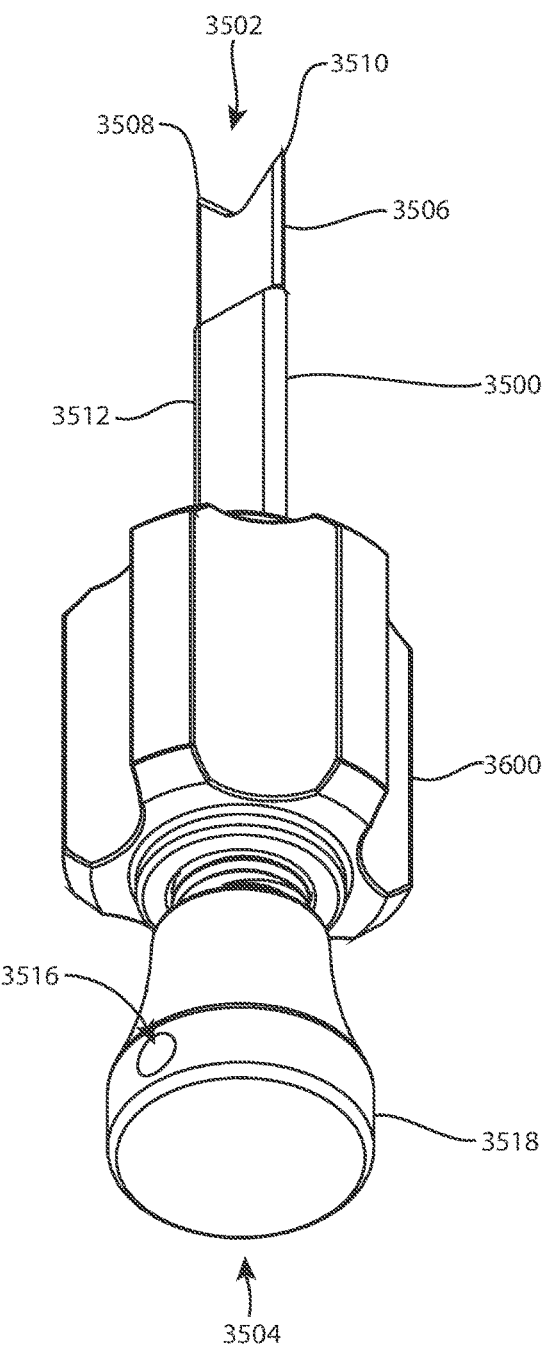
FIG. 47 is another perspective view of the punch and broach removal knob of FIG. 46 from a different direction.
Figure 48:
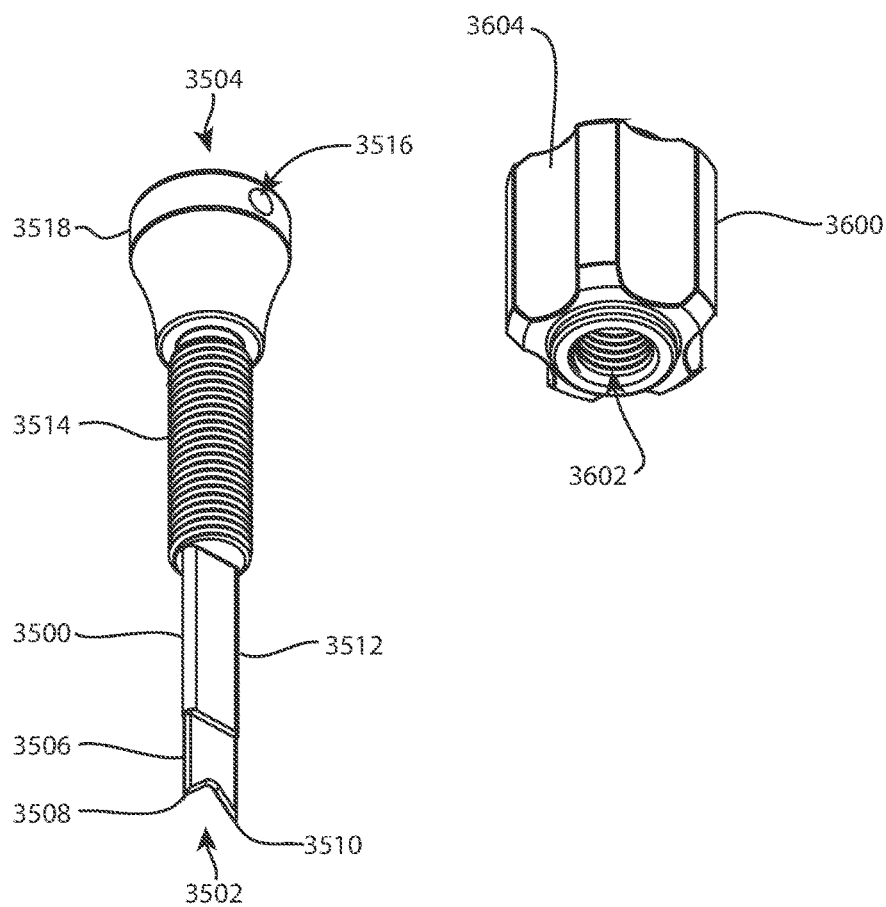
FIG. 48 is a perspective exploded view of the punch and broach removal knob of FIG. 46.

Referring to FIGS. 46-48, the punch 3500 and broach removal knob 3600 are shown operatively assembled in FIGS. 46 and 47, and separated in FIG. 48.

The punch 3500 extends between a distal end 3502 and a proximal end 3504. The punch 3500 may include four portions or segments along its distal-proximal length. A first portion 3506 may extend proximally from the distal end 3502. The first portion 3506 may have an elongated cross-sectional shape. The distal-most aspect of the first portion 3506 may be sharpened or pointed to penetrate bone. Two points 3508, 3510 are shown, with a distal sharp concave profile between the points. A second portion 3512 may extend proximally from the first portion 3506. The second portion 3512 may have the same cross-sectional shape as the first portion, outwardly offset so that the second portion is wider and/or thicker than the first portion. A third portion 3514 may extend proximally from the second portion 3512. The third portion 3514 may have external threads. A fourth portion 3518 may extend proximally from the third portion 3514. The fourth portion 3518 may increase in diameter toward the proximal end 3504. The fourth portion 3518 may function as a handle and a strike platform to impact the punch 3500 distally into bone. A transverse hole 3516 may extend through the thickness of the punch 3500 in the fourth portion 3518.

The broach removal knob 3600 is a cylindrical part with a central longitudinal internally threaded hole 3602. The outer diameter of the broach removal knob 3600 may include a grip feature, such as the circular array of longitudinal grooves shown, knurling, flats, or the like.

The punch 3500 and broach removal knob 3600 may be operatively assembled by threading the third portion 3514 of the punch 3500 into the hole 3602 of the broach removal knob 3600.

Figure 49:
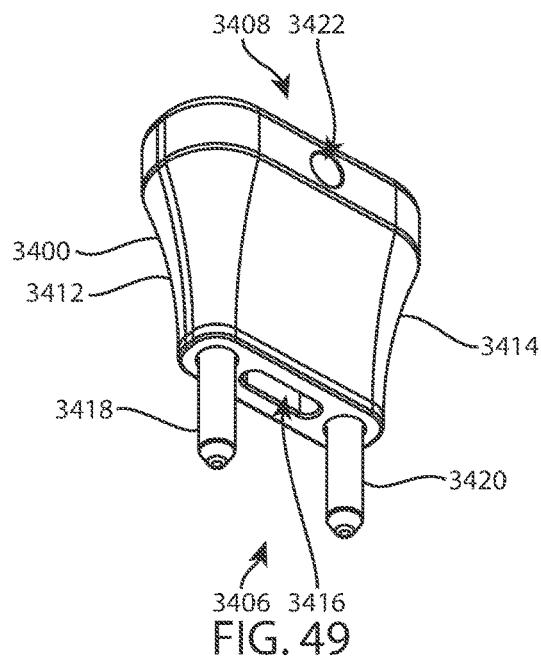
FIG. 49 is a perspective view of the broach guide of FIG. 34.
Figure 50:
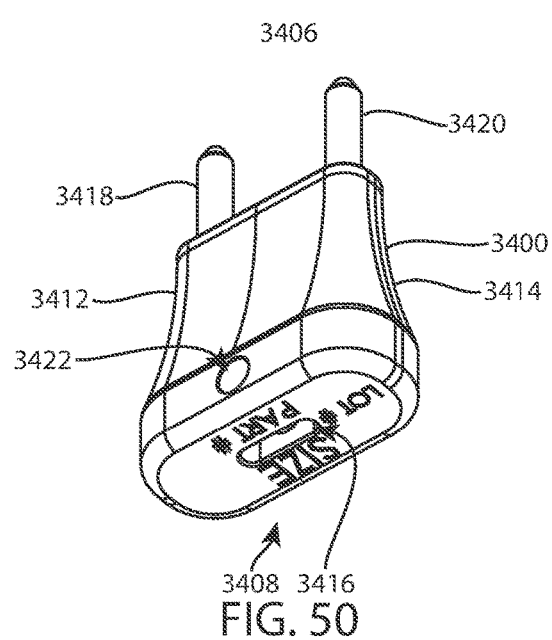
FIG. 50 is another perspective view of the broach guide of FIG. 34 from a different direction.

Referring to FIGS. 49-50, the broach guide 3400 may be a generally rectangular shape with a distal side 3406, a proximal side 3408, a left side 3412, and a right side 3414. The broach guide 3400 may be similar to the punch guide 2600, and may be referred to as a punch guide itself. A lumen 3416 extends through the broach guide 3400 between the distal and proximal sides 3406, 3408. The lumen 3416 may have a transverse cross section that is elongated in a left-right direction as shown. The cross-sectional shape may be rectangular, oval, snowman, or another shape. An oval shape is shown. The lumen 3416 may be sized and shaped to receive the first and second portions 3506, 3512 of the punch 3500. The lumen 3416 may be centered in the left-right width of the broach guide 3400. Bilateral pegs 3418, 3420 extend distally from the distal side 3406 to the left and right of the lumen 3416. The pegs 3418, 3420 may have distal tapered or pointed tips as shown in FIG. 49. The pegs may be separate parts or integrally formed with the broach guide 3400. The pegs 3418, 3420 fit into the holes in the first and second bones 4, 6 made using the drill guide assembly 3300. A transverse hole 3422 may extend through the broach guide 3400 along a front-back direction, and may be centered in the left-right width of the broach guide 3400 near the proximal end 3408. The hole 3422 may intersect the lumen 3416.

The punch 3500, with attached broach removal knob 3600, and broach guide 3400 may be operatively assembled by inserting the first portion 3506 of the punch 3500 into the lumen 3416 at the proximal side 3408 of the broach guide 3400 and advancing the punch 3500 distally until the distal end of the third portion 3514 contacts the proximal side 3408 of the broach guide 3400 and at least a distal portion of the first portion 3506 protrudes from the distal end of the lumen 3416. Preferably, the broach removal knob 3600 is assembled to the punch 3500 in contact with the distal end of the fourth portion 3518.

When the punch 3500, broach removal knob 3600, and broach guide 3400 are operatively assembled, the punch 3500 may be advanced distally through the broach guide 3400 to prepare a slot across the joint 2 between the first and second bones 4, 6. The broach removal knob 3600 may be rotated relative to the punch 3500 to move the broach removal knob distally to push against the broach guide 3400 to push the punch 3500 proximally out of the bones 4, 6 and the broach guide.

Referring to FIG. 34, the tamp 3700 may be an elongated generally rectangular solid part with a hole 3702 through each end. The tamp 3700 may be employed to push the implant 3100 farther into the first and second bones 4, 6 after the inserter 3200 has been disconnected from the implant 3100.

The k-wire 3750 is sized to be received in the slot 3316 of the drill guide assembly 3300. The k-wire 3750 may be replaced by a bone pin, drill bit, reamer, peg, rod, shaft, dowel, and the like. The k-wire 3750 may be replaced by a part having a non-circular transverse cross section, such as an oval or rectangular cross section, similar to the tamp 3700. This may be advantageous when the part is inserted into the joint 2, as such a part will tend to orient itself with the major cross-sectional dimension oriented along the joint 2. When the part is received in a complementary slot 3316, the drill guide assembly 3300 will be oriented more precisely perpendicular to the joint 2, and subsequently the broach guide 3400, punch 3500, and implant 3100 will be oriented more precisely perpendicular to the joint 2.

The reamer 3800 and the bone pin 3850 are sized to be received in either lumen 3322, 3324 of the drill guide assembly 3300.

A surgical method for using the system 3000 to stabilize first and second bone fragments may include any or all of the following steps in any order:

Inserting the k-wire 3750 into a desired location for implant 3100 placement relative to the joint 2 and the first and second bones 4, 6. The k-wire 3750 indicates where the midpoint of the plug 3150 will be located when the implant 3100 is inserted. The k-wire 3750 may be inserted in the joint 2 between first and second bones 4, 6 so that the plug 3150 will be centered across the joint 2.

Positioning the drill guide assembly 3300 relative to the joint 2, the first and second bones 4, 6, and the k-wire 3750 so that the distal tip of the first guide element 3312 is against the first bone 4, the distal tip of the second guide element 3314 is against the second bone 6, and the slot 3316 receives the k-wire 3750.

Actuating the reamer 3800 through the first lumen 3322 to make a hole in the first bone 4, removing the reamer, and optionally inserting the bone pin 3850 into the prepared hole in the first bone 4.

Actuating the reamer 3800 through the second lumen 3324 to make a hole in the second bone 6, and removing the reamer, drill guide assembly 3300, and k-wire 3750.

Inserting the pegs 3418, 3420 of the broach guide 3400 into the holes in the first and second bones 4, 6 and advancing the broach guide 3400 against the first and second bones 4, 6.

Threading the broach removal knob 3600 onto the third portion 3514 of the punch 3500 and into contact with the distal end of the fourth portion 3518.

Inserting the first portion 3506 of the punch 3500 into the proximal end of the lumen 3416 of the broach guide 3400 and advancing the punch 3500 distally until the distal end of the third portion 3514 contacts the proximal side 3408 of the broach guide 3400. The punch 3500 may be advanced by impacting the proximal end of the fourth portion 3518 with a mallet. The punch 3500, broach guide 3400, and plug 3150 may be dimensioned relative to each other so that when the distal end of the third portion 3514 contacts the proximal side 3408, the first portion 3506 protrudes from the distal end of the lumen 3416 a distance that corresponds to the location of the tip 3156 of the plug 3150 when the implant 3100 is inserted. Thus, the punch 3500 forms a slot in the first and second bones 4, 6 across the joint 2 (or across the desired location as established by the k-wire 3750).

Removing the punch 3500, broach removal knob 3600, and broach guide 3400 from the first and second bones 4, 6. The broach removal knob 3600 may be rotated relative to the punch 3500 to move the broach removal knob distally to push against the broach guide 3400 to push the punch 3500 proximally out of the bones 4, 6 and the broach guide, if needed. The bone pin 3850 may be inserted into the hole 3516 of the punch 3500 or the hole 3422 of the broach guide 3400 to aid in removal, if needed.

Coupling the implant 3100 to the inserter 3200. This step may include turning the knob 3208 to move the ram 3204 proximally so that the distal aspect of the head 3254 is within the first notch 3236; sliding the hooks 3222, 3224 over the connecting means 3114, 3116; and turning the knob 3208 to move the ram 3204 distally so that the distal aspect of the head 3254 contacts the bridge 3106. The connecting means 3114, 3116 may contact the front walls 3232, 3234.

Moving the implant 3100 to the elastically deformed state. This step may include turning the knob 3208 to move the ram 3204 distally to press against the proximal surface 3108 of the bridge 3106 to flatten the bridge against the resistance of the connecting means 3114, 3116 in the hooks 3222, 3224, thereby spreading apart the free ends 3136, 3140 of the bone engaging members 3102, 3104. Preferably, the bone engaging members 3102, 3104 are substantially parallel in the elastically deformed state, in other words parallel in the view of the user.

Inserting the bone engaging members 3102, 3104 into the holes in the first and second bones 4, 6, inserting the plug 3150 into the slot in the first and second bones 4, 6, and advancing the implant 3100 into the first and second bones 4, 6 until the distal surface 3110 of the bridge 3106 is flush against the first and second bones 4, 6.

Allowing the implant 3100 to move toward the relaxed state, or free state. This step may include turning the knob 3208 to move the ram 3204 proximally away from the bridge 3106.

Disconnecting the inserter 3200 from the implant 3100. This step may include sliding the inserter 3200 along a front-back direction off of the connecting means 3114, 3116.

Optionally advancing the implant 3100 farther into the first and second bones 4, 6 after the inserter 3200 has been disconnected from the implant 3100. This step may include placing one end of the tamp 3700 against the bridge 3106 and impacting the opposite end of the tamp with a mallet.

Referring to FIGS. 51-55, another embodiment of an implant with an associated keel is shown. Implant 4000 includes a plate 4002 and the clip 200 (FIGS. 2A and 2B). The implant 4000 may also include one or more fasteners, such as the two bone screws 2280 shown. The implant 4000 may be similar to implant 2200 or assembly 100 disclosed in U.S. patent application Ser. No. 15/209,623, which is incorporated herein by reference in its entirety.

The plate 4002 has an obverse side 4012 and a reverse side 4014. When the plate 4002 is implanted, the obverse side 4012 faces away from the first and second bones 4, 6 and the reverse side 4014 faces toward the first and second bones. The plate 4002 includes several holes 4016 which extend through the plate 4002 between the obverse and reverse sides 4012, 4014. Three holes 4016 are illustrated, although any number of holes may be present. Each hole 4016 may include an internally threaded portion 4018 and/or a non-threaded portion 4020 so that each hole 4016 may accept a locking screw or a non-locking screw. The internally threaded portion 4018 may be adjacent to the reverse side 4014. The non-threaded portion 4020 may be adjacent to the obverse side 4012. The non-threaded portion 4020 may be concave and/or elongated. One end of the plate 4002 is shown with an optional hole 4021 with a concave elongated non-threaded portion 4020 and no internally threaded portion. An optional groove 4022 in the obverse side 4012 extends between two of the holes 4016, and slightly beyond each of the holes. Each of these two holes 4016 is also elongated toward the other hole 4016, leaving a web 4024 extending between the two holes 4016. The web 4024 may be adjacent to the reverse side 4014. The web 4024 separates the two holes 4016, and may be present even if the holes 4016 are not elongated towards each other. The optional groove 4022 if present, the two holes 4016 (elongated or not), and the web 4024 are referred to collectively as a receiver 4026, and the involved holes 4016 are referred to as receiver holes 4028. A receiver 4026 may be included between any two holes through a plate. Multiple receivers may be included on a single plate. For example, the plate 4002 may be modified to include a second receiver between the left two holes 4016 and/or a third receiver between the right two holes 4016. Two receivers 4026 may share a common receiver hole 4028. The plate 4002 may be much more stiff than the dynamic element, which in this example is the clip or staple 200. The plate 4002 may be rigid or static. Alternatively, the plate 4002 may be malleable or elastic. The plate 4002 may include rigid and malleable regions.

Figure 51:
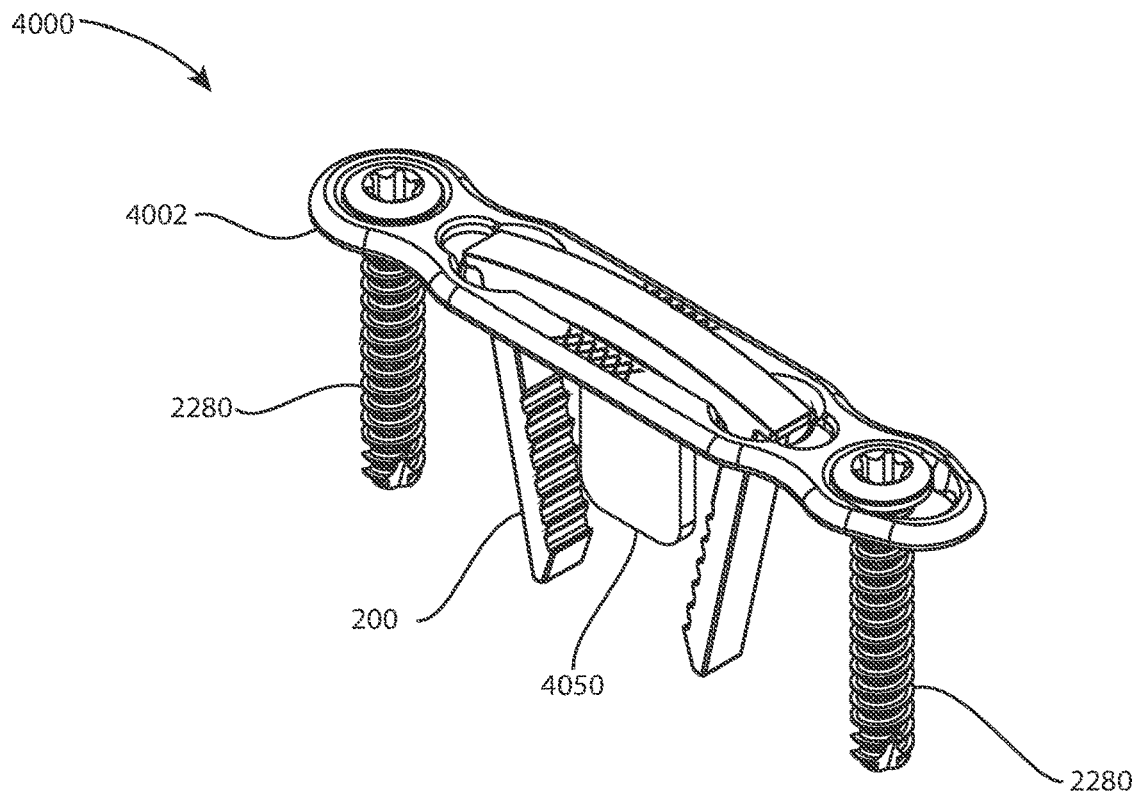
FIG. 51 is an isometric view of an implant assembly including a bone plate and a compression bone staple.
Figure 52:
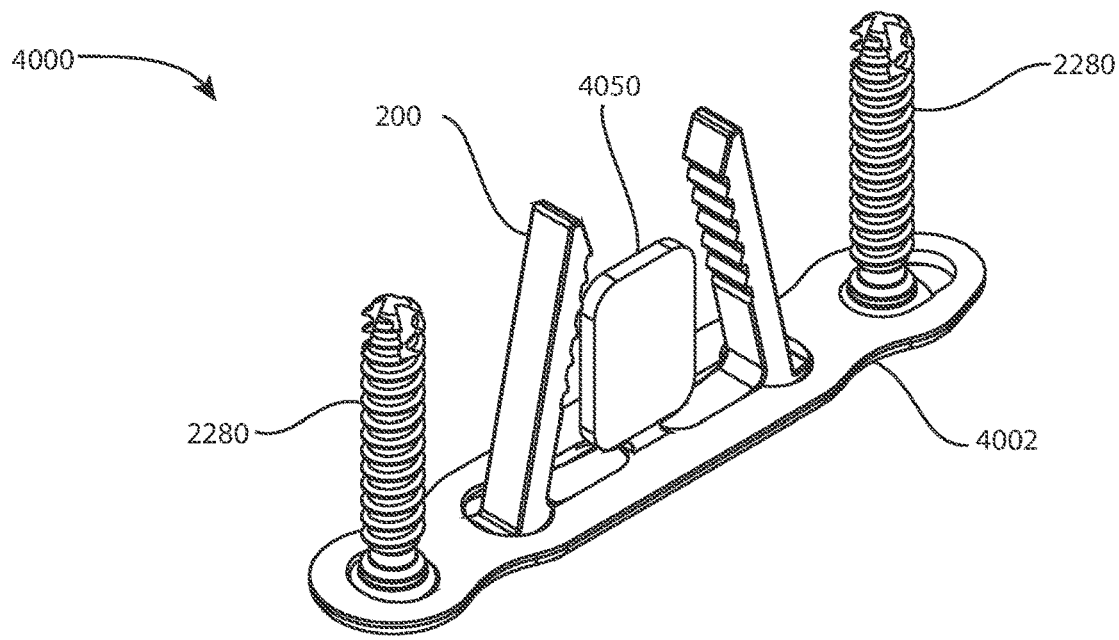
FIG. 52 is an isometric view of the implant assembly of FIG. 51 from a different direction.
Figure 53:
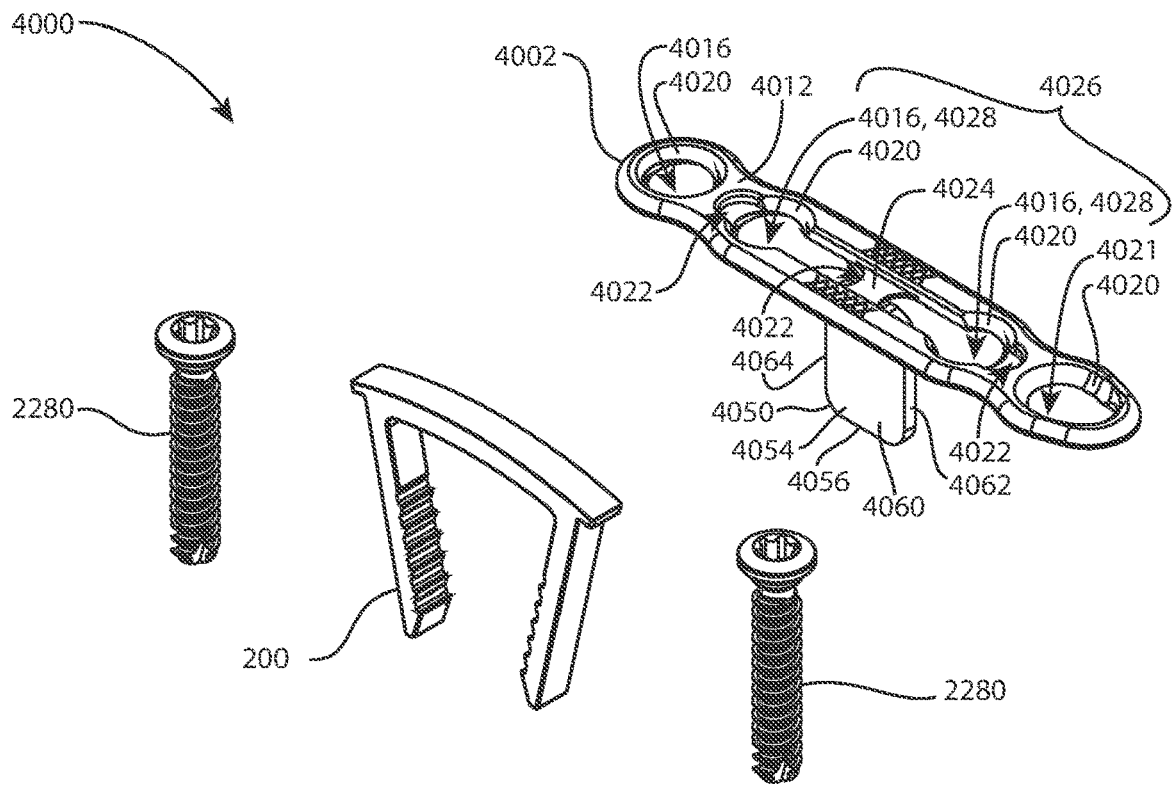
FIG. 53 is an isometric exploded view of the implant assembly of FIG. 51.
Figure 54:
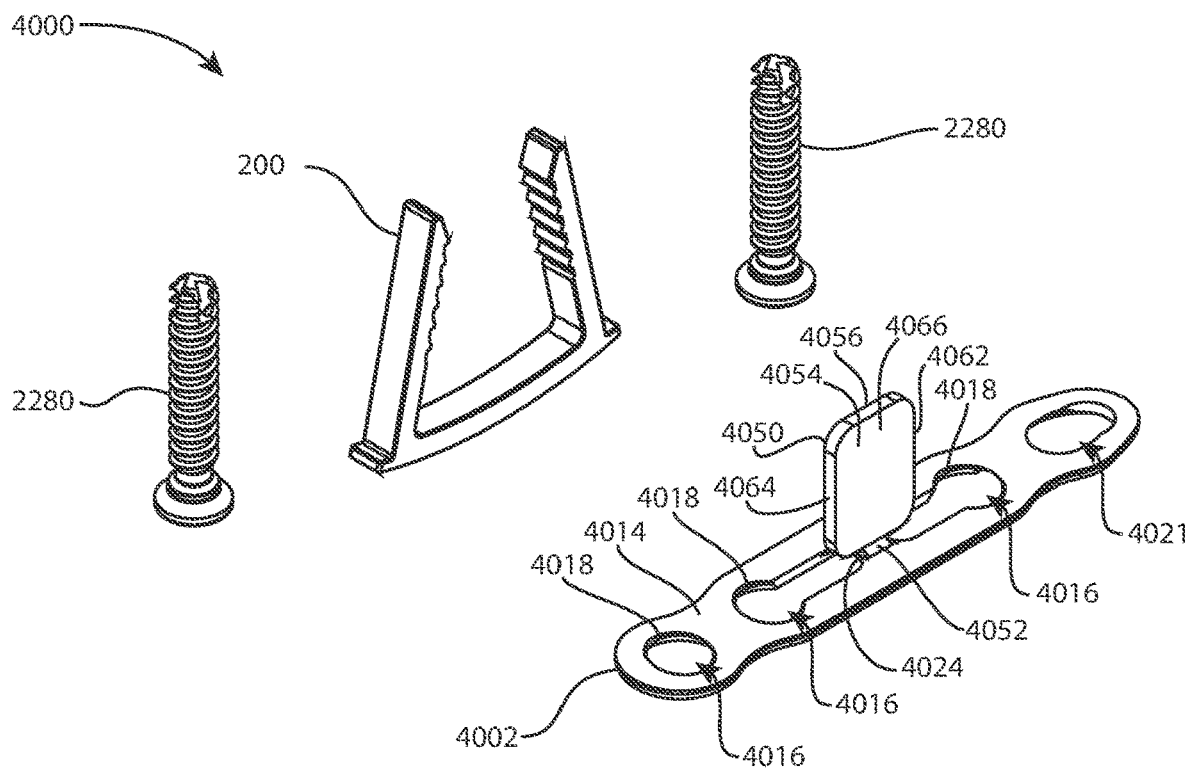
FIG. 54 is another isometric exploded view of the implant assembly of FIG. 51 from a different direction.
Figure 55:
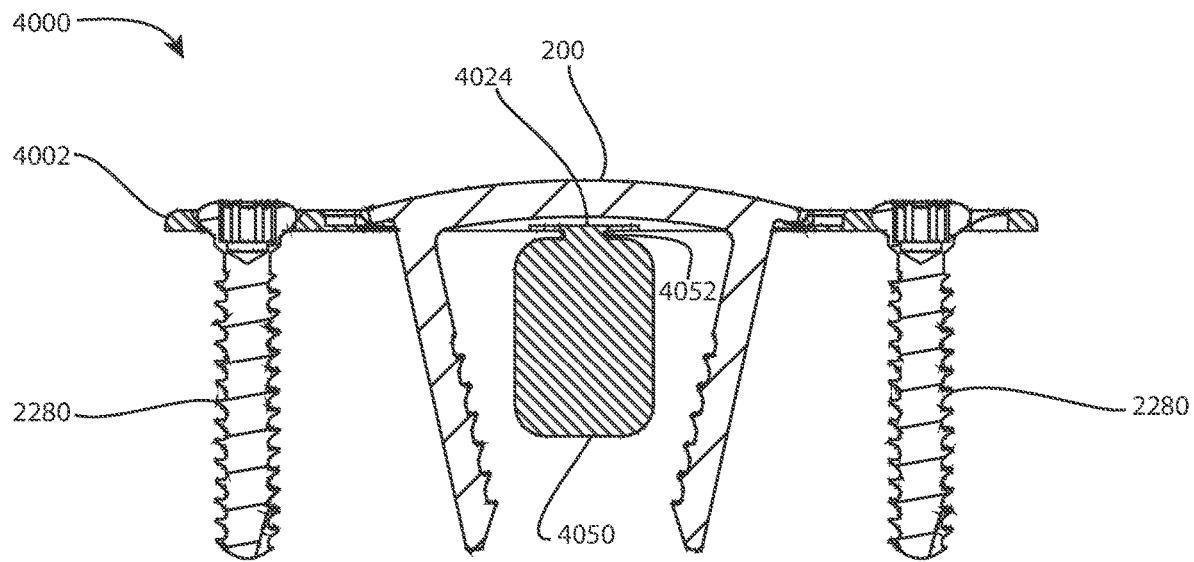
FIG. 55 is a cross-sectional view of the implant assembly of FIG. 51 taken along a mid-plane extending along the length of the plate.

The plate 4002 includes an integral anti-torque plug 4050 which extends from the reverse side 4014 of the web 4024. The plug 4050 may also be referred to as a tab, keel, post, or the like. The plug 4050 is depicted as being centered on the web 4024 between the two receiver holes 4028; in other embodiments the plug may be off-center relative to the receiver holes 4028 and/or web 4024 and/or a plurality of plugs may be included. The plug may also be connected to the plate 4002 in more than one location along the reverse side 4014. Plug 4050 includes a neck portion 4052 where the plug is joined to the web 4024, a body 4054, and a tip 4056. Neck portion 4052 may be formed as a waist having a reduced width with respect to the web 4024 or the plate 4002, as shown in FIG. 54; in other embodiments the neck portion 4052 may be wider than or equal in width with respect to the web 4024 or the plate 4002. Preferably, plug 4050 is connected to the plate 4002 only via the web 4024, and not along the remainder of the reverse side 4014. Plug 4050 may be rectangular in cross-section and includes four sides 4060, 4062, 4064, 4066. The plug thickness between sides 4060 and 4066 may be less than, the same as, similar to, or greater than the thickness of the bridge 206 and/or bone engaging members 202, 204 of the clip 200 in the same direction (front-back). Preferably, the plug thickness between sides 4060 and 4066 is less than the thickness of the bridge 206 and bone engaging members 202, 204 of the clip 200 or the screws 2280 in the same direction, as seen best in FIGS. 51 and 52. The plug tip 4056 may be tapered on at least two sides 4062, 4064 with respect to the plug body 4054 to facilitate insertion into a joint 2. The plug sides 4060, 4062, 4064, 4066 may be smooth as seen in FIGS. 51 and 52; in other embodiments one or more plug sides may include teeth, serrations, or other surface roughening. In other embodiments, the plug may have a differently shaped cross-section. The plug does not preclude compression of the bone segments by the bone engaging members 202, 204 of the clip 200 or the screws 2280 at least because the plug is oriented in a plane coplanar with, or parallel to, the plane of the bridge 206 and bone engaging members 202, 204 of the clip 200 and the screws 2280, as shown in FIGS. 51 and 52. Advantageously, the plug 4050 sustains most of the torsion across the joint 2, which relieves stress from the extracortical main body of the plate 4002. This means that the body of the plate 4002 may be made thinner than a plate lacking the plug 4050.

The implant 4000 may be operatively assembled by inserting the distal ends 236, 240 of the bone engaging members 202, 204 of the clip 200 through the receiver holes 4028 of the plate 4002. The clip 200 may be advanced until the lower surface 210 of the bridge 206 contacts the upper surface of the web 4024, so that the bridge 206 is at least partially within the groove 4022, if present. The bone engaging members 202, 204 protrude through the reverse side 4014 of the plate 4002. The clip 200 may be in the free state or an elastically deformed state. The clip 200 may be coupled to any of the inserters 2700, 3200 disclosed herein, or in the documents incorporated by reference in this application. The bilateral extensions of groove 4022 beyond the receiver holes 4028 may provide clearance for inserter jaws to engage and disengage the connecting means 214, 216 of the clip 200 when the clip is fully advanced into the receiver 4026. The illustrated groove extensions may be particularly useful for inserters with jaws that engage the connecting means 214, 216 along the longitudinal direction of the bridge 206.

A surgical method for stabilizing the joint 2 between the first and second bones 4, 6 with the implant 4000 may include any or all of the following steps in any order:

Preparing a bone slot for the plug 4050 across the joint 2 between the first and second bones 4, 6. This step may involve inserting a k-wire in the joint 2, as described above for k-wire 3750, and referencing the k-wire with an instrument to center the bone slot over the joint 2.

Placing the plate 4002 against the first and second bones 4, 6 with the plug 4050 in the bone slot.

Preparing holes for the screws 2280 in the first and second bones 4, 6. This step may involve engaging guide elements of a drill guide with the intended screw holes, for example the left-most hole 4016 and the hole 4021, and actuating a drill through each guide element to create one hole in the first bone 4 and a second hole in the second bone 6. This step may optionally involve compressing the first and second bones 4, 6 together before drilling the holes.

Inserting screws 2280 through the plate 4002 and into the bone holes for the screws.

Preparing holes for the bone engaging members 202, 204 of the clip 200 in the first and second bones 4, 6. This step may involve engaging guide elements of another drill guide with the receiver 4026, for example the receiver holes 4028, and actuating a drill through each guide element and the corresponding receiver hole 4028 to create one hole in the first bone 4, and a second hole in the second bone 6. This step may optionally involve compressing the first and second bones 4, 6 together before drilling the holes.

Inserting the bone engaging members 202, 204 of the clip 200 through the receiver holes 4028 and into the bone holes for the bone engaging members. This step may involve coupling the clip 200 to an inserter and/or moving the clip into an elastically deformed state before inserting the bone engaging members through the receiver holes and into the bone holes. This step may also involve allowing the clip 200 to move toward the relaxed or free state by actuating the inserter and/or disconnecting the inserter from the clip 200. These details are discussed above.

The implants or clips disclosed herein may be made from nitinol, titanium, stainless steel, polymers including PEEK, or any material providing the elastic properties to allow the clip to provide compression across the joint. The plugs disclosed herein may be made from PEEK, titanium, stainless steel, allograft, UHMWPE or any other biocompatible material suitable to resist joint forces for a time. Additionally, any of these materials could be coated with osteoconductive coatings/surface treatments such as hydroxyapatite, trabecular metal, porous beads, and/or nanotubes, among others. It is appreciated that the use of the implants disclosed herein is not limited to bone; any of the implants, clips, or plugs described herein may be implanted into other tissues or materials.

The terms "upper" and "lower", and "top" and "bottom", "front", "side", and "rear" are used as relative terms herein for ease of description and understanding. It is understood that in embodiments of the disclosure, upper and lower entities may be reversed, as may top and bottom, front and rear.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A system for stabilizing a first bone relative to a second bone, wherein a joint separates the first and second bones, the system comprising:

a dynamic implant having first and second legs connected by a bridge, and having a plug extending from a bone-facing side of the bridge, wherein the plug has a cross-section that is elongated along a direction parallel to the bridge, wherein the implant has a free state in which the legs converge as they extend away from the bridge, and an elastically deformed state in which the legs are substantially parallel;

a drill guide having first and second lumens corresponding to the first and second legs of the implant;

a punch guide having first and second pegs extending outwardly from a body, the first and second pegs corresponding to the first and second legs of the implant, and having a lumen extending through the body, the lumen corresponding to the cross-section of the plug; and a punch having a cutting portion that has a cross-section that corresponds to the cross-section of the plug.

2. The system of claim 1, wherein the first and second legs of the implant extend from the bone-facing side of the bridge, wherein the plug is between the first and second legs.

3. The system of claim 1, wherein the plug is integral to the bridge.

4. The system of claim 3, wherein the plug comprises a neck portion that joins to the bridge, wherein the neck portion has a reduced width relative to a remainder of the plug.

5. The system of claim 1, wherein the plug is a separate part that connects to the bridge.

6. The system of claim 1, wherein when the cutting portion of the punch is inserted through the lumen of the punch guide, a distal end of the cutting portion of the punch protrudes from the lumen of the punch guide between the first and second pegs.

7. The system of claim 6, wherein the punch comprises a handle extending from the cutting portion, wherein the handle has a cross-section that is wider or thicker than the cross-section of the cutting portion, wherein when the cutting portion of the punch is inserted through the lumen of the punch guide, the handle of the punch abuts the body of the punch guide and protrudes away from the punch guide opposite the protruding distal end of the cutting portion of the punch.

8. The system of claim 1, comprising:
an inserter removably connectable to the implant, wherein actuation of the inserter moves the implant between the free state and the elastically deformed state.

9. The system of claim 1, wherein the first and second pegs are integrally formed with the body of the punch guide.

10. The system of claim 1, wherein the first and second pegs are separate from the body of the punch guide.

11. A system for stabilizing a first bone relative to a second bone, wherein a joint separates the first and second bones, the system comprising:

a dynamic implant having first and second legs connected by a bridge, and having a plug extending from a bone-facing side of the bridge, wherein the plug has a cross-section that is elongated along a direction parallel to the bridge, the plug is integral to the bridge, the plug comprises a neck portion that loins to the bridge, and the neck portion has a reduced width relative to a remainder of the plug, and wherein the implant has a free state in which the legs converge as they extend away from the bridge, and an elastically deformed state in which the legs are substantially parallel; and a drill guide having first and second lumens corresponding to the first and second legs of the implant, and a third lumen corresponding to the cross-section of the plug.

12. The system of claim 11, further comprising:
a punch guide having first and second pegs extending outwardly from a body, the first and second pegs corresponding to the first and second legs of the implant, and having a lumen extending through the body, the lumen corresponding to the cross-section of the plug; and a punch having a cutting portion that has a cross-section that corresponds to the cross-section of the plug.

13. The system of claim 12, wherein when the cutting portion of the punch is inserted through the lumen of the punch guide, a distal end of the cutting portion of the punch protrudes from the lumen of the punch guide between the first and second pegs.

14. The system of claim 13, wherein the punch comprises a handle extending from the cutting portion, wherein the handle has a cross-section that is wider or thicker than the cross-section of the cutting portion, wherein when the cutting portion of the punch is inserted through the lumen of the punch guide, the handle of the punch abuts the body of the punch guide and protrudes away from the punch guide opposite the protruding distal end of the cutting portion of the punch.

15. The system of claim 11, wherein the first and second legs of the implant extend from the bone-facing side of the bridge, wherein the plug is between the first and second legs.

16. The system of claim 11, wherein the plug is a separate part that connects to the bridge.

17. The system of claim 11, wherein the drill guide comprises a k-wire receiving feature corresponding to a center of the plug, wherein the k-wire receiving feature extends parallel to and between the first and second lumens.

18. The system of claim 11, comprising:
an inserter removably connectable to the implant, wherein actuation of the inserter moves the implant between the free state and the elastically deformed state.

19. The system of claim 12, wherein the first and second pegs are integrally formed with the body of the punch guide.

20. The system of claim 12, wherein the first and second pegs are separate from the body of the punch guide.

21. A system for stabilizing a first bone relative to a second bone, wherein a joint separates the first and second bones, the system comprising:

a dynamic implant having first and second legs connected by a bridge, and having a plug extending from a bone-facing side of the bridge, wherein the plug has a cross-section that is elongated along a direction parallel to the bridge, wherein the implant has a free state in which the legs converge as they extend away from the bridge, and an elastically deformed state in which the legs are substantially parallel; and a drill guide having first and second lumens corresponding to the first and second legs of the implant, and a linear slot corresponding to a center of the plug, wherein the linear slot forms an elongate opening in a side of the drill guide that extends parallel to and between the first and second lumens.

22. The system of claim 21, further comprising:
a punch guide having first and second pegs extending outwardly from a body, the first and second pegs corresponding to the first and second legs of the implant, and having a lumen extending through the body, the lumen corresponding to the cross-section of the plug; and a punch having a cutting portion that has a cross-section that corresponds to the cross-section of the plug.

23. The system of claim 22, wherein when the cutting portion of the punch is inserted through the lumen of the punch guide, a distal end of the cutting portion of the punch protrudes from the lumen of the punch guide between the first and second pegs.

24. The system of claim 23, wherein the punch comprises a handle extending from the cutting portion, wherein the handle has a cross-section that is wider or thicker than the cross-section of the cutting portion, wherein when the cutting portion of the punch is inserted through the lumen of the punch guide, the handle of the punch abuts the body of the punch guide and protrudes away from the punch guide opposite the protruding distal end of the cutting portion of the punch.

25. The system of claim 21, wherein the first and second legs of the implant extend from the bone-facing side of the bridge, wherein the plug is between the first and second legs.

26. The system of claim 21, wherein the plug is integral to the bridge.

27. The system of claim 26, wherein the plug comprises a neck portion that joins to the bridge, wherein the neck portion has a reduced width relative to a remainder of the plug.

28. The system of claim 21, wherein the plug is a separate part that connects to the bridge.

29. The system of claim 21, comprising:

an inserter removably connectable to the implant, wherein actuation of the inserter moves the implant between the free state and the elastically deformed state.

30. The system of claim 22, wherein the first and second pegs are integrally formed with the body of the punch guide.

31. The system of claim 22, wherein the first and second pegs are separate from the body of the punch guide.

32. The system of claim 21, wherein the linear slot is configured to receive a k-wire through the elongate opening.

* * * * *